US010544424B2

(12) United States Patent
DiPetrillo et al.

(10) Patent No.: US 10,544,424 B2
(45) Date of Patent: Jan. 28, 2020

(54) ALGAL CHLOROPLASTIC SRP54 MUTANTS

(71) Applicant: SYNTHETIC GENOMICS, INC., La Jolla, CA (US)

(72) Inventors: Christen G. DiPetrillo, San Diego, CA (US); Jay McCarren, Cardiff, CA (US); Leah Soriaga, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 162 days.

(21) Appl. No.: 15/130,866

(22) Filed: Apr. 15, 2016

(65) Prior Publication Data

US 2016/0304896 A1 Oct. 20, 2016

Related U.S. Application Data

(60) Provisional application No. 62/148,071, filed on Apr. 15, 2015.

(51) Int. Cl.

| | |
|---|---|
| ***C12N 15/82*** | (2006.01) |
| ***C07K 14/405*** | (2006.01) |
| ***C12N 1/12*** | (2006.01) |
| ***C12P 7/64*** | (2006.01) |

(52) U.S. Cl.

CPC ........ *C12N 15/8269* (2013.01); *C07K 14/405* (2013.01); *C12N 1/12* (2013.01); *C12N 15/8218* (2013.01); *C12N 15/8247* (2013.01); *C12P 7/64* (2013.01)

(58) Field of Classification Search

CPC .................................................... C07K 14/405

See application file for complete search history.

(56) References Cited

U.S. PATENT DOCUMENTS

| | | | |
|---|---|---|---|
| 9,012,723 B2 * | 4/2015 | Guo .................... | C07K 14/415 800/285 |
| 2014/0220638 A1 | 8/2014 | Bailey et al. | |
| 2014/0295448 A1 | 10/2014 | Melis et al. | |

FOREIGN PATENT DOCUMENTS

| | | |
|---|---|---|
| WO | WO 2014/016612 A1 | 1/2014 |
| WO | WO 2015/051342 A2 | 4/2015 |

OTHER PUBLICATIONS

Melis, A., Oct. 2011 Chlamydomonas Resource Center; 1 page.*

Jeong, J. et al., Biochemica et Biophysica Acta, 2017; vol. 1858, pp. 45-55.*

Melis, A., Closeout Report DE-FG36-05GO15041 submitted Dec. 29, 2014; Maximizing Light Utilization Efficiency and Hydrogen Production in Microalgal Cultures; pp. 1-20.*

De Mooji, T., 2016, Thesis: Antenna size reduction as a strategy to increase biomass productivity: a great potential not yet realized. Wageningen University pp. 1-196.*

Melis, A., Oct. 2011 Chlannydonnonas Resource Center pp. 1. (Year: 2011).*

Blanc et al.: "The *Chlorella variabilis NC64A genome reveals adaptation to photosymbiosis, coevolution with viruses, and cryptic sex*"; The Plant Cell, Sep. 1, 2010, vol. 22, pp. 2943-2955.

Carpinelli et al.: "*Chromosome Scale Genome Assembly and Transcriptome Profiling of Nannochloropsis gaditana in Nitrogen Depletion*"; Molecular Plant, Feb. 28, 2014, vol. 7, pp. 323-335.

Hutin et al.: "*Double Mutation cpSRP43-/cpSRP54-is Necessary to Abolish the cpSRP 1-61 Pathway Required for Thylakoid Targeting of the Light-Harvesting Chlorophyll Proteins*"; The Plant Journal, Mar. 1, 2002, vol. 29, pp. 531-543.

International Search Report dated Sep. 1, 2016, regarding PCT/US2016/027976.

Kirst et al.: "*The Chloroplast Signal Recognition Particle* (*CpSRP*) *Pathway as a Tool to Minimize Chlorophyll Antenna Size and Maximize Photosynthetic Productivity*," Biotechnology Advances; Feb. 28, 2014, vol. 32, pp. 66-72.

Merchant et al.: "*The Chlamydomonas Genome Reveals the Evolution of Key Animal and Plant Functions*"; Science, Oct. 12, 2007, vol. 318, pp. 245-250.

UniProtKB/Swiss-Prot: "*Q9AXU1: Chloroplast SRP54*"; Nov. 28, 2006, pp. 1-2. Retrieved from the Internet:<http://www.uniprot.org/uniprot/Q9AXU1.txt> on Jul. 26, 2016.

Amin, Pinky et al.: "*Arabidopsis Mutants Lacking the 43- and 54-Kilodalton Subunits of the Chloroplast Signal Recognition Particle Have Distinct Phenotypes*[1]" Plant Physiology, Sep. 1999, vol. 121, pp. 61-70.

Dunschede, Beatrix et al.: "*Chloroplast SRP54 Was Recruited for Posttranslational Protein Transport via Complex Formation with Chloroplast SRP43 during Land Plant Evolution*"; J. Bio Chem, vol. 290, No. 21, May 22, 2015, pp. 13104-13114.

Supplementary European Search Report dated Sep. 20, 2018, regarding EP 16 78 0942.

* cited by examiner

*Primary Examiner* — Russell Kallis

(74) *Attorney, Agent, or Firm* — DLA Piper LLP (US)

(57) ABSTRACT

Mutant photosynthetic microorganisms having reduced chlorophyll and increased photosynthetic efficiency are provided. The mutant strains have mutated chloroplastic SRP54 genes and exhibit increased productivity with respect to wild type strains. Also provided are mutant algal strains having mutated cytosolic SRP54 genes. Provided herein are methods of producing biomass and other products such as lipids using strains having mutations in an SRP54 gene. Also included are constructs and methods for attenuating or disrupting SRP54 genes.

14 Claims, 13 Drawing Sheets

Specification includes a Sequence Listing.

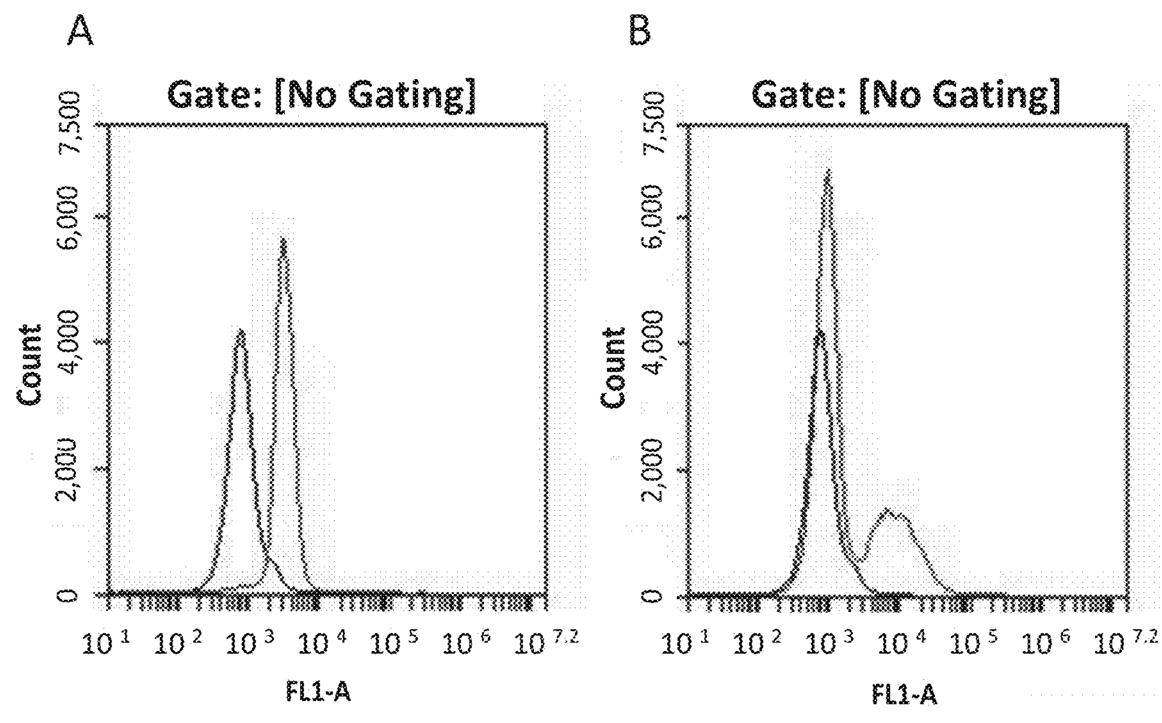
C
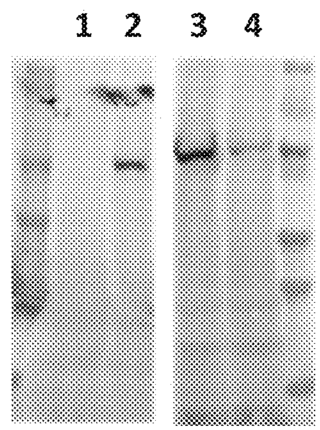
| | |
|---|---|
| 1 | WE-SGI-E-03730 |
| 2 | GE-SGI-E-06791 |
| 3 | GE-SGI-E-06571 |
| 4 | GE-SGI-E-06594 |
FIGS. 2A-C A
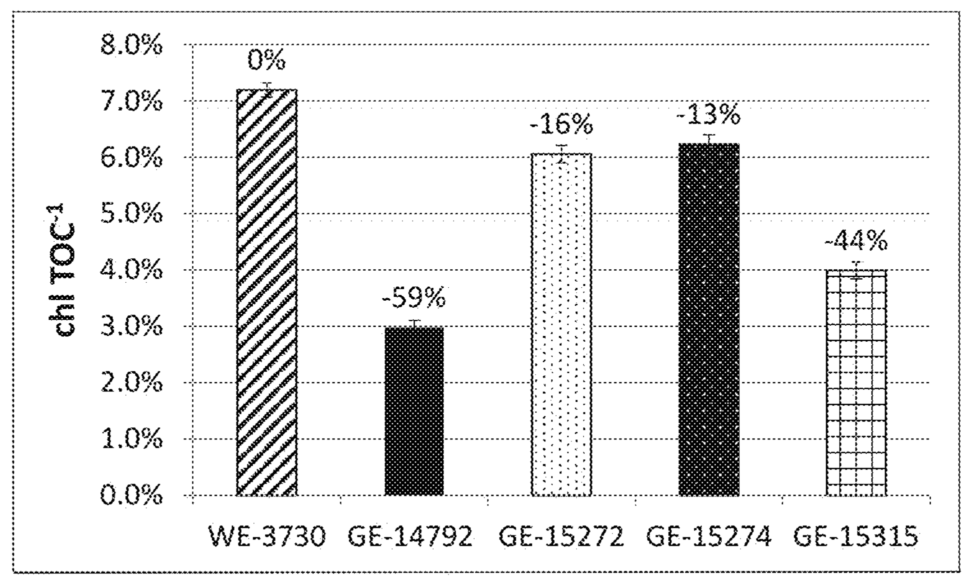
B
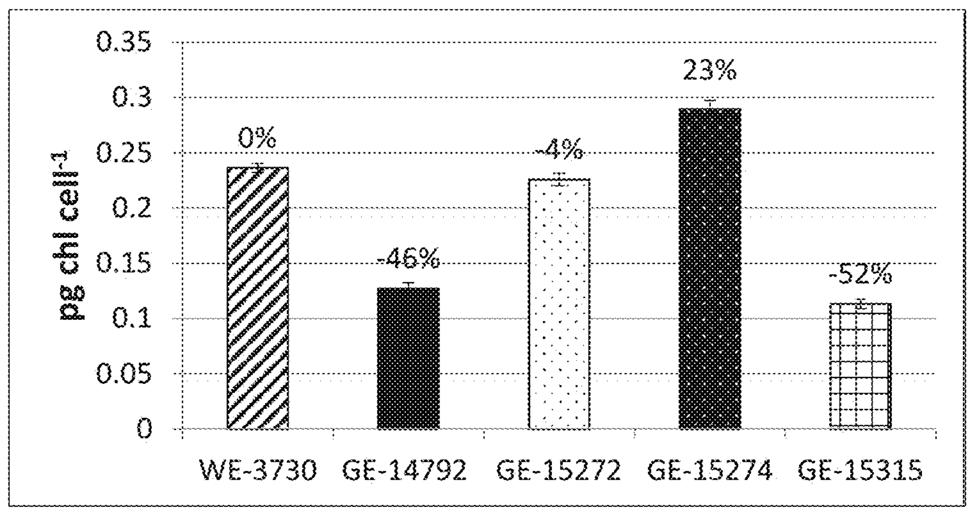
FIGS. 3A-B A
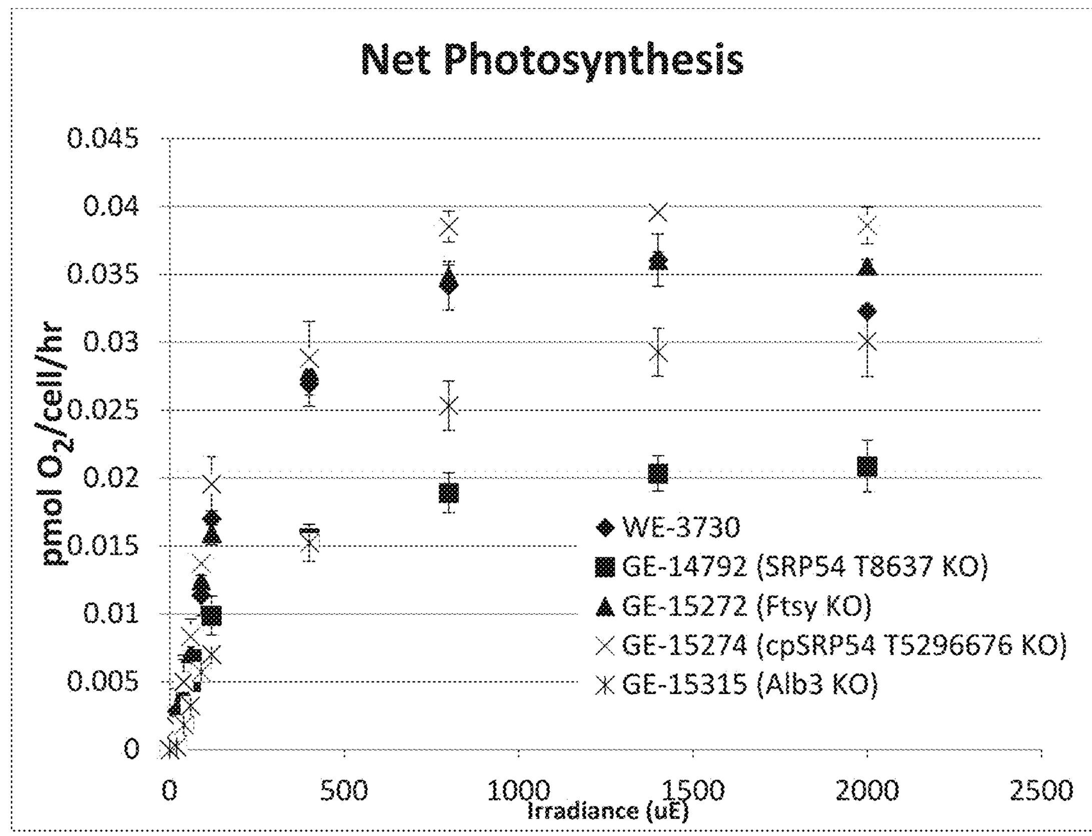
B
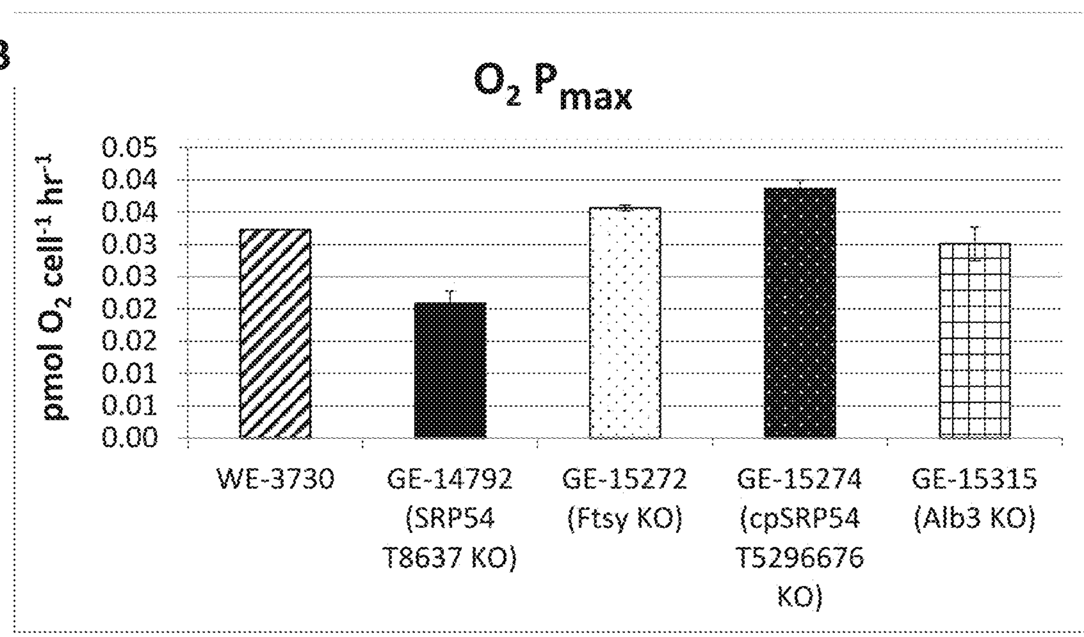
FIGS. 4A-B A
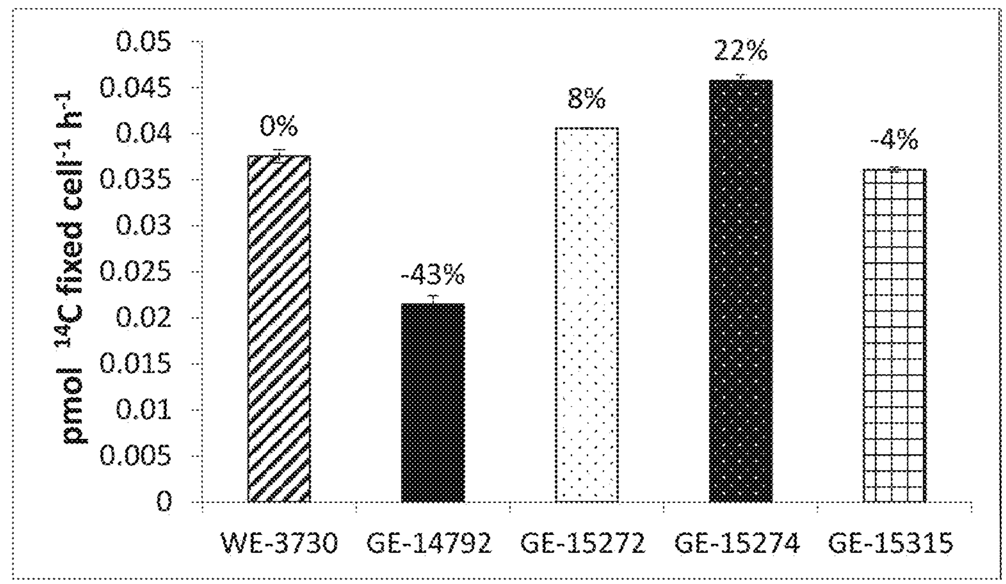
B
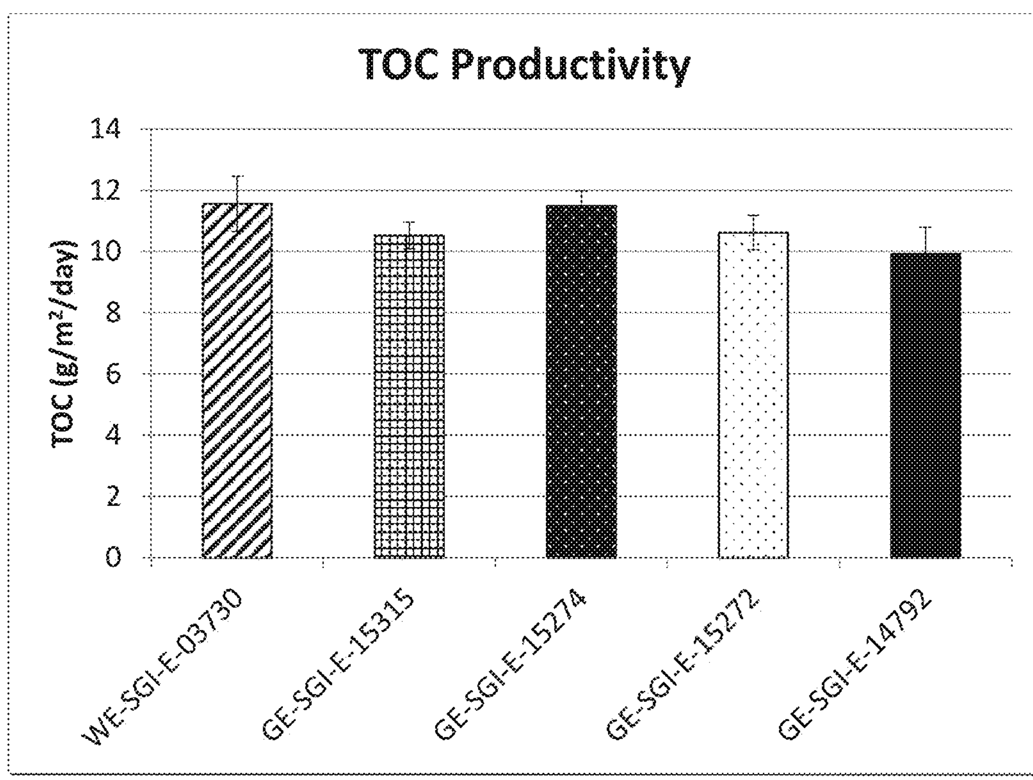
FIGS. 5A-B A
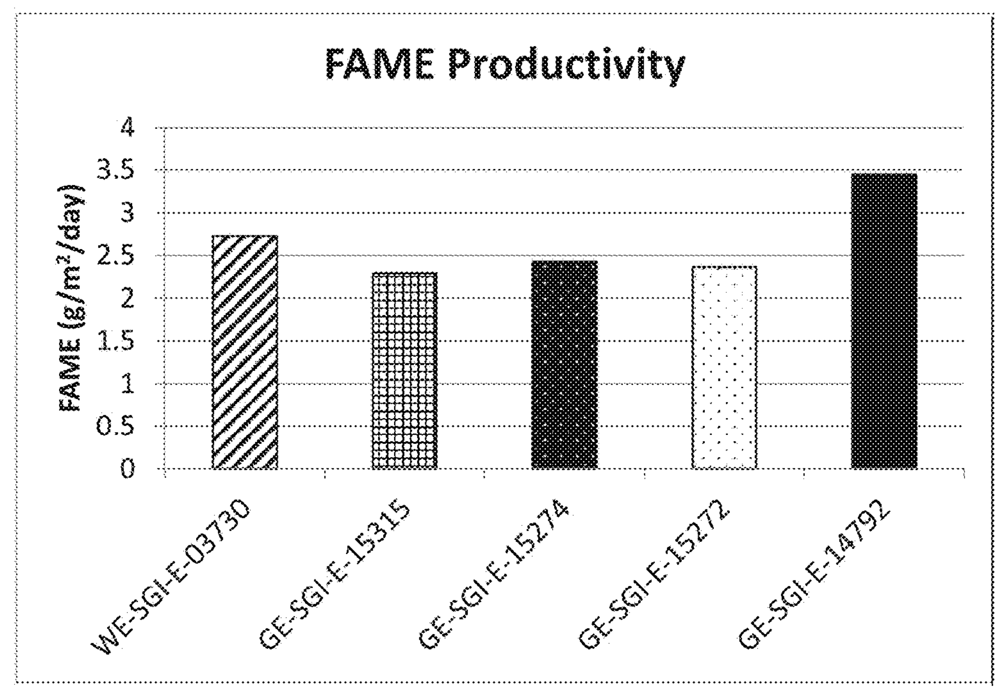
B
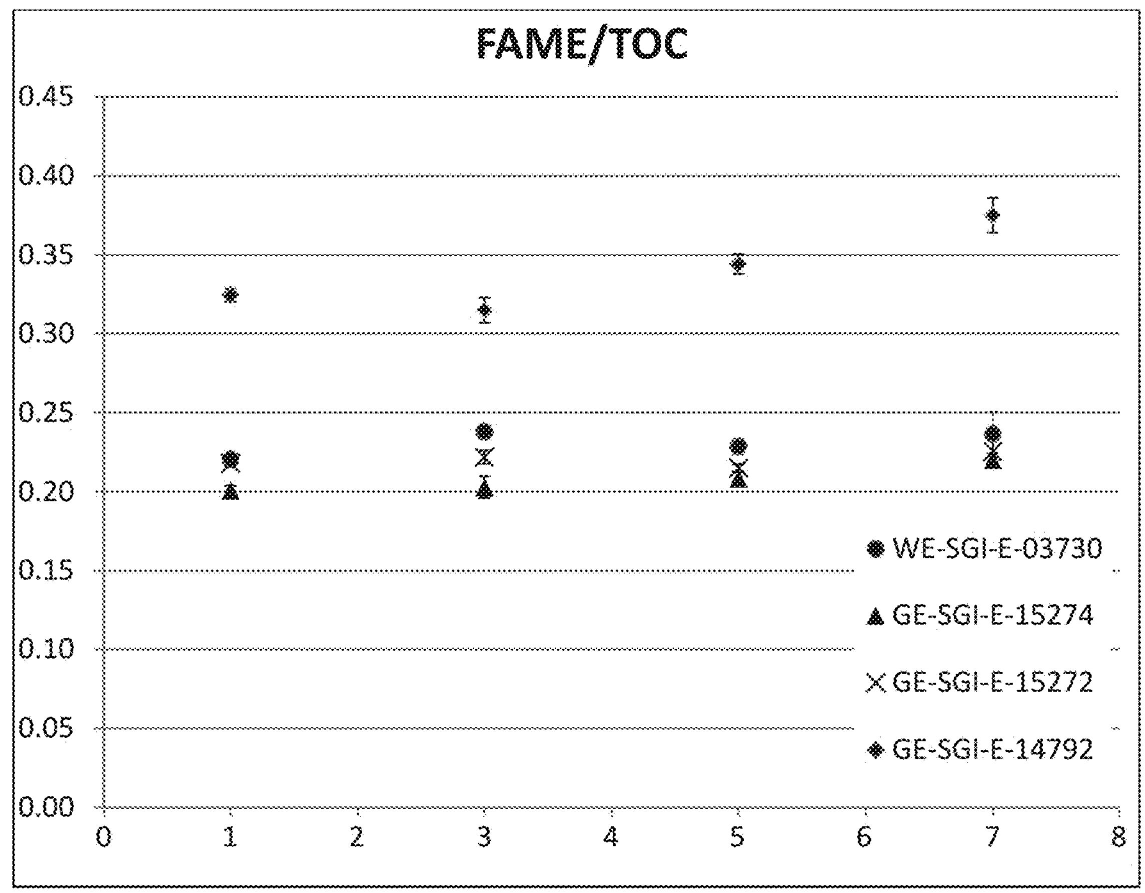
FIGS. 6A-B A
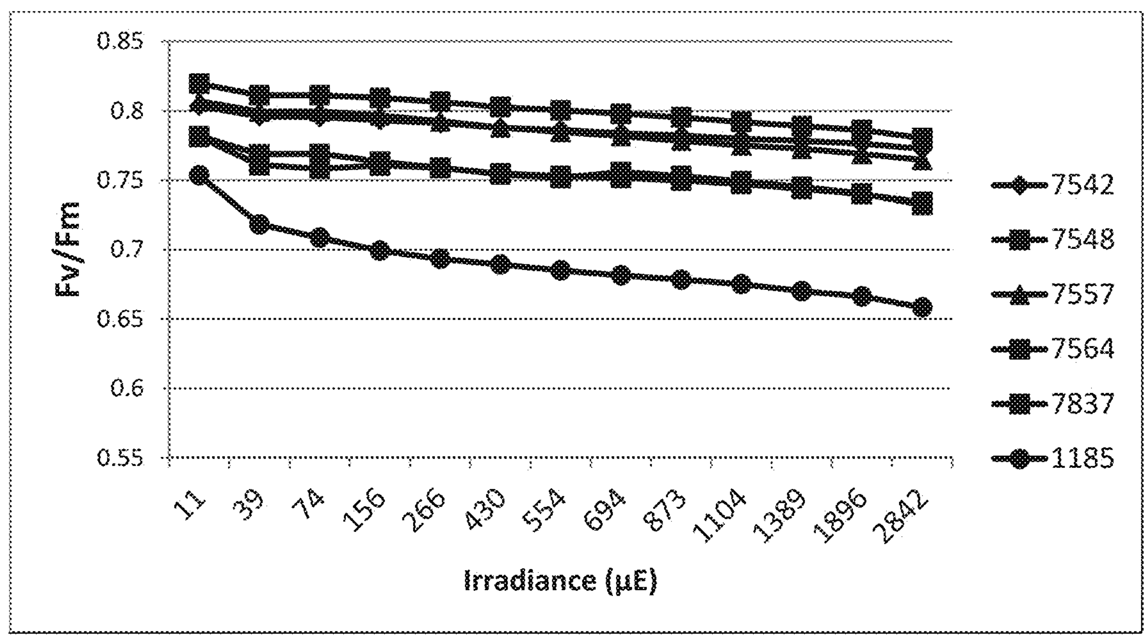
B
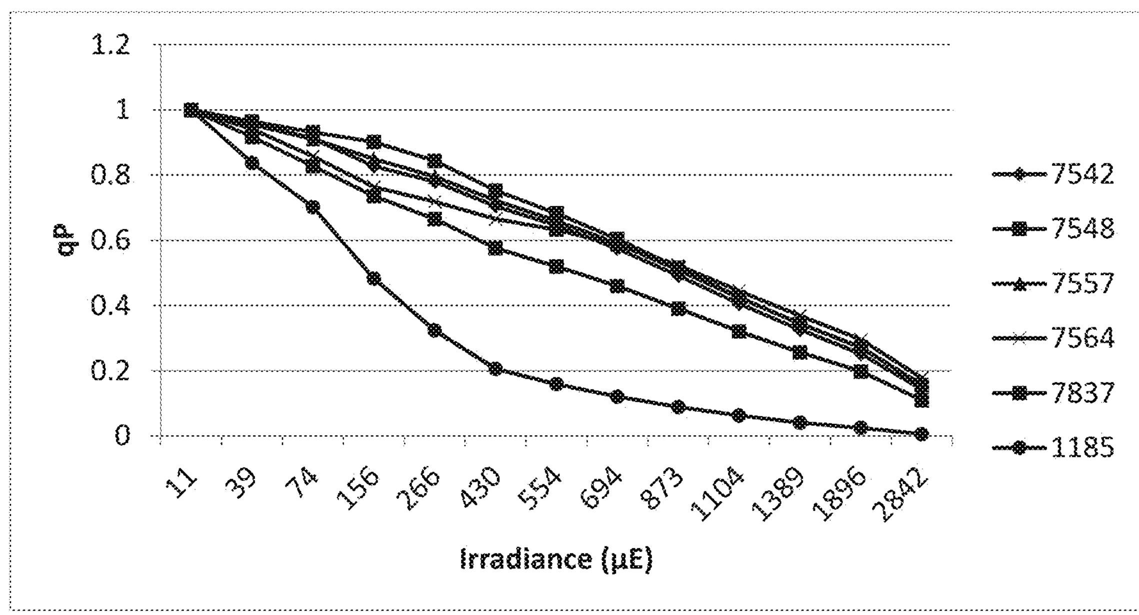
FIGS. 7A-B A
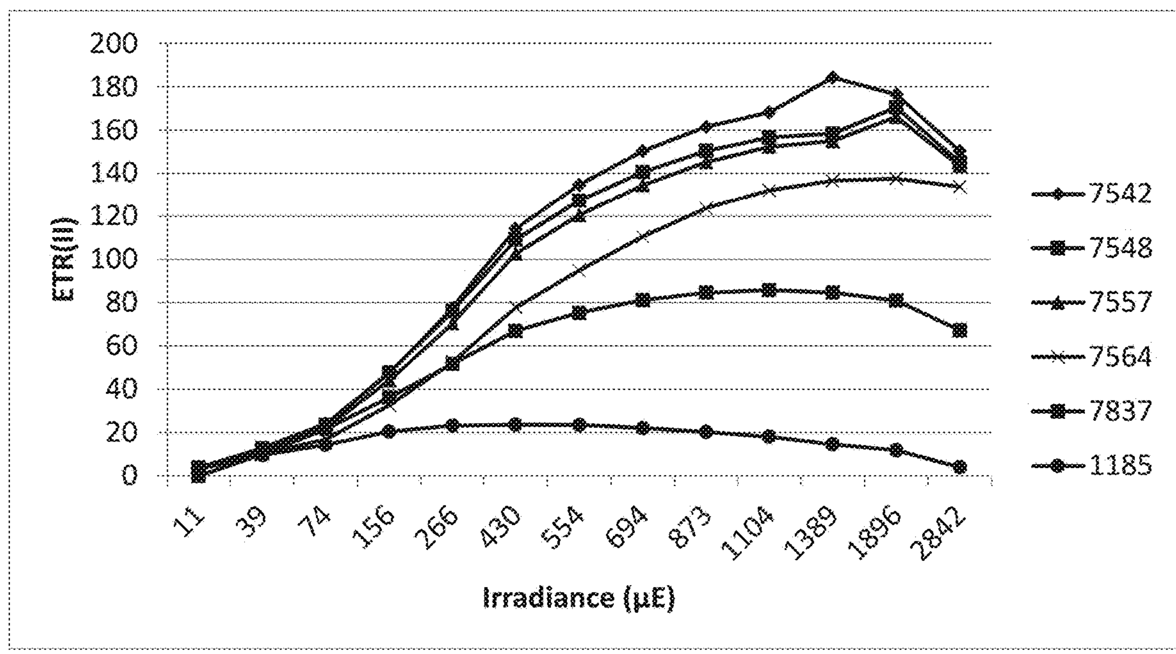
B
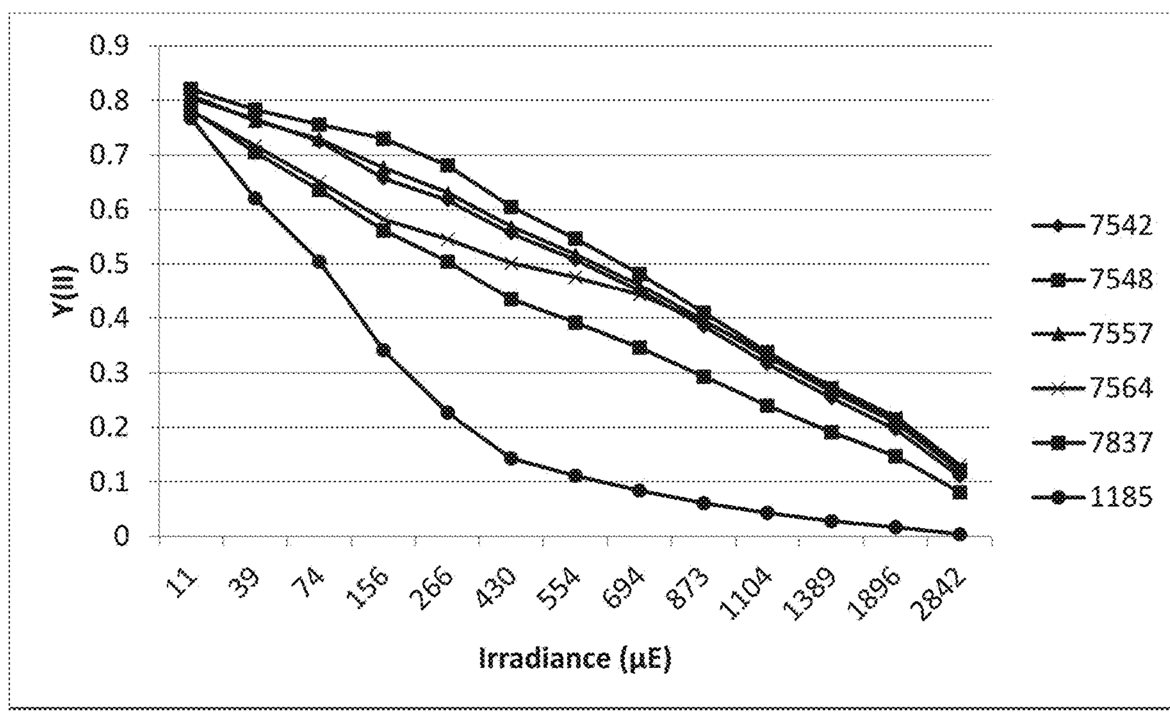
FIGS. 9A-B A
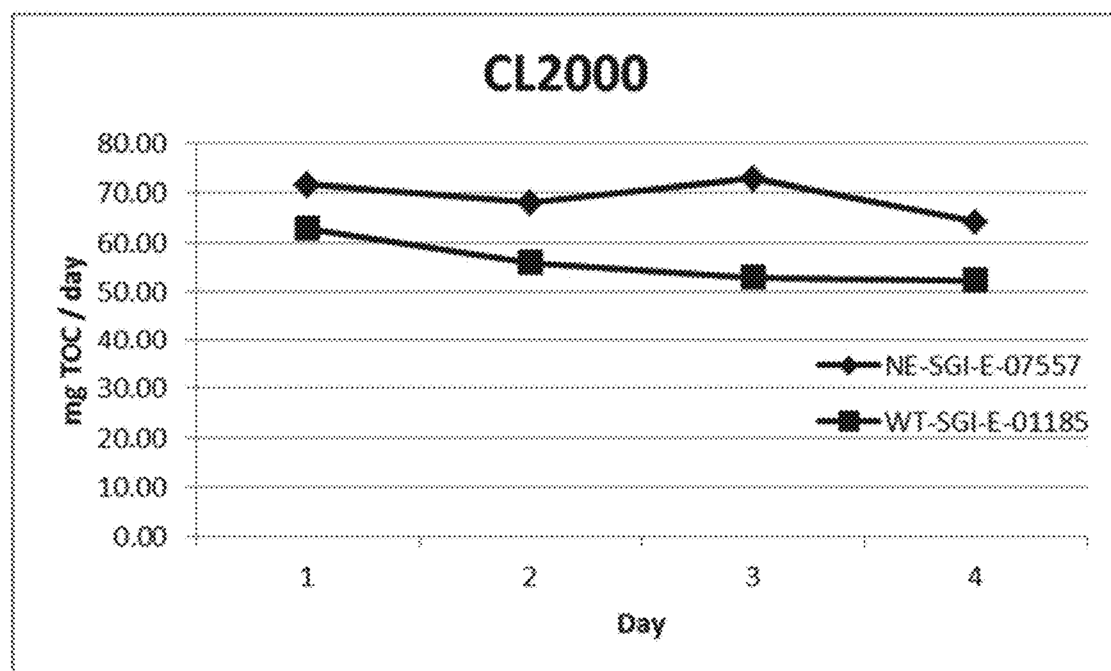
B
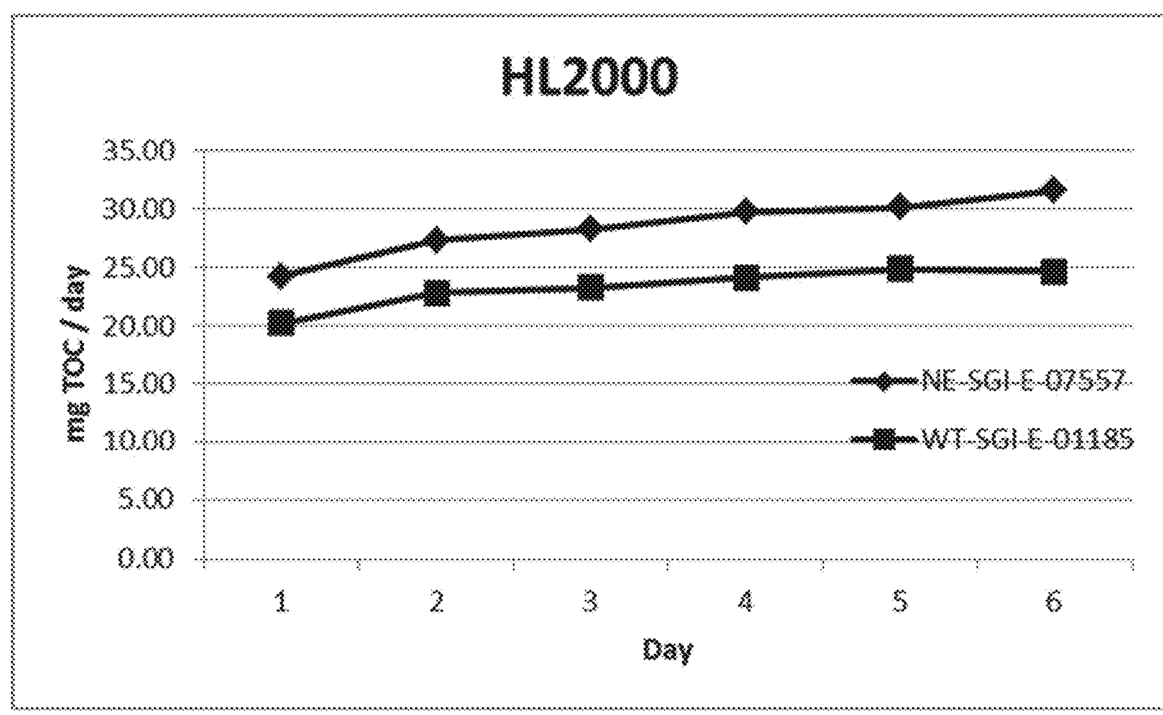
FIGS. 12A-B A
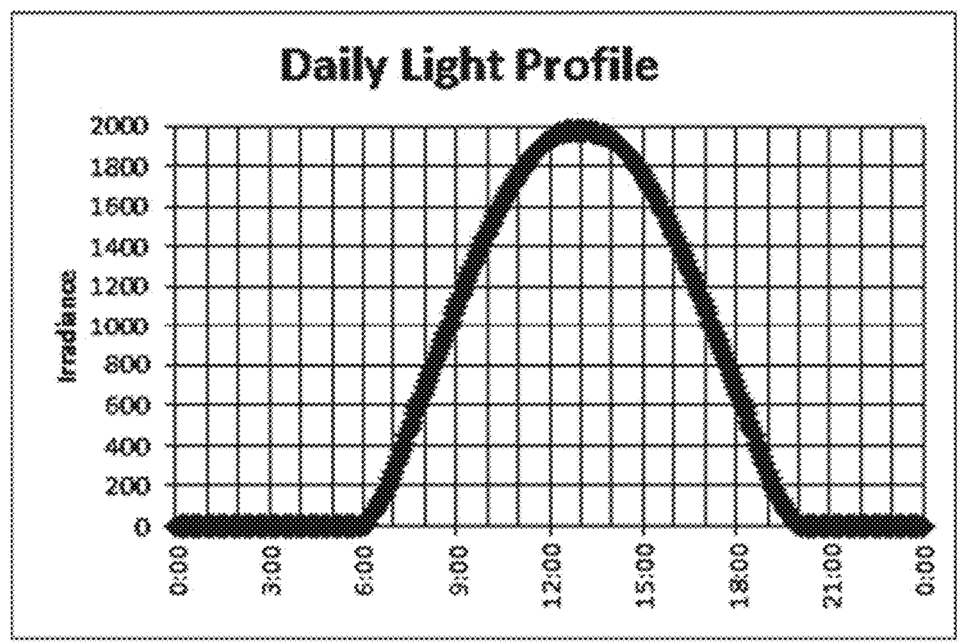
B
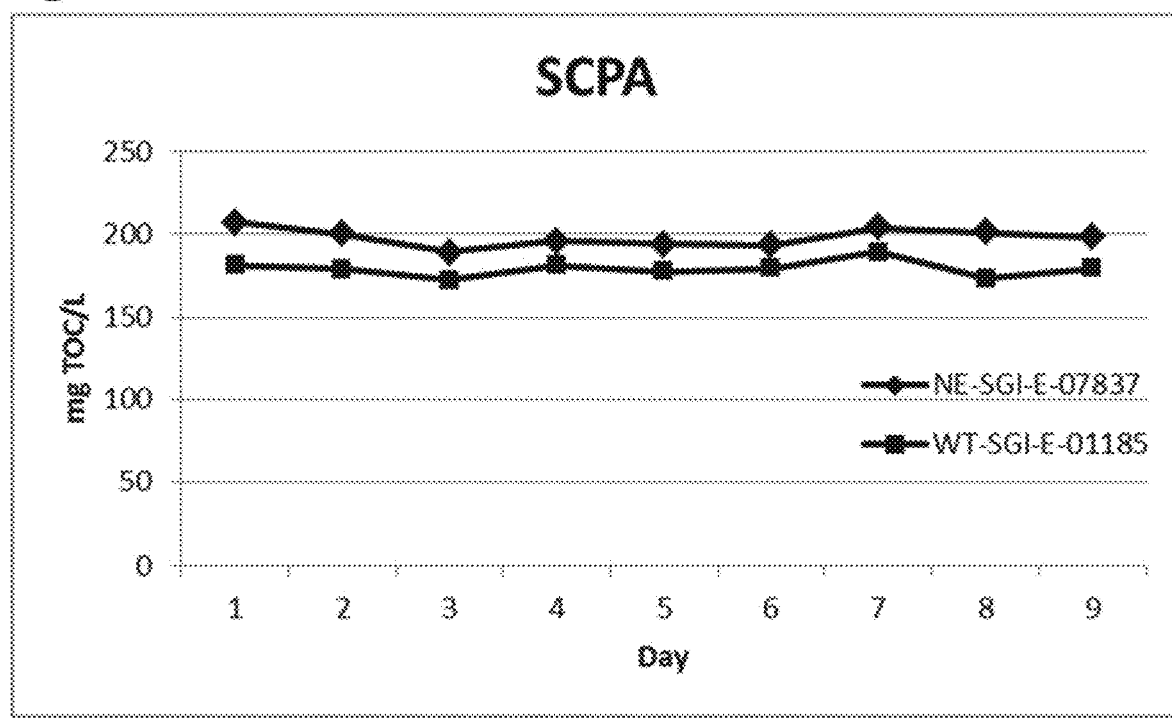
FIGS. 13A-B

SEQUENCE LISTING

```
<160> NUMBER OF SEQ ID NOS: 74

<210> SEQ ID NO 1
<211> LENGTH: 1707
<212> TYPE: DNA
<213> ORGANISM: Parachlorella sp.
<220> FEATURE:
<221> NAME/KEY: misc_feature
<223> OTHER INFORMATION: encodes cpSRP54

<400> SEQUENCE: 1

atgcttcggc agcagctgtt gcacagcggc aggcagccgg gtgcgacatg cagcttacta     60

acctgctcga catggcgacc gtctgccttg ttcggccgtc ctaagcccca aaaactgcac    120

agccagcgct tgcagcatca gggccgcccc tcccgcctcg tcgtgcgcag cgcaatgttc    180

gacaacctga gccgcagcct ggagagggcg tgggacatgg tgcgcaagga cgggcggcta    240

acggcggaca acatcaagga gcccatgcgg gagattcgca gggcgctgct tgaggcggat    300

gtgaggctgg gggcgccgct gatcagattc ttggtatcta cccccccccc ctcccaggtc    360

tccctccccg tggtgcgcaa gtttgtgaag gcggtggagg agaaggcgct gggttctgca    420

gtgaccaagg gtgtcacccc cgaccagcag ctggtgaagg tggtgtacga ccagctgcgg    480

gagctgatgg gggggcagca ggaagggctg gtgcccactt cgccagagga gccgcaggtg    540

atcttgatgg cggggctgca gggcacgggg aagacgacag ctgcggggaa gctggccttg    600
```

```
ttcctgcaga agaaggggca gaaggtgctg ctggtggcca ccgacatcta ccgccccgcc    660

gccatcgacc agctggtgaa gctgggcgac aggatagggg tgccggtgtt ccagctggga    720

acccaggtgc agccgccgga gattgcaagg caggggctgg agaaggcgcg agcagagggg    780

tttgacgccg tcatcgtcga cacggcgggg cggctgcaga tcgaccagag catgatggag    840

gagctggtgc agatcaagtc cacggtgaag ccctccgaca cgctgctagt ggtcgatgcg    900

atgacggggc aggaggcagc cgggctggtg aaggcgttca atgatgccgt ggacatcaca    960

ggcgccgtgc tgaccaagct tgacggggac agccgcggcg gcgccgcgct gagcgtgcgc   1020

caggtcagcg ggcggcccat caagtttgtg ggcatggggg agggcatgga ggcgctggag   1080

cccttctacc ccgagcgcat ggccagcagg attctgggca tgggtgacgt ggtcaccctg   1140

gtggagaagg ctgaggagag catcaaggaa gaggaggcgc aggagatatc gcggaagatg   1200

ctgtcggcca aatttgactt tgacgacttc ctgaagcagt acaagatggt ggcggggatg   1260

gggaacatgg cccaaatcat gaagatgctg ccaggcatga acaagtttac ggagaagcag   1320

ctggcgggcg ttgagaagca gtacaaggtg tacgagagca tgatccagag catgacggtg   1380

aaggagcgca agcagccgga gctgttggtg aagtcgccct ccaggaggcg gcgcatagcg   1440

cgcgggtcgg ggcgctcgga gcgggaggtc acagagctgc tgggggtgtt caccaacctg   1500

cggacgcaga tgcagagctt ctccaaaatg atggccatgg gggggatggg catgggctcc   1560

atgatgagcg acgaggagat gatgcaggcc acgctggcag gcgccggccc ccgccccgtg   1620

ccagctggca aggtgcggcg gaagaagctg gccgcggcgg gcgggtcgcg gggcatggct   1680

gagctggcat ccctgaaggc agaatga                                       1707
```

<210> SEQ ID NO 2
<211> LENGTH: 568
<212> TYPE: PRT
<213> ORGANISM: Parachlorella sp.
<220> FEATURE:
<221> NAME/KEY: misc_feature
<223> OTHER INFORMATION: cpSRP54

<400> SEQUENCE: 2

```
Met Leu Arg Gln Gln Leu Leu His Ser Gly Arg Gln Pro Gly Ala Thr
1               5                   10                  15

Cys Ser Leu Leu Thr Cys Ser Thr Trp Arg Pro Ser Ala Leu Phe Gly
            20                  25                  30

Arg Pro Lys Pro Gln Lys Leu His Ser Gln Arg Leu Gln His Gln Gly
        35                  40                  45

Arg Pro Ser Arg Leu Val Val Arg Ser Ala Met Phe Asp Asn Leu Ser
    50                  55                  60

Arg Ser Leu Glu Arg Ala Trp Asp Met Val Arg Lys Asp Gly Arg Leu
65                  70                  75                  80

Thr Ala Asp Asn Ile Lys Glu Pro Met Arg Glu Ile Arg Arg Ala Leu
                85                  90                  95

Leu Glu Ala Asp Val Arg Leu Gly Ala Pro Leu Ile Arg Phe Leu Val
            100                 105                 110

Ser Thr Pro Pro Pro Ser Gln Val Ser Leu Pro Val Val Arg Lys Phe
        115                 120                 125

Val Lys Ala Val Glu Glu Lys Ala Leu Gly Ser Ala Val Thr Lys Gly
    130                 135                 140

Val Thr Pro Asp Gln Gln Leu Val Lys Val Val Tyr Asp Gln Leu Arg
145                 150                 155                 160
```

```
Glu Leu Met Gly Gly Gln Gln Glu Gly Leu Val Pro Thr Ser Pro Glu
                165                 170                 175

Glu Pro Gln Val Ile Leu Met Ala Gly Leu Gln Gly Thr Gly Lys Thr
            180                 185                 190

Thr Ala Ala Gly Lys Leu Ala Leu Phe Leu Gln Lys Lys Gly Gln Lys
        195                 200                 205

Val Leu Leu Val Ala Thr Asp Ile Tyr Arg Pro Ala Ala Ile Asp Gln
    210                 215                 220

Leu Val Lys Leu Gly Asp Arg Ile Gly Val Pro Val Phe Gln Leu Gly
225                 230                 235                 240

Thr Gln Val Gln Pro Pro Glu Ile Ala Arg Gln Gly Leu Glu Lys Ala
                245                 250                 255

Arg Ala Glu Gly Phe Asp Ala Val Ile Val Asp Thr Ala Gly Arg Leu
            260                 265                 270

Gln Ile Asp Gln Ser Met Met Glu Glu Leu Val Gln Ile Lys Ser Thr
        275                 280                 285

Val Lys Pro Ser Asp Thr Leu Leu Val Val Asp Ala Met Thr Gly Gln
    290                 295                 300

Glu Ala Ala Gly Leu Val Lys Ala Phe Asn Asp Ala Val Asp Ile Thr
305                 310                 315                 320

Gly Ala Val Leu Thr Lys Leu Asp Gly Asp Ser Arg Gly Gly Ala Ala
                325                 330                 335

Leu Ser Val Arg Gln Val Ser Gly Arg Pro Ile Lys Phe Val Gly Met
            340                 345                 350

Gly Glu Gly Met Glu Ala Leu Glu Pro Phe Tyr Pro Glu Arg Met Ala
        355                 360                 365

Ser Arg Ile Leu Gly Met Gly Asp Val Val Thr Leu Val Glu Lys Ala
    370                 375                 380

Glu Glu Ser Ile Lys Glu Glu Glu Ala Gln Glu Ile Ser Arg Lys Met
385                 390                 395                 400

Leu Ser Ala Lys Phe Asp Phe Asp Asp Phe Leu Lys Gln Tyr Lys Met
                405                 410                 415

Val Ala Gly Met Gly Asn Met Ala Gln Ile Met Lys Met Leu Pro Gly
            420                 425                 430

Met Asn Lys Phe Thr Glu Lys Gln Leu Ala Gly Val Glu Lys Gln Tyr
        435                 440                 445

Lys Val Tyr Glu Ser Met Ile Gln Ser Met Thr Val Lys Glu Arg Lys
    450                 455                 460

Gln Pro Glu Leu Leu Val Lys Ser Pro Ser Arg Arg Arg Arg Ile Ala
465                 470                 475                 480

Arg Gly Ser Gly Arg Ser Glu Arg Glu Val Thr Glu Leu Leu Gly Val
                485                 490                 495

Phe Thr Asn Leu Arg Thr Gln Met Gln Ser Phe Ser Lys Met Met Ala
            500                 505                 510

Met Gly Gly Met Gly Met Gly Ser Met Met Ser Asp Glu Glu Met Met
        515                 520                 525

Gln Ala Thr Leu Ala Gly Ala Gly Pro Arg Pro Val Pro Ala Gly Lys
    530                 535                 540

Val Arg Arg Lys Lys Leu Ala Ala Ala Gly Gly Ser Arg Gly Met Ala
545                 550                 555                 560

Glu Leu Ala Ser Leu Lys Ala Glu
                565
```

```
<210> SEQ ID NO 3
<211> LENGTH: 549
<212> TYPE: PRT
<213> ORGANISM: Chlamydomonas reinhardtii
<220> FEATURE:
<221> NAME/KEY: misc_feature
<223> OTHER INFORMATION: cpSRP54

<400> SEQUENCE: 3

Met Gln Thr Ala Leu Arg Ala Arg Ser Ala Ala Pro Arg Gly Ala Cys
1               5                   10                  15

Asn Arg Thr Ala Val Ala Pro Val Ala Ser Ala His Leu Arg Gly Gln
            20                  25                  30

Tyr Ala Pro Phe Ser Gly Ala Gln Ala Arg Pro Ala Leu Gly Arg Gln
        35                  40                  45

Arg Gln Gln Gln Gln Gln Gln Arg Arg Gly Ala Leu Val Ile Arg Ser
    50                  55                  60

Ala Met Phe Asp Ser Leu Ser Arg Ser Ile Glu Lys Ala Gln Arg Leu
65                  70                  75                  80

Ile Gly Lys Ser Gly Thr Leu Thr Ala Glu Asn Met Lys Glu Pro Leu
                85                  90                  95

Lys Glu Val Arg Arg Ala Leu Leu Glu Ala Asp Val Ser Leu Pro Val
            100                 105                 110

Val Arg Arg Phe Ile Lys Lys Val Glu Glu Arg Ala Leu Gly Thr Lys
        115                 120                 125

Val Arg Glu Gly Arg Ala Met Gly Thr Lys Trp Lys Ser Val Val Asn
    130                 135                 140

Cys Pro Leu Gln Asp Gly Leu Gly Asn Arg Gly Val Gly Arg Ala Arg
145                 150                 155                 160

Thr Glu Val Gly His Arg Ala Ala Cys Val His Gly Ala Arg Gly Val
                165                 170                 175

Gly Lys Thr Thr Ala Ala Gly Lys Leu Ala Leu Tyr Leu Lys Lys Ala
            180                 185                 190

Lys Lys Ser Cys Leu Leu Val Ala Thr Asp Val Tyr Arg Pro Ala Ala
        195                 200                 205

Ile Asp Gln Leu Val Lys Leu Gly Ala Ala Ile Asp Val Pro Val Phe
    210                 215                 220

Glu Met Gly Thr Asp Val Ser Pro Val Glu Ile Ala Lys Lys Gly Val
225                 230                 235                 240

Glu Glu Ala Arg Arg Leu Gly Val Asp Ala Val Ile Ile Asp Thr Ala
                245                 250                 255

Gly Arg Leu Gln Val Asp Glu Gly Met Met Ala Glu Leu Arg Asp Val
            260                 265                 270

Lys Ser Ala Val Arg Pro Ser Asp Thr Leu Leu Val Val Asp Ala Met
        275                 280                 285

Thr Gly Gln Glu Ala Ala Asn Leu Val Arg Ser Phe Asn Glu Ala Val
    290                 295                 300

Asp Ile Ser Gly Ala Ile Leu Thr Lys Met Asp Gly Asp Ser Arg Gly
305                 310                 315                 320

Gly Ala Ala Leu Ser Val Arg Glu Val Ser Gly Lys Pro Ile Lys Phe
                325                 330                 335

Val Gly Val Gly Glu Lys Met Glu Ala Leu Glu Pro Phe Tyr Pro Glu
            340                 345                 350

Arg Met Ala Ser Arg Ile Leu Gly Met Gly Asp Val Leu Thr Leu Tyr
        355                 360                 365
```

```
Glu Lys Ala Glu Ala Ala Ile Lys Glu Glu Asp Ala Gln Lys Thr Met
    370                 375                 380

Glu Arg Leu Met Glu Glu Lys Phe Asp Phe Asn Asp Phe Leu Asn Gln
385                 390                 395                 400

Trp Lys Ala Met Asn Asn Met Gly Gly Leu Gln Met Leu Lys Met Met
                405                 410                 415

Pro Gly Phe Asn Lys Ile Ser Glu Lys Gln Leu Tyr Glu Ala Glu Lys
            420                 425                 430

Gln Phe Gly Val Tyr Glu Ala Ile Ile Gly Ala Met Asp Glu Glu Glu
        435                 440                 445

Arg Ser Asn Pro Glu Val Leu Ile Lys Asn Leu Ala Arg Arg Arg Arg
    450                 455                 460

Val Ala Gln Asp Ser Gly Lys Ser Glu Ala Glu Val Thr Lys Leu Met
465                 470                 475                 480

Ala Ala Tyr Thr Ser Met Lys Ala Gln Val Gly Gly Met Ser Lys Leu
                485                 490                 495

Leu Lys Leu Gln Lys Ala Gly Ala Asp Pro Gln Lys Ala Asn Ser Leu
            500                 505                 510

Leu Gln Glu Leu Val Ala Ser Ala Gly Lys Lys Val Ala Pro Gly Lys
        515                 520                 525

Val Arg Arg Lys Lys Glu Lys Glu Pro Leu Ser Lys Ala Arg Gly Phe
    530                 535                 540

Gly Ser Ser Ser Lys
545


<210> SEQ ID NO 4
<211> LENGTH: 559
<212> TYPE: PRT
<213> ORGANISM: Micromonas pusilla
<220> FEATURE:
<221> NAME/KEY: misc_feature
<223> OTHER INFORMATION: cpSRP54

<400> SEQUENCE: 4

Met Arg His Leu Leu Ser Ser Ala Ser Ile Arg Gln Tyr Asp Lys Trp
1               5                   10                  15

Ser Leu Val Ser Ser His Ala Lys Lys Pro Ala Leu Val Cys Ala Ser
            20                  25                  30

Lys His Thr Lys Ser Ala Val Lys Leu Gln Cys Thr Ser Arg Gly Ser
        35                  40                  45

Ser Asn Arg Thr Ile Gln Leu Leu Leu Phe Gln Gln Phe Arg Pro Ala
    50                  55                  60

Lys Arg Gly Lys Leu Leu Ile Thr Arg Ala Asp Ser Phe Gly Thr Leu
65                  70                  75                  80

Ser Glu Arg Leu Asn Ser Ala Trp Ser Ala Leu Lys Asp Glu Asp Asp
                85                  90                  95

Leu Ser Val Glu Asn Ile Ser Leu Pro Leu Lys Asp Ile Arg Arg Ala
            100                 105                 110

Leu Leu Glu Ala Asp Val Ser Leu Pro Val Val Arg Arg Phe Ile Lys
        115                 120                 125

Ser Val Glu Glu Lys Ser Ile Gly Val Lys Val Thr Lys Gly Val Ser
    130                 135                 140

Ala Ser Gln Gln Leu Thr Lys Val Val Ala Asp Glu Leu Cys Glu Leu
145                 150                 155                 160

Met Gly Gly Phe Gly Gly Asp Lys Leu Ile Phe Arg Lys Glu Gly Glu
                165                 170                 175
```

```
Gly Pro Thr Val Ile Leu Met Ala Gly Leu Gln Gly Val Gly Lys Thr
            180                 185                 190

Thr Ala Cys Gly Lys Leu Ala Leu Phe Leu Lys Ala Gln Gly Lys Gln
        195                 200                 205

Ser Leu Leu Val Ala Thr Asp Val Tyr Arg Pro Ala Ala Ile Asp Gln
    210                 215                 220

Leu Lys Lys Leu Gly Glu Gln Ile Asp Val Pro Val Phe Glu Leu Gly
225                 230                 235                 240

Thr Asp Phe Ser Pro Pro Asp Ile Ala Arg Ser Gly Val Glu Lys Ala
                245                 250                 255

Lys Leu Glu Asn Phe Asp Val Val Ile Val Asp Thr Ala Gly Arg Leu
            260                 265                 270

Gln Val Asp Glu Met Leu Met Ala Glu Leu Leu Ala Thr Lys Ala Ala
        275                 280                 285

Thr Arg Ala Asp Glu Thr Leu Leu Val Val Asp Ala Met Thr Gly Gln
    290                 295                 300

Glu Ala Ala Ser Leu Thr Ala Ala Phe Asn Asp Ala Val Gly Ile Thr
305                 310                 315                 320

Gly Ala Val Leu Thr Lys Met Asp Gly Asp Thr Arg Gly Gly Ala Ala
                325                 330                 335

Leu Ser Val Arg Glu Val Ser Gly Lys Pro Ile Lys Phe Ile Gly Ser
            340                 345                 350

Gly Glu Lys Leu Asp Ala Leu Glu Pro Phe Phe Pro Glu Arg Met Thr
        355                 360                 365

Thr Arg Ile Leu Gly Met Gly Asp Val Val Ser Leu Val Glu Arg Ala
    370                 375                 380

Gln Val Ala Val Lys Glu Glu Gln Ala Asn Leu Met Arg Asp Lys Ile
385                 390                 395                 400

Leu Ser Ala Thr Phe Asp Phe Asn Asp Phe Leu Ser Gln Leu Glu Met
                405                 410                 415

Met Gly Lys Met Gly Gly Met Gly Gly Leu Thr Lys Met Met Pro Gly
            420                 425                 430

Met Asn Thr Met Ser Asp Lys Glu Leu Gln Asp Ala Glu Lys Ser Leu
        435                 440                 445

Ser Val Ala Lys Ser Leu Ile Met Ser Met Thr Pro Arg Glu Arg Gln
    450                 455                 460

Phe Pro Asp Leu Leu Val Ala Gly Ser Ser Ala Ala Ser Arg Arg Gly
465                 470                 475                 480

Arg Val Val Glu Gly Ser Gly Arg Ser Asp Lys Asp Leu Ala Asn Leu
                485                 490                 495

Ile Val Met Phe Gly Ser Met Arg Val Lys Met Gln Ser Leu Ser Ala
            500                 505                 510

Gln Met Asn Gly Thr Ala Lys Glu Val Gly Leu Val Pro Gln Leu Ser
        515                 520                 525

Glu Val Asp Leu Asn Lys Leu Ala Phe Glu Gly Val Gly Lys Arg Val
    530                 535                 540

Ser Pro Gly Met Val Arg Arg Arg Lys Leu Asn Ala Ser Phe Gly
545                 550                 555
```

<210> SEQ ID NO 5
<211> LENGTH: 568
<212> TYPE: PRT
<213> ORGANISM: Micromonas sp.
<220> FEATURE:

<221> NAME/KEY: misc_feature
<223> OTHER INFORMATION: cpSRP54

<400> SEQUENCE: 5

```
Met Glu Ala Arg Thr Lys Gln Ala Arg Ala Pro Lys Gly Ser Ile Trp
1               5                   10                  15

Cys Ala Gln Arg Ala Arg Lys Asp Leu Arg Ala Arg Gly Cys Arg Gly
            20                  25                  30

Leu Gly Ser Arg Ile Ser Lys Gly Gln Pro Phe Ser Pro Leu Thr Leu
        35                  40                  45

Ser Thr Pro Ala Val Thr Glu Ile Gly Phe Gly Thr Leu Leu Tyr Gly
    50                  55                  60

Ser Arg Leu Ser Ala Gly Gly Ser Arg Arg Gly Glu Thr Met Leu Arg
65                  70                  75                  80

Arg Ala Ser Ala Phe Gly Ser Leu Thr Glu Arg Leu Asn Ser Val Trp
                85                  90                  95

Ala Thr Leu Lys Asp Glu Asp Asp Leu Ser Leu Glu Asn Ile Lys Gly
            100                 105                 110

Pro Leu Lys Asp Ile Arg Arg Ala Leu Leu Glu Ala Asp Val Ser Leu
        115                 120                 125

Pro Val Val Arg Arg Phe Ile Lys Asn Ile Glu Gln Lys Ala Ile Gly
    130                 135                 140

Thr Arg Val Thr Lys Gly Val Asn Ala Gly Gln Gln Leu Thr Lys Val
145                 150                 155                 160

Val Ala Asp Glu Leu Cys Glu Leu Met Gly Gly Phe Gly Gly Asp Ser
                165                 170                 175

Leu Ala Phe Lys Asp Pro Ser Met Gly Pro Thr Val Ile Leu Met Ala
            180                 185                 190

Gly Leu Gln Gly Val Gly Lys Thr Thr Ala Cys Gly Lys Leu Ala Leu
        195                 200                 205

Tyr Leu Lys Lys Gln Gly Lys Asp Ser Leu Leu Val Ala Thr Asp Val
    210                 215                 220

Tyr Arg Pro Ala Ala Ile Glu Gln Leu Lys Arg Leu Gly Glu Gln Val
225                 230                 235                 240

Lys Thr Pro Val Phe Asp Met Gly Val Arg Val Asp Pro Pro Glu Val
                245                 250                 255

Ala Arg Leu Gly Leu Glu Lys Ala Arg Ala Glu Gly Ile Asp Val Val
            260                 265                 270

Ile Ile Asp Thr Ala Gly Arg Leu Gln Val Asp Val His Leu Met Glu
        275                 280                 285

Glu Leu Arg Ala Thr Lys Ile Ala Thr Ala Ala Asp Glu Ile Leu Leu
    290                 295                 300

Val Val Asp Ala Met Thr Gly Gln Glu Ala Ala Ala Leu Thr Ala Ala
305                 310                 315                 320

Phe Asp Glu Ala Val Gly Ile Thr Gly Ala Val Leu Thr Lys Met Asp
                325                 330                 335

Gly Asp Thr Arg Gly Gly Ala Ala Leu Ser Val Arg Glu Val Ser Gly
            340                 345                 350

Lys Pro Ile Lys Phe Thr Gly Val Gly Glu Lys Met Glu Ala Leu Glu
        355                 360                 365

Pro Phe Tyr Pro Glu Arg Met Ala Ser Arg Ile Leu Gly Met Gly Asp
    370                 375                 380

Val Val Thr Leu Val Glu Arg Ala Gln Gln Val Val Lys Asn Glu Glu
385                 390                 395                 400
```

```
Ala Glu Gln Met Arg Asp Lys Ile Leu Ser Ala Thr Phe Asp Phe Asn
                405                 410                 415

Asp Phe Ile Lys Gln Met Glu Met Met Gly Gln Met Gly Gly Met Asp
            420                 425                 430

Gly Phe Met Lys Leu Leu Pro Gly Met Ser Gly Met Ser Glu Arg Glu
        435                 440                 445

Met Gln Glu Ala Asp Lys Ser Leu Lys Val Ala Lys Ser Leu Ile Leu
    450                 455                 460

Ser Met Thr Ser Lys Glu Arg Gln Phe Pro Asp Ile Leu Val Ala Gly
465                 470                 475                 480

Ala Ser Ala Lys Ser Arg Arg Lys Arg Ile Ile Glu Gly Ala Gly Arg
                485                 490                 495

Ser Glu Lys Asp Leu Ser Gln Leu Ile Val Leu Phe Gly Ser Met Arg
            500                 505                 510

Val Lys Met Gln Lys Met Thr Ala Glu Ile Thr Gly Ala Ser Ala Glu
        515                 520                 525

Val Gly Leu Thr Pro Gln Leu Ser Glu Glu Asp Met Asn Thr Leu Ala
    530                 535                 540

Asn Glu Gly Leu Arg Lys Asn Val Ser Pro Gly Met Val Arg Arg Leu
545                 550                 555                 560

Arg Ile Arg Arg Leu Thr Gly Ser
                565
```

<210> SEQ ID NO 6
<211> LENGTH: 481
<212> TYPE: PRT
<213> ORGANISM: Paulinella chromatophora
<220> FEATURE:
<221> NAME/KEY: misc_feature
<223> OTHER INFORMATION: cpSRP54

<400> SEQUENCE: 6

```
Met Phe Asp Glu Leu Ser Ala Arg Phe Glu Glu Ala Val Lys Ser Leu
1               5                   10                  15

Lys Gly Leu Ser Ala Ile Thr Glu Asn Asn Val Glu Asn Ala Leu Lys
            20                  25                  30

Gln Val Arg Arg Ala Leu Ile Glu Ala Asp Val Ser Leu Val Val Val
        35                  40                  45

Lys Glu Phe Met Glu Glu Val Arg Ser Lys Ser Ile Gly Ile Glu Val
    50                  55                  60

Val Arg Gly Ile Lys Pro Asp Gln Lys Phe Ile Gln Val Val Tyr Glu
65                  70                  75                  80

Gln Leu Ile Glu Ile Met Gly Ala Asn Asn Thr Pro Leu His Lys Gln
                85                  90                  95

Ser His Thr Val Thr Val Val Leu Met Ala Gly Leu Gln Gly Ala Gly
            100                 105                 110

Lys Thr Thr Ala Ala Ala Lys Leu Ala Leu Tyr Leu Lys Asn Gln Gly
        115                 120                 125

Glu Lys Val Leu Met Val Ala Ala Asp Val Tyr Arg Pro Ala Ala Ile
    130                 135                 140

Asp Gln Leu Phe Val Leu Gly Lys Gln Ile Asp Val Glu Val Phe Thr
145                 150                 155                 160

Leu Asn Pro Glu Ser Ile Pro Glu Asp Ile Ala Ala Ala Gly Leu Gln
                165                 170                 175

Lys Ala Ile Arg Glu Gly Phe Asp Tyr Leu Ile Val Asp Thr Ala Gly
```

```
            180                 185                 190

Arg Leu Gln Ile Asp Thr Ala Met Met Gln Glu Met Val Arg Ile Arg
        195                 200                 205

Ser Ala Val Asn Pro Asn Glu Ile Leu Leu Val Val Asp Ser Met Ile
    210                 215                 220

Gly Gln Glu Ala Ala Glu Leu Thr Arg Ala Phe His Glu Gln Ile Gly
225                 230                 235                 240

Ile Thr Gly Ala Val Leu Thr Lys Leu Asp Gly Asp Ala Arg Gly Gly
                245                 250                 255

Ala Ala Leu Ser Ile Arg Lys Val Ser Gly Ala Pro Ile Lys Phe Ile
            260                 265                 270

Gly Thr Gly Glu Lys Val Glu Ala Leu Gln Pro Phe His Pro Glu Arg
        275                 280                 285

Met Ala Ser Arg Ile Leu Gly Met Gly Asp Ile Val Thr Leu Val Glu
    290                 295                 300

Lys Ala Gln Glu Glu Val Glu Leu Ala Asp Val Glu Lys Met Gln Arg
305                 310                 315                 320

Lys Leu Gln Glu Ala Ser Phe Asp Phe Ser Asp Phe Leu Gln Gln Met
                325                 330                 335

Arg Leu Val Lys Arg Met Gly Ser Leu Gly Gly Leu Met Lys Met Ile
            340                 345                 350

Pro Gly Met Asn Lys Ile Asp Ser Thr Met Leu Arg Glu Gly Glu Ala
        355                 360                 365

Gln Leu Lys Arg Ile Glu Ser Met Ile Gly Ser Met Thr Pro Thr Glu
    370                 375                 380

Arg Glu Lys Pro Glu Leu Leu Ala Ser Gln Pro Ser Arg Arg Gly Arg
385                 390                 395                 400

Ile Ala Lys Gly Ser Gly His Lys Ile Ala Asp Val Asp Lys Met Leu
                405                 410                 415

Val Asp Phe Gln Lys Met Arg Gly Phe Met Gln Gln Met Thr Lys Gly
            420                 425                 430

Asn Asn Phe Ala Asn Pro Leu Ser Met Gly Ala Asn Met Phe Ser Gln
        435                 440                 445

Pro Asn Met Thr Val Pro Gln Thr Lys Ile Ser Asn Thr Asn Glu Ser
    450                 455                 460

Arg Met Arg Asn Ser Arg Ala Thr Lys Lys Lys Lys Gly Phe Gly Gln
465                 470                 475                 480

Leu
```

<210> SEQ ID NO 7
<211> LENGTH: 498
<212> TYPE: PRT
<213> ORGANISM: Ostreococcus lucimarinus
<220> FEATURE:
<221> NAME/KEY: misc_feature
<223> OTHER INFORMATION: cpSRP54

<400> SEQUENCE: 7

```
Met Thr Arg Ala Asp Ala Phe Ala Gly Met Ser Asp Lys Leu Asp Lys
1               5                   10                  15

Ala Trp Ala Arg Leu Gln Gly Glu Lys Asp Leu Asn Ala Asp Asn Val
            20                  25                  30

Lys Ala Pro Leu Lys Asp Val Arg Arg Ala Leu Leu Glu Ala Asp Val
        35                  40                  45

Ser Leu Pro Val Val Arg Arg Phe Ile Ala Arg Cys Glu Glu Lys Ala
```

```
    50                  55                  60

Val Gly Met Lys Val Thr Lys Gly Val Glu Pro Gly Gln Met Leu Val
65                  70                  75                  80

Lys Cys Val Ala Asp Glu Leu Cys Glu Leu Met Gly Gly Val Gly Ala
                85                  90                  95

Glu Gly Ile Lys Phe Arg Asp Asp Gly Glu Pro Thr Val Val Leu Met
            100                 105                 110

Ala Gly Leu Gln Gly Val Gly Lys Thr Thr Ala Cys Gly Lys Leu Ser
        115                 120                 125

Leu Ala Leu Arg Lys Gln Gly Lys Ser Val Leu Leu Val Ala Thr Asp
    130                 135                 140

Val Tyr Arg Pro Ala Ala Ile Asp Gln Leu Lys Thr Leu Gly Lys Gln
145                 150                 155                 160

Ile Gly Val Pro Val Phe Asp Met Gly Val Asp Gly Asn Pro Pro Glu
                165                 170                 175

Ile Ala Ala Arg Gly Val Arg Lys Ala Lys Asp Glu Asp Ile Asp Val
            180                 185                 190

Val Ile Val Asp Thr Ala Gly Arg Leu Asn Ile Asp Glu Lys Leu Met
        195                 200                 205

Gly Glu Leu Lys Ala Thr Lys Glu Ala Thr Ser Ala Asp Glu Thr Leu
    210                 215                 220

Leu Val Val Asp Ala Met Thr Gly Gln Glu Ala Ala Thr Leu Thr Ala
225                 230                 235                 240

Ser Phe Asn Glu Ala Val Glu Ile Thr Gly Ala Ile Leu Thr Lys Met
                245                 250                 255

Asp Gly Asp Thr Arg Gly Gly Ala Ala Leu Ser Val Arg Glu Val Ser
            260                 265                 270

Gly Lys Pro Ile Lys Phe Thr Gly Val Gly Glu Lys Met Asp Ala Leu
        275                 280                 285

Glu Pro Phe Tyr Pro Glu Arg Met Thr Ser Arg Ile Leu Gly Met Gly
    290                 295                 300

Asp Ile Val Ser Leu Val Glu Lys Val Gln Ala Gly Val Lys Glu Glu
305                 310                 315                 320

Glu Ala Glu Lys Ile Lys Gln Lys Ile Met Ser Ala Thr Phe Asp Phe
                325                 330                 335

Asn Asp Phe Val Gly Gln Leu Glu Met Met Asn Asn Met Gly Gly Met
            340                 345                 350

Lys Gln Ile Met Gln Met Met Pro Gly Thr Ala Lys Leu Ser Glu Ala
        355                 360                 365

Asp Met Glu Ala Ala Gly Lys Ser Met Thr Ile Ala Lys Ser Leu Ile
    370                 375                 380

Asn Ser Met Thr Lys Glu Glu Arg Gln Tyr Pro Asp Met Leu Val Ala
385                 390                 395                 400

Ser Thr Thr Ala Asp Ser Arg Arg Gln Arg Ile Val Lys Gly Ser Gly
                405                 410                 415

Arg Thr Glu Ala Asp Leu Ala Gln Leu Ile Met Met Phe Gly Gly Met
            420                 425                 430

Arg Thr Gln Met Gln Lys Met Ser Gly Gln Leu Gly Gly Gln Ala Gly
        435                 440                 445

Asp Val Gly Leu Gln Pro Gln Leu Ser Glu Ala Glu Leu Ser Lys Leu
    450                 455                 460

Ala Met Asn Lys Ile Arg Lys Thr Val Lys Pro Gly Met Val Arg Arg
465                 470                 475                 480
```

```
Gln Lys Ala Lys Lys Val Pro Lys Phe Leu Ala Glu Arg Glu Ser Phe
                485                 490                 495

Ser Gln


<210> SEQ ID NO 8
<211> LENGTH: 426
<212> TYPE: PRT
<213> ORGANISM: Ostreococcus tauri
<220> FEATURE:
<221> NAME/KEY: misc_feature
<223> OTHER INFORMATION: cpSRP54

<400> SEQUENCE: 8

Met Lys Val Thr Lys Gly Val Glu Pro Gly Gln Met Leu Val Lys Ala
1               5                   10                  15

Val Ala Asp Glu Leu Cys Glu Leu Met Gly Gly Val Gly Ala Glu Gly
            20                  25                  30

Ile Lys Phe Arg Asp Asp Gly Glu Pro Thr Val Ile Leu Met Ala Gly
        35                  40                  45

Leu Gln Gly Val Gly Lys Thr Thr Ala Cys Gly Lys Leu Ser Leu Ala
    50                  55                  60

Met Arg Lys Gln Gly Lys Thr Val Leu Leu Val Ala Thr Asp Val Tyr
65                  70                  75                  80

Arg Pro Ala Ala Ile Asp Gln Leu Lys Thr Leu Gly Thr Gln Ile Gly
                85                  90                  95

Val Pro Val Phe Asp Met Gly Val Asp Ala Ser Pro Pro Glu Val Ala
            100                 105                 110

Ala Arg Gly Val Arg Lys Ala Lys Glu Glu Asp Ile Asp Val Val Ile
        115                 120                 125

Val Asp Thr Ala Gly Arg Leu Asn Ile Asp Glu Lys Leu Met Ser Glu
    130                 135                 140

Leu Lys Asp Thr Lys Leu Ala Thr Lys Ala Asp Glu Thr Leu Leu Val
145                 150                 155                 160

Val Asp Ala Met Thr Gly Gln Glu Ala Ala Asn Leu Thr Ala Ser Phe
                165                 170                 175

Gln Arg Gly Asp Gly Arg Arg Thr Arg Arg Gly Gly Ala Ala Leu Ser
            180                 185                 190

Val Ala Arg Ser Phe Arg Lys Ala His Gln Phe Thr Ala Ser Val Lys
        195                 200                 205

Met Asp Ala Leu Glu Pro Phe Tyr Pro Glu Arg Met Thr Ser Arg Ile
    210                 215                 220

Leu Gly Met Gly Asp Ile Val Ser Leu Val Glu Lys Val Gln Ser Glu
225                 230                 235                 240

Val Lys Glu Ala Glu Ala Glu Lys Leu Lys Glu Lys Ile Leu Lys Ala
                245                 250                 255

Thr Phe Asp Phe Asn Asp Phe Val Thr Gln Leu Glu Met Met Asn Asn
            260                 265                 270

Met Gly Ser Met Lys Gln Ile Met Gln Met Leu Pro Gly Thr Thr Lys
        275                 280                 285

Leu Ser Glu Ser Glu Met Glu Ala Ala Glu Lys Ser Phe Lys Ile Ala
    290                 295                 300

Arg Ser Leu Ile Asn Ser Met Thr Lys Glu Glu Arg Gln Phe Pro Asp
305                 310                 315                 320

Met Leu Val Ala Ser Thr Thr Ala Glu Ser Arg Arg Ala Arg Ile Val
                325                 330                 335
```

```
Lys Gly Ser Gly Arg Thr Glu Ala Asp Leu Ala Gln Leu Ile Ile Met
            340                 345                 350

Phe Gly Ser Met Arg Gly Lys Met Gln Gln Leu Ser Gly Glu Leu Gly
        355                 360                 365

Gly Glu Ala Gly Asn Val Gly Leu Gln Pro Gln Leu Ser Ala Ala Glu
    370                 375                 380

Leu Glu Lys Leu Thr Thr Asn Lys Leu Arg Lys Asn Ile Lys Pro Gly
385                 390                 395                 400

Met Val Arg Arg Leu Lys Ser Lys Lys Ile Pro Ile Ala Lys Asn Gly
                405                 410                 415

Asp Arg Met Gly Ile Ser Ala Ser Ala Asp
            420                 425


<210> SEQ ID NO 9
<211> LENGTH: 510
<212> TYPE: PRT
<213> ORGANISM: Volvox carteri
<220> FEATURE:
<221> NAME/KEY: misc_feature
<223> OTHER INFORMATION: cpSRP54

<400> SEQUENCE: 9

Met Ser Arg Pro Ala Ala Leu Arg Gly Ala Gly Asn Arg Lys Leu Thr
1               5                   10                  15

Ala Thr Val Thr Ala Ala His Leu Arg Gly Ile Ala Phe Thr Ser Ile
            20                  25                  30

Arg Thr Cys Gln Gly Ala Lys Gly Gly Ser Leu Gly Leu Pro His Pro
        35                  40                  45

Ser Pro Pro Leu Ala Leu Pro Arg Arg Gly Arg Gly Arg Gly Ala Ala
    50                  55                  60

Val Val Val Arg Ala Ala Met Phe Asp Asn Leu Ser Lys Ser Leu Glu
65                  70                  75                  80

Lys Ala Gln Arg Leu Ile Gly Gly Cys Glu Val Pro Gly Val Gly Val
                85                  90                  95

Val Gly Lys Ser Gly Thr Leu Thr Ala Glu Asn Met Lys Glu Pro Leu
            100                 105                 110

Lys Glu Val Arg Arg Ala Leu Leu Glu Ala Asp Val Ser Leu Pro Val
        115                 120                 125

Val Arg Arg Phe Val Lys Lys Val Glu Glu Arg Ala Leu Gly Thr Lys
    130                 135                 140

Val Ile Glu Gly Val Thr Pro Asp Val Gln Phe Ile Lys Val Val Ser
145                 150                 155                 160

Asn Glu Leu Ile Glu Leu Met Gly Gly Gly Val Gly Ala Lys Asp Leu
                165                 170                 175

Glu Pro Gly Phe Pro Gln Ile Ile Leu Met Ala Gly Leu Gln Gly Val
            180                 185                 190

Gly Lys Thr Thr Ala Ala Gly Lys Leu Ala Leu Tyr Leu Lys Lys Ala
        195                 200                 205

Lys Lys Ser Cys Leu Leu Val Ala Thr Asp Val Tyr Arg Pro Ala Ala
    210                 215                 220

Ile Asp Gln Leu Val Lys Leu Gly Ala Ala Ile Asp Val Pro Val Phe
225                 230                 235                 240

Glu Leu Gly Thr Gln Val Ser Gly Lys Pro Ile Lys Phe Val Gly Val
                245                 250                 255

Gly Glu Lys Met Glu Ala Leu Glu Pro Phe Tyr Pro Glu Arg Met Ala
```

```
            260                 265                 270

Ser Arg Ile Leu Gly Met Gly Asp Val Leu Thr Leu Tyr Glu Lys Ala
        275                 280                 285

Glu Ala Ala Ile Lys Glu Glu Asp Ala Lys Ala Val Met Asp Arg Leu
    290                 295                 300

Met Glu Glu Lys Phe Asp Phe Asn Asp Phe Leu Asn Gln Trp Lys Ser
305                 310                 315                 320

Met Asn Asn Met Gly Gly Met Gln Ile Leu Lys Met Met Pro Gly Phe
                325                 330                 335

Asn Lys Glu Arg Ser Asn Pro Glu Val Ile Ile Lys Ser Leu Ala Arg
            340                 345                 350

Arg Arg Arg Val Ala Gln Asp Ser Gly His Ser Glu Ala Glu Val Ala
        355                 360                 365

Lys Leu Met Thr Ala Tyr Thr Ala Met Arg Thr Gln Val Gly Gly Met
    370                 375                 380

Ser Lys Leu Leu Lys Leu Gln Lys Ser Gly Gly Asp Pro Ser Gln Ala
385                 390                 395                 400

Glu Lys Leu Leu Lys Glu Leu Val Ala Ser Ala Gly Lys Lys Val Ala
                405                 410                 415

Pro Gly Lys Pro Pro Gly Asp Pro Ala Gly Ser Phe Ile Ser Thr Pro
            420                 425                 430

Arg Thr Pro His Pro Pro Pro Gly Pro Leu Gly Pro Arg Ser Gln Val
        435                 440                 445

Arg Arg Lys Lys Glu Lys Glu Pro Ile Ser Lys Ala Arg Gly Phe Gly
    450                 455                 460

Ser Pro Ser Asn Phe Asn His Asp Leu Ser Pro Pro Gly Ser Ser Pro
465                 470                 475                 480

Ala Ala Tyr Thr Tyr Thr Leu Ser Arg Leu Ser Cys Gln Arg Leu Cys
                485                 490                 495

Asp Gly Gly Gly Leu Leu Asp Asp Trp Asn Leu Trp Arg Arg
            500                 505                 510


<210> SEQ ID NO 10
<211> LENGTH: 448
<212> TYPE: PRT
<213> ORGANISM: Phaeodactylum tricornutum
<220> FEATURE:
<221> NAME/KEY: misc_feature
<223> OTHER INFORMATION: cpSRP54

<400> SEQUENCE: 10

Met Ser Glu Ala Ser Ile Gln Pro Ala Leu Arg Glu Val Arg Arg Ala
1               5                   10                  15

Leu Leu Asp Ala Asp Val Asn Val Asp Val Ala Asp Thr Leu Ile Glu
            20                  25                  30

Gly Val Arg Ala Arg Ser Leu Gly Gln Glu Val Leu Glu Gly Val Thr
        35                  40                  45

Ala Glu Gln Gln Phe Val Lys Ala Met Tyr Asp Glu Leu Leu Asp Met
    50                  55                  60

Met Gly Gly Asp Ser Ser Val Pro Met Ser Asp Gly Pro Ser Asn Val
65                  70                  75                  80

Pro Val Ala Thr Leu Ala Ser Gly Thr Ala Ala Asp Pro Ala Val Ile
                85                  90                  95

Leu Leu Ala Gly Leu Gln Gly Ala Gly Lys Thr Thr Ala Ala Gly Lys
            100                 105                 110
```

```
Leu Ala Leu Phe Leu Lys Glu Gln Arg Lys Val Leu Leu Val Ala Ala
        115                 120                 125

Asp Ile Tyr Arg Pro Ala Ala Ile Lys Gln Leu Gln Val Leu Gly Glu
    130                 135                 140

Ser Ile Gly Val Glu Val Phe Thr Lys Gly Thr Asp Val Asp Pro Val
145                 150                 155                 160

Glu Ile Val Asn Ala Gly Ile Gln Lys Ala Arg Asp Glu Gly Tyr Asp
                165                 170                 175

Thr Val Ile Val Asp Thr Ala Gly Arg Gln Val Ile Asp Thr Asp Leu
            180                 185                 190

Met Asp Glu Leu Gln Arg Met Lys Arg Ala Ala Ser Pro Gln Glu Thr
        195                 200                 205

Leu Leu Ile Val Asp Ala Met Thr Gly Gln Glu Ala Ala Ser Leu Thr
    210                 215                 220

Ala Ala Phe Asp Ser Ala Ile Gly Leu Thr Gly Ala Ile Leu Thr Lys
225                 230                 235                 240

Met Asp Gly Asp Ser Arg Gly Gly Ala Ala Val Ser Val Arg Gly Val
                245                 250                 255

Ser Gly Lys Pro Ile Lys Phe Val Gly Thr Gly Glu Lys Thr Ala Asp
            260                 265                 270

Leu Glu Pro Phe Tyr Pro Asp Arg Met Ala Ser Arg Ile Leu Gly Met
        275                 280                 285

Gly Asp Val Val Ser Leu Val Glu Lys Ala Ala Ser Glu Val Ser Asp
    290                 295                 300

Ala Asp Ala Leu Lys Met Gln Gln Lys Met Leu Asp Ala Ser Phe Asp
305                 310                 315                 320

Phe Asp Asp Phe Val Lys Gln Ser Glu Leu Val Thr Lys Met Gly Ser
                325                 330                 335

Val Ala Gly Ile Ala Lys Leu Met Pro Gly Met Ala Asn Gln Leu Asn
            340                 345                 350

Met Asn Gln Ile Arg Glu Val Glu Ala Arg Leu Lys Lys Ser Lys Ser
        355                 360                 365

Met Ile Ser Ser Met Thr Lys Lys Glu Arg Ala Asn Pro Glu Leu Leu
    370                 375                 380

Ile Lys Asp Ser Ser Ala Arg Ser Arg Leu Ile Arg Ile Thr Lys Gly
385                 390                 395                 400

Ser Gly Cys Gly Leu Asp Glu Gly Gln Gln Phe Met Ser Glu Phe Gln
                405                 410                 415

Arg Met Lys Thr Met Met Ser Thr Arg Arg Phe Trp Arg Phe Trp Leu
            420                 425                 430

Met Ile Gln Ser Leu Ala Leu Ala Val Thr Arg Pro Glu Asn Thr Val
        435                 440                 445
```

<210> SEQ ID NO 11
<211> LENGTH: 536
<212> TYPE: PRT
<213> ORGANISM: Nannochloropsis gaditana
<220> FEATURE:
<221> NAME/KEY: misc_feature
<223> OTHER INFORMATION: cpSRP54

<400> SEQUENCE: 11

```
Met Thr Thr Ile Ser Thr Gln Ser Ser Gly Arg Ser Lys Gly Val Ala
1               5                   10                  15

Tyr Ala Met Met Asp Gly Ile Thr Asn Gly Leu Ile Gly Ala Leu Lys
            20                  25                  30
```

```
Ser Leu Ala Gly Gln Lys Thr Ile Ser Glu Ala Asn Ile Asp Gly Ala
        35                  40                  45

Leu Arg Asp Val Lys Arg Ala Leu Leu Asp Ala Asp Val Asn Leu Lys
    50                  55                  60

Val Thr Asn Ala Leu Leu Glu Ala Val Lys Glu Lys Ala Leu Gly Met
65                  70                  75                  80

Asp Val Thr Lys Gly Val Thr Pro Asp Gln Glu Phe Val Lys Ile Met
                85                  90                  95

Tyr Asp Glu Leu Val Asp Leu Met Gly Ala Glu Gln Ala Glu Leu Ala
            100                 105                 110

Gln Ala Ser Lys Pro Pro Thr Val Ile Leu Leu Ala Gly Leu Gln Gly
        115                 120                 125

Ala Gly Lys Thr Thr Ala Ala Ala Lys Leu Ala Leu Tyr Cys Gln Ser
    130                 135                 140

Arg Ala Glu Lys Ala Glu Ala Phe Glu Lys Ile Leu Met Val Ala Ala
145                 150                 155                 160

Asp Val Tyr Arg Pro Ala Ala Ile Asp Gln Leu Arg Thr Leu Gly Glu
                165                 170                 175

Arg Ile Asp Val Glu Val Phe Ser Met Gly Thr Asp Glu Asp Pro Ile
            180                 185                 190

Val Ile Ala Arg Lys Ala Leu Glu Lys Ala Lys Ala Gln Gly Phe Thr
        195                 200                 205

Thr Val Ile Val Asp Thr Ala Gly Arg Gln Val Ile Asp Glu Lys Leu
    210                 215                 220

Met Lys Glu Ile Lys Gly Val Lys Thr Ala Val Lys Pro Asp Glu Val
225                 230                 235                 240

Leu Leu Val Val Asp Ala Met Thr Gly Gln Glu Ala Ala Thr Val Thr
                245                 250                 255

Ala Arg Phe Asn Asp Glu Ile Gly Leu Thr Gly Ala Ile Leu Thr Lys
            260                 265                 270

Leu Asp Gly Asp Thr Arg Gly Gly Ala Ala Leu Ser Val Arg Gly Val
        275                 280                 285

Ser Gly Lys Pro Ile Lys Phe Ile Gly Val Gly Glu Thr Leu Glu Lys
    290                 295                 300

Leu Glu Pro Phe Tyr Pro Asp Arg Met Ala Ser Arg Ile Leu Gly Met
305                 310                 315                 320

Gly Asp Val Val Ser Leu Val Glu Lys Ala Gln Asp Glu Ile Asn Gln
                325                 330                 335

Asp Asp Ala Met Ala Ile Phe Lys Lys Met Met Thr Gly Thr Phe Asp
            340                 345                 350

Phe Asp Asp Phe Met Thr Gln Thr Arg Met Ile Ser Lys Met Gly Ser
        355                 360                 365

Leu Ser Gly Met Met Lys Met Ile Pro Gly Met Ala Gly Val Leu Pro
    370                 375                 380

Gly Asp Ala Met Tyr Glu Gly Glu Lys Lys Leu Phe Ala Tyr Gln Glu
385                 390                 395                 400

Met Ile Asn Val Met Glu Pro Glu Glu Arg Lys Asp Pro Lys Met Leu
                405                 410                 415

Leu Asp Asn Pro Gly Ala Asp Leu Arg Trp Lys Arg Ile Val Glu Glu
            420                 425                 430

Ser Gly Arg Ser Met Glu Glu Ala Lys Asn Phe Gln Arg Glu Phe Ser
        435                 440                 445
```

```
Asn Leu Arg Leu Met Met Thr Arg Met Ser Ser Arg Leu Ser Glu Lys
    450                 455                 460

Thr Gly Phe Asp Pro Ser Lys Gly Lys Asp Ala Ala Ile Asp Glu Ser
465                 470                 475                 480

Ala Leu Gln Glu Leu Asp Met Lys Asn Leu Ala Met Met Ser Gln Asn
                485                 490                 495

Arg Gln Ala Arg Arg Lys Leu Glu Lys Gln Ser Arg Arg Ala Gly Ser
            500                 505                 510

Asp Asp Asp Thr Pro Gln Lys Gly Phe Gly Gly Gly Gly Gly Gly Gly
        515                 520                 525

Gly Gly Lys Lys Lys Lys Lys Arg
    530                 535


<210> SEQ ID NO 12
<211> LENGTH: 486
<212> TYPE: PRT
<213> ORGANISM: Thalassiosira pseudonana
<220> FEATURE:
<221> NAME/KEY: misc_feature
<223> OTHER INFORMATION: cpSRP54

<400> SEQUENCE: 12

Met Phe Asp Gln Leu Ser Asn Ala Leu Thr Glu Val Ala Lys Asn Phe
1               5                   10                  15

Gly Gly Lys Gln Arg Met Thr Glu Asn Ser Ile Gln Pro Ala Leu Lys
            20                  25                  30

Ser Val Arg Arg Ala Leu Leu Asp Ala Asp Val Asn Leu Asp Val Ala
        35                  40                  45

Thr Ala Leu Ile Asp Gly Val Lys Arg Arg Ser Leu Gly Lys Glu Val
    50                  55                  60

Thr Lys Gly Val Thr Ala Glu Gln Gln Phe Ile Lys Ala Met Tyr Asp
65                  70                  75                  80

Glu Leu Leu Asp Met Met Gly Gly Glu Ala Asn Glu Ser Asn Thr Met
                85                  90                  95

Ala Thr Leu Ala His Ser Ser Val Ala Asn Glu Pro Ala Val Ile Leu
            100                 105                 110

Leu Ala Gly Leu Gln Gly Ala Gly Lys Thr Thr Ala Ala Gly Lys Leu
        115                 120                 125

Ala Phe Arg Leu Pro Lys Arg Asn Arg Lys Val Leu Leu Val Ala Ala
    130                 135                 140

Asp Val Tyr Arg Pro Ala Ala Ile Glu Gln Leu Gln Ile Leu Gly Lys
145                 150                 155                 160

Gln Ile Gly Val Glu Val Phe Ser Met Gly Val Asp Ala Asp Pro Ala
                165                 170                 175

Asp Ile Ala Lys Glu Ala Val Glu Lys Ala Lys Arg Glu Gly Phe Asp
            180                 185                 190

Thr Val Val Val Asp Thr Ala Gly Arg Gln Val Val Asp Glu Glu Leu
        195                 200                 205

Met Glu Glu Leu Arg Arg Val Lys Lys Thr Val Glu Pro Asp Glu Thr
    210                 215                 220

Leu Leu Val Val Asp Ala Met Thr Gly Gln Ala Ala Ala Ser Leu Thr
225                 230                 235                 240

Ala Ser Phe Asp Ala Ala Val Gly Ile Ser Gly Ala Ile Leu Thr Lys
                245                 250                 255

Leu Asp Gly Asp Ser Arg Gly Gly Ala Ala Val Ser Ile Arg Gly Val
            260                 265                 270
```

```
Ser Gly Lys Pro Ile Lys Phe Val Gly Val Gly Glu Lys Thr Asn Asp
        275                 280                 285

Leu Glu Pro Phe Tyr Pro Asp Arg Met Ala Ser Arg Ile Leu Gly Met
    290                 295                 300

Gly Asp Val Ile Ser Leu Val Glu Lys Ala Ser Met Glu Val Ser Asp
305                 310                 315                 320

Ala Asp Ala Ala Lys Met Gln Glu Lys Met Ala Lys Ala Glu Phe Asp
                325                 330                 335

Phe Asp Asp Phe Met Thr Gln Ser Arg Met Val Ser Lys Met Gly Ser
            340                 345                 350

Met Ala Gly Val Ala Lys Met Leu Pro Gly Met Gly Asn Met Ile Asp
        355                 360                 365

Ser Ser Gln Met Arg Gln Val Glu Glu Arg Ile Lys Arg Ser Glu Ala
    370                 375                 380

Met Ile Cys Ser Met Asn Lys Lys Glu Arg Ala Asn Pro Gly Leu Leu
385                 390                 395                 400

Leu Thr Asp Lys Ser Ala Arg Ser Arg Leu Met Arg Ile Thr Lys Gly
                405                 410                 415

Ser Gly Leu Ala Phe Glu Asp Gly Leu Ala Phe Met Ser Glu Phe Gln
            420                 425                 430

Lys Met Arg Thr Met Ile Ser Arg Met Ala Lys Gln Thr Gly Met Gly
        435                 440                 445

Gln Pro Asp Gly Glu Gly Glu Met Glu Pro Ala Met Ala Gly Asn Arg
    450                 455                 460

Asn Ala Arg Arg Ala Ala Lys Lys Lys Gly Lys Lys Gly Gly Arg Gly
465                 470                 475                 480

Gly Gly Met Gly Phe Ala
                485


<210> SEQ ID NO 13
<211> LENGTH: 530
<212> TYPE: PRT
<213> ORGANISM: Aureococcus anophagefferens
<220> FEATURE:
<221> NAME/KEY: misc_feature
<223> OTHER INFORMATION: cpSRP54

<400> SEQUENCE: 13

Met Thr Met Ala Arg Arg Ala Ala Thr Ala Ala Leu Val Leu Ala Ala
1               5                   10                  15

Ala Trp Ala Phe Ala Pro Pro Gln Thr Lys Arg Ala Thr Thr Gln Leu
            20                  25                  30

Tyr Phe Phe Asp Lys Leu Ala Glu Ser Ile Thr Ala Ala Thr Asp Val
        35                  40                  45

Leu Ser Gly Lys Ser Arg Met Thr Glu Ala Asn Thr Lys Ser Ala Leu
    50                  55                  60

Arg Asp Val Arg Arg Ser Leu Leu Asp Ala Asp Val Ala Lys Val Val
65                  70                  75                  80

Val Asp Gly Phe Val Glu Asn Val Gln Ala Ser Ala Leu Asp Gly Glu
                85                  90                  95

Val Ala Glu Gly Val Asp Pro Gly Gln Gln Phe Val Lys Ile Val Tyr
            100                 105                 110

Asp Glu Leu Lys Arg Val Met Gly Gly Asp Asp Asp Glu Leu Leu Phe
        115                 120                 125

Ser Asp Asp Pro Glu Ala Ala Ala Lys Ala Arg Ala Gly Leu Ala Tyr
```

```
    130                 135                 140

Arg Asp Asp Gly Ala Pro Thr Val Val Leu Leu Cys Gly Leu Gln Gly
145                 150                 155                 160

Ala Gly Lys Thr Thr Ala Ala Ala Lys Leu Ala Leu Arg Leu Lys Glu
                165                 170                 175

Glu Glu Gly Lys Thr Pro Met Leu Val Ala Ala Asp Val Tyr Arg Pro
            180                 185                 190

Ala Ala Val Glu Gln Leu Gln Ile Leu Gly Glu Gln Val Gly Val Pro
        195                 200                 205

Val Tyr Ala Glu Ala Phe Glu Ala Gly Ala Gly Asp Ala Val Ala Ile
    210                 215                 220

Ala Thr Ala Gly Val Arg Ala Ala Lys Glu Arg Gly Ala Asp Val Val
225                 230                 235                 240

Ile Val Asp Thr Ala Gly Arg Gln Val Ile Glu Glu Ser Leu Met Ala
                245                 250                 255

Glu Leu Arg Ser Val Arg Ala Ala Thr Lys Pro Asp Glu Thr Leu Leu
            260                 265                 270

Val Leu Asp Ala Met Thr Gly Gln Asp Ala Ala Ser Leu Ala Lys Arg
        275                 280                 285

Phe Asp Asp Ala Cys Pro Leu Thr Gly Ser Val Leu Thr Lys Leu Asp
    290                 295                 300

Gly Asp Ala Arg Gly Gly Ala Ala Leu Ser Val Arg Ala Val Ser Gly
305                 310                 315                 320

Lys Pro Ile Lys Phe Val Gly Val Gly Glu Lys Val Gly Asp Leu Glu
                325                 330                 335

Pro Phe Phe Pro Ala Arg Met Ala Ser Arg Ile Leu Gly Met Gly Asp
            340                 345                 350

Val Val Ser Leu Val Glu Lys Ala Ser Lys Gln Gln Ser Ala Ala Glu
        355                 360                 365

Ala Lys Ala Val Met Glu Arg Thr Lys Gln Ala Lys Phe Asn Phe Asp
    370                 375                 380

Asp Tyr Leu Asp Gln Ala Arg Met Val Ser Asn Met Gly Ser Phe Gly
385                 390                 395                 400

Ala Val Ala Lys Met Met Pro Gly Met Gly Gly Ile Asp Asn Asp Gln
                405                 410                 415

Ile Ala Ala Ala Glu Ala Lys Ile Lys Ile Gln Ala Ser Leu Ile Asn
            420                 425                 430

Ser Met Thr Pro Lys Glu Arg Gly Glu Pro Asp Leu Ile Ile Arg Asp
        435                 440                 445

Lys Ser Ala Leu Ala Arg Gln Lys Arg Ile Ala Ala Gly Ser Gly Arg
    450                 455                 460

Ser Val Asp Gln Ala Lys Gln Phe Leu Ser Glu Phe Gln Gln Met Arg
465                 470                 475                 480

Thr Met Met Ala Lys Met Ala Gly Gln Ala Pro Pro Asp Gly Ala Asp
                485                 490                 495

Ala Ala Ala Ala Pro Asp Pro Asp Ala Leu Leu Asn Arg Ala Ala Arg
            500                 505                 510

Arg Ala Lys Lys Lys Lys Gly Gly Lys Arg Lys Leu Lys Thr Ala Gly
        515                 520                 525

Phe Gly
    530
```

<210> SEQ ID NO 14

<211> LENGTH: 556
<212> TYPE: PRT
<213> ORGANISM: Ectocarpus siliculosus
<220> FEATURE:
<221> NAME/KEY: misc_feature
<223> OTHER INFORMATION: cpSRP54

<400> SEQUENCE: 14

```
Met Ile Met Ala Ser Leu Lys His Arg Ser Pro Pro Arg Gly Gly Ala
1               5                   10                  15

Ala Ala Thr Leu Ser Phe Phe Cys Cys Val Cys Ala Leu Phe Ala Gln
            20                  25                  30

Ser Ser Val Ala Phe Val Pro Ala Gly Gly Leu Ser Arg Cys Gly Val
        35                  40                  45

Asn Asp Arg Ser Ser Ser Ser Cys Arg Ala Ala Ala Ile Gly Ala Ala
    50                  55                  60

Gly Arg Ser Ser Leu Pro Val Ser Arg Ser Ser Ser Arg Arg Gly Arg
65                  70                  75                  80

Arg Gly Gly Cys Ala Gly Gly Ala Ser Ser Pro Leu Gly Met Met Phe
                85                  90                  95

Asp Thr Leu Ala Glu Asn Met Ala Gly Val Ala Asn Leu Phe Thr Gly
            100                 105                 110

Gln Lys Thr Ile Thr Glu Ser Ser Val Glu Gly Ala Leu Asn Glu Val
        115                 120                 125

Lys Arg Ala Leu Leu Asp Ala Asp Leu Asn Leu Met Val Thr Asn Thr
    130                 135                 140

Leu Val Asp Ala Val Lys Ser Lys Ala Val Gly Met Lys Leu Val Asp
145                 150                 155                 160

Gly Val Thr Ala Lys Gln Gln Phe Val Asn Val Met Asn Asp Glu Leu
                165                 170                 175

Val Glu Ile Met Gly Ala Glu Gln Ala Pro Leu Ala Arg Arg Thr Asp
            180                 185                 190

Gly Lys Pro Thr Val Ile Leu Leu Ala Gly Leu Gln Gly Thr Gly Lys
        195                 200                 205

Thr Thr Ala Ala Ala Lys Leu Ala Lys Tyr Leu Gln Gln Glu Glu Glu
    210                 215                 220

Pro Lys Lys Val Leu Leu Val Ala Gly Asp Val Tyr Arg Pro Ala Ile
225                 230                 235                 240

Asp Gln Leu Ile Ser Leu Gly Lys Arg Ile Asp Val Glu Val Phe Ser
                245                 250                 255

Met Gly Gln Gly Val Asp Pro Val Glu Ile Thr Lys Ala Gly Leu Glu
            260                 265                 270

Arg Ala Val Glu Gly Glu Phe Asp Thr Val Ile Val Asp Thr Ala Gly
        275                 280                 285

Arg Gln Val Val Asp Asp Thr Leu Met Thr Glu Leu Lys Asp Ile Gln
    290                 295                 300

Val Ala Ser Glu Ala Asp Glu Val Leu Leu Val Val Asp Ala Met Thr
305                 310                 315                 320

Gly Gln Glu Ala Ala Thr Leu Ala Ser Val Phe Asn Glu Lys Ile Gly
                325                 330                 335

Ile Thr Gly Ala Val Leu Thr Lys Met Asp Gly Asp Thr Arg Gly Gly
            340                 345                 350

Ala Ala Leu Ser Val Gln Gly Val Ser Gln Lys Pro Ile Lys Phe Val
        355                 360                 365

Gly Ile Gly Glu Lys Met Ser Glu Glu Glu Ala Ala Lys Leu Ala Lys
```

```
    370                 375                 380

Lys Met Ile Asn Ala Glu Phe Asp Phe Asn Asp Phe Leu Lys Gln Ala
385                 390                 395                 400

Lys Met Met Lys Gly Met Gly Ser Leu Gly Gly Val Ala Asn Met Ile
                405                 410                 415

Pro Gly Met Ala Gly Lys Ile Thr Pro Gln Gln Leu Asn Gln Ala Glu
            420                 425                 430

Glu Gly Val Gln Arg Ala Glu Gly Leu Ile Lys Phe Met Thr Pro Glu
        435                 440                 445

Glu Arg Arg Thr Pro Lys Leu Leu Ile Leu Asp Pro Thr Ser Gln Ala
    450                 455                 460

Arg Cys Arg Arg Ile Ala Arg Asp Ala Gly Val Lys Leu Ser Ala Val
465                 470                 475                 480

Ser Ala Phe Leu Lys Glu Phe Gln Ala Met Gln Ser Asn Met Ser Arg
                485                 490                 495

Met Gly Lys Gln Met Ala Asp Gly Asp Pro Asn Ala Gly Pro Gly Gly
            500                 505                 510

Gln Pro Ser Pro Phe Gln Gly Leu Gly Gly Asp Thr Ala Pro Gly Ala
        515                 520                 525

Ala Pro Ser Met Asn Arg Gln Gln Arg Arg Gln Ser Lys Lys Asn Lys
    530                 535                 540

Ala Gly Arg Ser Ala Ala Pro Ser Lys Gly Phe Gly
545                 550                 555


<210> SEQ ID NO 15
<211> LENGTH: 196
<212> TYPE: PRT
<213> ORGANISM: Parachlorella sp.
<220> FEATURE:
<221> NAME/KEY: misc_feature
<223> OTHER INFORMATION: GTPase domain of SEQ ID NO:2

<400> SEQUENCE: 15

Pro Gln Val Ile Leu Met Ala Gly Leu Gln Gly Thr Gly Lys Thr Thr
1               5                   10                  15

Ala Ala Gly Lys Leu Ala Leu Phe Leu Gln Lys Lys Gly Gln Lys Val
            20                  25                  30

Leu Leu Val Ala Thr Asp Ile Tyr Arg Pro Ala Ala Ile Asp Gln Leu
        35                  40                  45

Val Lys Leu Gly Asp Arg Ile Gly Val Pro Val Phe Gln Leu Gly Thr
    50                  55                  60

Gln Val Gln Pro Pro Glu Ile Ala Arg Gln Gly Leu Glu Lys Ala Arg
65                  70                  75                  80

Ala Glu Gly Phe Asp Ala Val Ile Val Asp Thr Ala Gly Arg Leu Gln
                85                  90                  95

Ile Asp Gln Ser Met Met Glu Glu Leu Val Gln Ile Lys Ser Thr Val
            100                 105                 110

Lys Pro Ser Asp Thr Leu Leu Val Val Asp Ala Met Thr Gly Gln Glu
        115                 120                 125

Ala Ala Gly Leu Val Lys Ala Phe Asn Asp Ala Val Asp Ile Thr Gly
    130                 135                 140

Ala Val Leu Thr Lys Leu Asp Gly Asp Ser Arg Gly Gly Ala Ala Leu
145                 150                 155                 160

Ser Val Arg Gln Val Ser Gly Arg Pro Ile Lys Phe Val Gly Met Gly
                165                 170                 175
```

```
Glu Gly Met Glu Ala Leu Glu Pro Phe Tyr Pro Glu Arg Met Ala Ser
            180                 185                 190

Arg Ile Leu Gly
        195


<210> SEQ ID NO 16
<211> LENGTH: 191
<212> TYPE: PRT
<213> ORGANISM: Chlamydomonas reinhardtii
<220> FEATURE:
<221> NAME/KEY: misc_feature
<223> OTHER INFORMATION: GTPase domain of SEQ ID NO:3

<400> SEQUENCE: 16

Val His Gly Ala Arg Gly Val Gly Lys Thr Thr Ala Ala Gly Lys Leu
1               5                   10                  15

Ala Leu Tyr Leu Lys Lys Ala Lys Lys Ser Cys Leu Leu Val Ala Thr
            20                  25                  30

Asp Val Tyr Arg Pro Ala Ala Ile Asp Gln Leu Val Lys Leu Gly Ala
        35                  40                  45

Ala Ile Asp Val Pro Val Phe Glu Met Gly Thr Asp Val Ser Pro Val
    50                  55                  60

Glu Ile Ala Lys Lys Gly Val Glu Glu Ala Arg Arg Leu Gly Val Asp
65                  70                  75                  80

Ala Val Ile Ile Asp Thr Ala Gly Arg Leu Gln Val Asp Glu Gly Met
                85                  90                  95

Met Ala Glu Leu Arg Asp Val Lys Ser Ala Val Arg Pro Ser Asp Thr
            100                 105                 110

Leu Leu Val Val Asp Ala Met Thr Gly Gln Glu Ala Ala Asn Leu Val
        115                 120                 125

Arg Ser Phe Asn Glu Ala Val Asp Ile Ser Gly Ala Ile Leu Thr Lys
    130                 135                 140

Met Asp Gly Asp Ser Arg Gly Gly Ala Ala Leu Ser Val Arg Glu Val
145                 150                 155                 160

Ser Gly Lys Pro Ile Lys Phe Val Gly Val Gly Glu Lys Met Glu Ala
                165                 170                 175

Leu Glu Pro Phe Tyr Pro Glu Arg Met Ala Ser Arg Ile Leu Gly
            180                 185                 190


<210> SEQ ID NO 17
<211> LENGTH: 196
<212> TYPE: PRT
<213> ORGANISM: Micromonas pusilla
<220> FEATURE:
<221> NAME/KEY: misc_feature
<223> OTHER INFORMATION: GTPase domain of SEQ ID NO:4

<400> SEQUENCE: 17

Pro Thr Val Ile Leu Met Ala Gly Leu Gln Gly Val Gly Lys Thr Thr
1               5                   10                  15

Ala Cys Gly Lys Leu Ala Leu Phe Leu Lys Ala Gln Gly Lys Gln Ser
            20                  25                  30

Leu Leu Val Ala Thr Asp Val Tyr Arg Pro Ala Ala Ile Asp Gln Leu
        35                  40                  45

Lys Lys Leu Gly Glu Gln Ile Asp Val Pro Val Phe Glu Leu Gly Thr
    50                  55                  60

Asp Phe Ser Pro Pro Asp Ile Ala Arg Ser Gly Val Glu Lys Ala Lys
65                  70                  75                  80
```

```
Leu Glu Asn Phe Asp Val Val Ile Val Asp Thr Ala Gly Arg Leu Gln
                85                  90                  95

Val Asp Glu Met Leu Met Ala Glu Leu Leu Ala Thr Lys Ala Ala Thr
            100                 105                 110

Arg Ala Asp Glu Thr Leu Leu Val Val Asp Ala Met Thr Gly Gln Glu
        115                 120                 125

Ala Ala Ser Leu Thr Ala Ala Phe Asn Asp Ala Val Gly Ile Thr Gly
    130                 135                 140

Ala Val Leu Thr Lys Met Asp Gly Asp Thr Arg Gly Gly Ala Ala Leu
145                 150                 155                 160

Ser Val Arg Glu Val Ser Gly Lys Pro Ile Lys Phe Ile Gly Ser Gly
                165                 170                 175

Glu Lys Leu Asp Ala Leu Glu Pro Phe Phe Pro Glu Arg Met Thr Thr
            180                 185                 190

Arg Ile Leu Gly
        195


<210> SEQ ID NO 18
<211> LENGTH: 196
<212> TYPE: PRT
<213> ORGANISM: Micromonas sp.
<220> FEATURE:
<221> NAME/KEY: misc_feature
<223> OTHER INFORMATION: GTPase domain of SEQ ID NO:5

<400> SEQUENCE: 18

Pro Thr Val Ile Leu Met Ala Gly Leu Gln Gly Val Gly Lys Thr Thr
1               5                   10                  15

Ala Cys Gly Lys Leu Ala Leu Tyr Leu Lys Lys Gln Gly Lys Asp Ser
            20                  25                  30

Leu Leu Val Ala Thr Asp Val Tyr Arg Pro Ala Ala Ile Glu Gln Leu
        35                  40                  45

Lys Arg Leu Gly Glu Gln Val Lys Thr Pro Val Phe Asp Met Gly Val
    50                  55                  60

Arg Val Asp Pro Pro Glu Val Ala Arg Leu Gly Leu Glu Lys Ala Arg
65                  70                  75                  80

Ala Glu Gly Ile Asp Val Val Ile Ile Asp Thr Ala Gly Arg Leu Gln
                85                  90                  95

Val Asp Val His Leu Met Glu Glu Leu Arg Ala Thr Lys Ile Ala Thr
            100                 105                 110

Ala Ala Asp Glu Ile Leu Leu Val Val Asp Ala Met Thr Gly Gln Glu
        115                 120                 125

Ala Ala Ala Leu Thr Ala Ala Phe Asp Glu Ala Val Gly Ile Thr Gly
    130                 135                 140

Ala Val Leu Thr Lys Met Asp Gly Asp Thr Arg Gly Gly Ala Ala Leu
145                 150                 155                 160

Ser Val Arg Glu Val Ser Gly Lys Pro Ile Lys Phe Thr Gly Val Gly
                165                 170                 175

Glu Lys Met Glu Ala Leu Glu Pro Phe Tyr Pro Glu Arg Met Ala Ser
            180                 185                 190

Arg Ile Leu Gly
        195


<210> SEQ ID NO 19
<211> LENGTH: 195
<212> TYPE: PRT
<213> ORGANISM: Paulinella chromatophora
```

<220> FEATURE:
<221> NAME/KEY: misc_feature
<223> OTHER INFORMATION: GTPase domain of SEQ ID NO:6

<400> SEQUENCE: 19

```
Thr Val Val Leu Met Ala Gly Leu Gln Gly Ala Gly Lys Thr Thr Ala
1               5                   10                  15

Ala Ala Lys Leu Ala Leu Tyr Leu Lys Asn Gln Gly Glu Lys Val Leu
            20                  25                  30

Met Val Ala Ala Asp Val Tyr Arg Pro Ala Ala Ile Asp Gln Leu Phe
        35                  40                  45

Val Leu Gly Lys Gln Ile Asp Val Glu Val Phe Thr Leu Asn Pro Glu
    50                  55                  60

Ser Ile Pro Glu Asp Ile Ala Ala Ala Gly Leu Gln Lys Ala Ile Arg
65                  70                  75                  80

Glu Gly Phe Asp Tyr Leu Ile Val Asp Thr Ala Gly Arg Leu Gln Ile
                85                  90                  95

Asp Thr Ala Met Met Gln Glu Met Val Arg Ile Arg Ser Ala Val Asn
            100                 105                 110

Pro Asn Glu Ile Leu Leu Val Val Asp Ser Met Ile Gly Gln Glu Ala
        115                 120                 125

Ala Glu Leu Thr Arg Ala Phe His Glu Gln Ile Gly Ile Thr Gly Ala
    130                 135                 140

Val Leu Thr Lys Leu Asp Gly Asp Ala Arg Gly Gly Ala Ala Leu Ser
145                 150                 155                 160

Ile Arg Lys Val Ser Gly Ala Pro Ile Lys Phe Ile Gly Thr Gly Glu
                165                 170                 175

Lys Val Glu Ala Leu Gln Pro Phe His Pro Glu Arg Met Ala Ser Arg
            180                 185                 190

Ile Leu Gly
        195
```

<210> SEQ ID NO 20
<211> LENGTH: 196
<212> TYPE: PRT
<213> ORGANISM: Ostreococcus lucimarinus
<220> FEATURE:
<221> NAME/KEY: misc_feature
<223> OTHER INFORMATION: GTPase domain of SEQ ID NO:7

<400> SEQUENCE: 20

```
Pro Thr Val Val Leu Met Ala Gly Leu Gln Gly Val Gly Lys Thr Thr
1               5                   10                  15

Ala Cys Gly Lys Leu Ser Leu Ala Leu Arg Lys Gln Gly Lys Ser Val
            20                  25                  30

Leu Leu Val Ala Thr Asp Val Tyr Arg Pro Ala Ala Ile Asp Gln Leu
        35                  40                  45

Lys Thr Leu Gly Lys Gln Ile Gly Val Pro Val Phe Asp Met Gly Val
    50                  55                  60

Asp Gly Asn Pro Pro Glu Ile Ala Ala Arg Gly Val Arg Lys Ala Lys
65                  70                  75                  80

Asp Glu Asp Ile Asp Val Val Ile Val Asp Thr Ala Gly Arg Leu Asn
                85                  90                  95

Ile Asp Glu Lys Leu Met Gly Glu Leu Lys Ala Thr Lys Glu Ala Thr
            100                 105                 110

Ser Ala Asp Glu Thr Leu Leu Val Val Asp Ala Met Thr Gly Gln Glu
        115                 120                 125
```

```
Ala Ala Thr Leu Thr Ala Ser Phe Asn Glu Ala Val Glu Ile Thr Gly
    130                 135                 140

Ala Ile Leu Thr Lys Met Asp Gly Asp Thr Arg Gly Gly Ala Ala Leu
145                 150                 155                 160

Ser Val Arg Glu Val Ser Gly Lys Pro Ile Lys Phe Thr Gly Val Gly
                165                 170                 175

Glu Lys Met Asp Ala Leu Glu Pro Phe Tyr Pro Glu Arg Met Thr Ser
            180                 185                 190

Arg Ile Leu Gly
        195


<210> SEQ ID NO 21
<211> LENGTH: 186
<212> TYPE: PRT
<213> ORGANISM: Ostreococcus tauri
<220> FEATURE:
<221> NAME/KEY: misc_feature
<223> OTHER INFORMATION: GTPase domain of SEQ ID NO:8

<400> SEQUENCE: 21

Pro Thr Val Ile Leu Met Ala Gly Leu Gln Gly Val Gly Lys Thr Thr
1               5                   10                  15

Ala Cys Gly Lys Leu Ser Leu Ala Met Arg Lys Gln Gly Lys Thr Val
            20                  25                  30

Leu Leu Val Ala Thr Asp Val Tyr Arg Pro Ala Ala Ile Asp Gln Leu
        35                  40                  45

Lys Thr Leu Gly Thr Gln Ile Gly Val Pro Val Phe Asp Met Gly Val
    50                  55                  60

Asp Ala Ser Pro Pro Glu Val Ala Ala Arg Gly Val Arg Lys Ala Lys
65                  70                  75                  80

Glu Glu Asp Ile Asp Val Val Ile Val Asp Thr Ala Gly Arg Leu Asn
                85                  90                  95

Ile Asp Glu Lys Leu Met Ser Glu Leu Lys Asp Thr Lys Leu Ala Thr
            100                 105                 110

Lys Ala Asp Glu Thr Leu Leu Val Val Asp Ala Met Thr Gly Gln Glu
        115                 120                 125

Ala Ala Asn Leu Thr Ala Ser Phe Gln Arg Gly Asp Gly Arg Arg Thr
    130                 135                 140

Arg Arg Gly Gly Ala Ala Leu Ser Val Ala Arg Ser Phe Arg Lys Ala
145                 150                 155                 160

His Gln Phe Thr Ala Ser Val Lys Met Asp Ala Leu Glu Pro Phe Tyr
                165                 170                 175

Pro Glu Arg Met Thr Ser Arg Ile Leu Gly
            180                 185


<210> SEQ ID NO 22
<211> LENGTH: 97
<212> TYPE: PRT
<213> ORGANISM: Volvox carteri
<220> FEATURE:
<221> NAME/KEY: misc_feature
<223> OTHER INFORMATION: GTPase domain of SEQ ID NO:9

<400> SEQUENCE: 22

Pro Gln Ile Ile Leu Met Ala Gly Leu Gln Gly Val Gly Lys Thr Thr
1               5                   10                  15

Ala Ala Gly Lys Leu Ala Leu Tyr Leu Lys Lys Ala Lys Lys Ser Cys
            20                  25                  30
```

Leu Leu Val Ala Thr Asp Val Tyr Arg Pro Ala Ala Ile Asp Gln Leu
35 40 45

Val Lys Leu Gly Ala Ala Ile Asp Val Pro Val Phe Glu Leu Gly Thr
50 55 60

Gln Val Ser Gly Lys Pro Ile Lys Phe Val Gly Val Gly Glu Lys Met
65 70 75 80

Glu Ala Leu Glu Pro Phe Tyr Pro Glu Arg Met Ala Ser Arg Ile Leu
85 90 95

Gly

<210> SEQ ID NO 23
<211> LENGTH: 195
<212> TYPE: PRT
<213> ORGANISM: Phaeodactylum tricornutum
<220> FEATURE:
<221> NAME/KEY: misc_feature
<223> OTHER INFORMATION: GTPase domain of SEQ ID NO:10

<400> SEQUENCE: 23

Pro Ala Val Ile Leu Leu Ala Gly Leu Gln Gly Ala Gly Lys Thr Thr
1 5 10 15

Ala Ala Gly Lys Leu Ala Leu Phe Leu Lys Glu Gln Arg Lys Val Leu
20 25 30

Leu Val Ala Ala Asp Ile Tyr Arg Pro Ala Ala Ile Lys Gln Leu Gln
35 40 45

Val Leu Gly Glu Ser Ile Gly Val Glu Val Phe Thr Lys Gly Thr Asp
50 55 60

Val Asp Pro Val Glu Ile Val Asn Ala Gly Ile Gln Lys Ala Arg Asp
65 70 75 80

Glu Gly Tyr Asp Thr Val Ile Val Asp Thr Ala Gly Arg Gln Val Ile
85 90 95

Asp Thr Asp Leu Met Asp Glu Leu Gln Arg Met Lys Arg Ala Ala Ser
100 105 110

Pro Gln Glu Thr Leu Leu Ile Val Asp Ala Met Thr Gly Gln Glu Ala
115 120 125

Ala Ser Leu Thr Ala Ala Phe Asp Ser Ala Ile Gly Leu Thr Gly Ala
130 135 140

Ile Leu Thr Lys Met Asp Gly Asp Ser Arg Gly Gly Ala Ala Val Ser
145 150 155 160

Val Arg Gly Val Ser Gly Lys Pro Ile Lys Phe Val Gly Thr Gly Glu
165 170 175

Lys Thr Ala Asp Leu Glu Pro Phe Tyr Pro Asp Arg Met Ala Ser Arg
180 185 190

Ile Leu Gly
195

<210> SEQ ID NO 24
<211> LENGTH: 202
<212> TYPE: PRT
<213> ORGANISM: Nannochloropsis gaditana
<220> FEATURE:
<221> NAME/KEY: misc_feature
<223> OTHER INFORMATION: GTPase domain of SEQ ID NO:11

<400> SEQUENCE: 24

Pro Thr Val Ile Leu Leu Ala Gly Leu Gln Gly Ala Gly Lys Thr Thr
1 5 10 15

```
Ala Ala Ala Lys Leu Ala Leu Tyr Cys Gln Ser Arg Ala Glu Lys Ala
            20                  25                  30

Glu Ala Phe Glu Lys Ile Leu Met Val Ala Ala Asp Val Tyr Arg Pro
        35                  40                  45

Ala Ala Ile Asp Gln Leu Arg Thr Leu Gly Glu Arg Ile Asp Val Glu
    50                  55                  60

Val Phe Ser Met Gly Thr Asp Glu Asp Pro Ile Val Ile Ala Arg Lys
65                  70                  75                  80

Ala Leu Glu Lys Ala Lys Ala Gln Gly Phe Thr Thr Val Ile Val Asp
                85                  90                  95

Thr Ala Gly Arg Gln Val Ile Asp Glu Lys Leu Met Lys Glu Ile Lys
            100                 105                 110

Gly Val Lys Thr Ala Val Lys Pro Asp Glu Val Leu Leu Val Val Asp
        115                 120                 125

Ala Met Thr Gly Gln Glu Ala Ala Thr Val Thr Ala Arg Phe Asn Asp
    130                 135                 140

Glu Ile Gly Leu Thr Gly Ala Ile Leu Thr Lys Leu Asp Gly Asp Thr
145                 150                 155                 160

Arg Gly Gly Ala Ala Leu Ser Val Arg Gly Val Ser Gly Lys Pro Ile
                165                 170                 175

Lys Phe Ile Gly Val Gly Glu Thr Leu Glu Lys Leu Glu Pro Phe Tyr
            180                 185                 190

Pro Asp Arg Met Ala Ser Arg Ile Leu Gly
        195                 200


<210> SEQ ID NO 25
<211> LENGTH: 196
<212> TYPE: PRT
<213> ORGANISM: Thalassiosira pseudonana
<220> FEATURE:
<221> NAME/KEY: misc_feature
<223> OTHER INFORMATION: GTPase domain of SEQ ID NO:12

<400> SEQUENCE: 25

Pro Ala Val Ile Leu Leu Ala Gly Leu Gln Gly Ala Gly Lys Thr Thr
1               5                   10                  15

Ala Ala Gly Lys Leu Ala Phe Arg Leu Pro Lys Arg Asn Arg Lys Val
            20                  25                  30

Leu Leu Val Ala Ala Asp Val Tyr Arg Pro Ala Ala Ile Glu Gln Leu
        35                  40                  45

Gln Ile Leu Gly Lys Gln Ile Gly Val Glu Val Phe Ser Met Gly Val
    50                  55                  60

Asp Ala Asp Pro Ala Asp Ile Ala Lys Glu Ala Val Glu Lys Ala Lys
65                  70                  75                  80

Arg Glu Gly Phe Asp Thr Val Val Val Asp Thr Ala Gly Arg Gln Val
                85                  90                  95

Val Asp Glu Glu Leu Met Glu Glu Leu Arg Arg Val Lys Lys Thr Val
            100                 105                 110

Glu Pro Asp Glu Thr Leu Leu Val Val Asp Ala Met Thr Gly Gln Ala
        115                 120                 125

Ala Ala Ser Leu Thr Ala Ser Phe Asp Ala Ala Val Gly Ile Ser Gly
    130                 135                 140

Ala Ile Leu Thr Lys Leu Asp Gly Asp Ser Arg Gly Gly Ala Ala Val
145                 150                 155                 160

Ser Ile Arg Gly Val Ser Gly Lys Pro Ile Lys Phe Val Gly Val Gly
                165                 170                 175
```

```
Glu Lys Thr Asn Asp Leu Glu Pro Phe Tyr Pro Asp Arg Met Ala Ser
            180                 185                 190

Arg Ile Leu Gly
        195


<210> SEQ ID NO 26
<211> LENGTH: 200
<212> TYPE: PRT
<213> ORGANISM: Aureococcus anophagefferens
<220> FEATURE:
<221> NAME/KEY: misc_feature
<223> OTHER INFORMATION: GTPase domain of SEQ ID NO:13

<400> SEQUENCE: 26

Pro Thr Val Val Leu Leu Cys Gly Leu Gln Gly Ala Gly Lys Thr Thr
1               5                   10                  15

Ala Ala Ala Lys Leu Ala Leu Arg Leu Lys Glu Glu Glu Gly Lys Thr
            20                  25                  30

Pro Met Leu Val Ala Ala Asp Val Tyr Arg Pro Ala Ala Val Glu Gln
        35                  40                  45

Leu Gln Ile Leu Gly Glu Gln Val Gly Val Pro Val Tyr Ala Glu Ala
    50                  55                  60

Phe Glu Ala Gly Ala Gly Asp Ala Val Ala Ile Ala Thr Ala Gly Val
65                  70                  75                  80

Arg Ala Ala Lys Glu Arg Gly Ala Asp Val Val Ile Val Asp Thr Ala
                85                  90                  95

Gly Arg Gln Val Ile Glu Glu Ser Leu Met Ala Glu Leu Arg Ser Val
            100                 105                 110

Arg Ala Ala Thr Lys Pro Asp Glu Thr Leu Leu Val Leu Asp Ala Met
        115                 120                 125

Thr Gly Gln Asp Ala Ala Ser Leu Ala Lys Arg Phe Asp Asp Ala Cys
    130                 135                 140

Pro Leu Thr Gly Ser Val Leu Thr Lys Leu Asp Gly Asp Ala Arg Gly
145                 150                 155                 160

Gly Ala Ala Leu Ser Val Arg Ala Val Ser Gly Lys Pro Ile Lys Phe
                165                 170                 175

Val Gly Val Gly Glu Lys Val Gly Asp Leu Glu Pro Phe Phe Pro Ala
            180                 185                 190

Arg Met Ala Ser Arg Ile Leu Gly
        195                 200


<210> SEQ ID NO 27
<211> LENGTH: 185
<212> TYPE: PRT
<213> ORGANISM: Ectocarpus siliculosus
<220> FEATURE:
<221> NAME/KEY: misc_feature
<223> OTHER INFORMATION: GTPase domain of SEQ ID NO:14

<400> SEQUENCE: 27

Pro Thr Val Ile Leu Leu Ala Gly Leu Gln Gly Thr Gly Lys Thr Thr
1               5                   10                  15

Ala Ala Ala Lys Leu Ala Lys Tyr Leu Gln Gln Glu Glu Glu Pro Lys
            20                  25                  30

Lys Val Leu Leu Val Ala Gly Asp Val Tyr Arg Pro Ala Ile Asp Gln
        35                  40                  45

Leu Ile Ser Leu Gly Lys Arg Ile Asp Val Glu Val Phe Ser Met Gly
    50                  55                  60
```

```
Gln Gly Val Asp Pro Val Glu Ile Thr Lys Ala Gly Leu Glu Arg Ala
65                  70                  75                  80

Val Glu Gly Glu Phe Asp Thr Val Ile Val Asp Thr Ala Gly Arg Gln
                85                  90                  95

Val Val Asp Asp Thr Leu Met Thr Glu Leu Lys Asp Ile Gln Val Ala
            100                 105                 110

Ser Glu Ala Asp Glu Val Leu Leu Val Val Asp Ala Met Thr Gly Gln
        115                 120                 125

Glu Ala Ala Thr Leu Ala Ser Val Phe Asn Glu Lys Ile Gly Ile Thr
    130                 135                 140

Gly Ala Val Leu Thr Lys Met Asp Gly Asp Thr Arg Gly Gly Ala Ala
145                 150                 155                 160

Leu Ser Val Gln Gly Val Ser Gln Lys Pro Ile Lys Phe Val Gly Ile
                165                 170                 175

Gly Glu Lys Met Ser Glu Glu Glu Ala
            180                 185


<210> SEQ ID NO 28
<211> LENGTH: 1611
<212> TYPE: DNA
<213> ORGANISM: Nannochloropsis gaditana
<220> FEATURE:
<221> NAME/KEY: misc_feature
<223> OTHER INFORMATION: cpSRP54

<400> SEQUENCE: 28

atgacaacca tttcgacgca aagctcagga cggagcaagg gcgtggccta cgccatgatg      60

gacggcatta ccaatggtct catcggggct ttgaagtctt tggcagggca aaaaaccatc     120

tcagaagcca atatcgacgg cgccctgcgc gacgtcaagc gggccctgct agacgcggac     180

gtgaacctta aggtgactaa cgccttgctg gaggcggtta aagagaaggc actcggcatg     240

gacgtgacca aaggcgtgac ccccgaccag gagttcgtca agatcatgta cgacgagctc     300

gtcgacctga tgggcgccga gcaggcggaa ctcgcgcagg ccagcaagcc ccccactgtc     360

atcctcctgg ctgggctgca gggtgccggt aaaaccacgg ctgccgccaa gcttgccctc     420

tactgccagt cccgcgccga gaaagccgag gcctttgaaa agatattgat ggtggcggcg     480

gacgtgtacc gcccggcagc catcgaccag ctccgtacgc tgggagaaag gattgacgtg     540

gaggttttct ccatgggcac tgacgaggac ccgatagtca tcgcccgcaa ggccctggag     600

aaggcgaaag cccagggctt taccaccgtc attgtcgaca ccgcgggcag gcaggtcatc     660

gacgagaagc tgatgaagga gatcaagggg gtcaaaaccg ccgtcaagcc cgacgaagtc     720

ctcctggtcg tggacgccat gacgggccaa gaggccgcca ccgtcaccgc ccgcttcaac     780

gacgaaatcg gacttaccgg ggctatcctg accaagctgg acggtgacac gcgcggtgga     840

gccgccctct ctgtccgagg tgtgagtggg aagcccatca aattcatcgg agtcggtgaa     900

acgctggaaa aactcgaacc gttctacccc gaccgcatgg ccagtcggat cctgggcatg     960

ggcgacgtgg tgtccctggt ggagaaagca caagatgaga tcaaccagga cgacgccatg    1020

gccatcttca aaaagatgat gaccggcacc ttcgatttcg atgacttcat gacccagacc    1080

cgcatgattt ccaagatggg cagcctctca ggcatgatga agatgatccc gggcatggcc    1140

ggcgtccttc ccggcgacgc catgtacgag ggcgagaaga agctcttcgc ctaccaggaa    1200

atgatcaacg tgatggagcc ggaggagcgg aaagacccga agatgcttct ggacaacccc    1260

ggcgcggacc tacgatggaa gcgcatcgtg gaagagagcg gtcggtccat ggaggaggcg    1320
```

```
aagaacttcc agcgagagtt ttcgaacctg cgtttgatga tgacgcgtat gtcaagccga   1380

ctcagcgaga agacaggctt tgaccccagc aagggcaagg acgccgccat tgacgagtcg   1440

gcgctgcagg agctagacat gaagaatctg gcgatgatga gtcagaacag gcaagcgcgg   1500

cgaaagctgg aaaaacaatc tcgtcgagca ggaagtgatg atgacacacc gcaaaaaggc   1560

tttggaggag gaggtggtgg gggaggaggc aagaagaaga aaaagcgatg a            1611
```

<210> SEQ ID NO 29
<211> LENGTH: 1689
<212> TYPE: DNA
<213> ORGANISM: Nannochloropsis gaditana
<220> FEATURE:
<221> NAME/KEY: misc_feature
<223> OTHER INFORMATION: cytoSRP54

<400> SEQUENCE: 29

```
atggtgttgc aggagctcgg tgacaagctt acgggggctc tacgccggct gcagaccacc     60

acggtcgtca acgacgacgt cctcaacgac ctgctccagg acgtatgccg tgcgttagtc    120

gaatccgatg tgaatatcaa ggtagtggcg accctaagaa agggcatcaa ggagaaagtc    180

aaccttgcag atgccccccgc tggcctgaac agacggaaaa tggtgcagcg ggcggtgatg    240

gaggaattgg tccgcctggt cgactcggga acaaagccgt accaaatgag gaagggaaag    300

tcgaacgtga tcatgtttgt gggcttgcaa ggctcgggga aaactaccac cattgccaaa    360

tacgccaact attaccagcg gaagggatgg aagacgtgca tggtgtgtgc cgataccttt    420

cgtgccggag ccttcgatca gctgaagcag aatgcgacaa aactccgtgt gccttttttac    480

ggctcctaca cggaggcgga cccggtacgg atcgccgagg agggcgtcca gcagttccgt    540

tcagagggat acgaggttat cattgtcgat acctcgggcc ggcacaagca ggaagaagcc    600

ctgtttgagg agatgaaaga gatccaagcg gcggtccgtc ccgacaacgt ggtgtacgtc    660

atggacgcca cccagggcca agccgtcttc gaccaggcac agggtttcca ccaggccgcc    720

gcggtgggct ccgtcattgt caccaagctg gacgggcacg ccaagggggg aggcgccttg    780

tcggccgtgg cggcgacggg ggcgcctatc atatttttgg gctcggggga gcattttgac    840

gacctggacg tcttcaaccc cgggagtttc atcagtcggt tgctgggctt gggggacatg    900

cggggttttt tggaggaagt gagcagcctg ggggcgaggg aaggagggaa agagaggcag    960

gaggccatgg cccagcggct cgtcaagggc cagttcaccc tccgcgacat gtacgagcag   1020

tttgagaacg tgatgaagct ggggcccctt tccaaggtca tgggcatgct gccgggcttt   1080

ccctcttttc tgatgggggg gggggaagga gggagggggg ggcaggacga agctgccacg   1140

ggccggctga agcgtttctt gaccatgatg gacagcatga cggacgcgga gctcgatggg   1200

aaggtggacc tgaacaagag cgagagccgc gtgaaccgga ttgctcgagg aagcggggca   1260

cacccgatgg aagtccaatt tttgctcaag acgtacgcgc aattctcgca aatgttcaag   1320

aagatgggcc cgatgatgtt gaaaggcggg gagggtggca tacagcggca gatggcacgc   1380

aacccgggag gcgtgatgaa tcagttgagc aaggcggtgg acccgcgaat gctacagcag   1440

atgggaggcg caaaaggaat gatggacatg atgaaagcga tgggaggagg aatggggggg   1500

gggcttgcgg acatgctgca gaacttgggg ggaggggggg gagggagagg gggaggaaga   1560

gggagtggac gaggaggggg tgggatggat ccagaacaga tgcaggcgca gatggcgcaa   1620

atggaagaga tgatgaaaag tatgggaatg ggtggaggag ggaaaggagg tggagggttc   1680

cctttctga                                                           1689
```

<210> SEQ ID NO 30
<211> LENGTH: 562
<212> TYPE: PRT
<213> ORGANISM: Nannochloropsis gaditana
<220> FEATURE:
<221> NAME/KEY: misc_feature
<223> OTHER INFORMATION: cytoSRP54

<400> SEQUENCE: 30

```
Met Val Leu Gln Glu Leu Gly Asp Lys Leu Thr Gly Ala Leu Arg Arg
1               5                   10                  15

Leu Gln Thr Thr Thr Val Val Asn Asp Asp Val Leu Asn Asp Leu Leu
            20                  25                  30

Gln Asp Val Cys Arg Ala Leu Val Glu Ser Asp Val Asn Ile Lys Val
        35                  40                  45

Val Ala Thr Leu Arg Lys Gly Ile Lys Glu Lys Val Asn Leu Ala Asp
    50                  55                  60

Ala Pro Ala Gly Leu Asn Arg Arg Lys Met Val Gln Arg Ala Val Met
65                  70                  75                  80

Glu Glu Leu Val Arg Leu Val Asp Ser Gly Thr Lys Pro Tyr Gln Met
                85                  90                  95

Arg Lys Gly Lys Ser Asn Val Ile Met Phe Val Gly Leu Gln Gly Ser
            100                 105                 110

Gly Lys Thr Thr Thr Ile Ala Lys Tyr Ala Asn Tyr Tyr Gln Arg Lys
        115                 120                 125

Gly Trp Lys Thr Cys Met Val Cys Ala Asp Thr Phe Arg Ala Gly Ala
    130                 135                 140

Phe Asp Gln Leu Lys Gln Asn Ala Thr Lys Leu Arg Val Pro Phe Tyr
145                 150                 155                 160

Gly Ser Tyr Thr Glu Ala Asp Pro Val Arg Ile Ala Glu Glu Gly Val
                165                 170                 175

Gln Gln Phe Arg Ser Glu Gly Tyr Glu Val Ile Ile Val Asp Thr Ser
            180                 185                 190

Gly Arg His Lys Gln Glu Glu Ala Leu Phe Glu Glu Met Lys Glu Ile
        195                 200                 205

Gln Ala Ala Val Arg Pro Asp Asn Val Val Tyr Val Met Asp Ala Thr
    210                 215                 220

Gln Gly Gln Ala Val Phe Asp Gln Ala Gln Gly Phe His Gln Ala Ala
225                 230                 235                 240

Ala Val Gly Ser Val Ile Val Thr Lys Leu Asp Gly His Ala Lys Gly
                245                 250                 255

Gly Gly Ala Leu Ser Ala Val Ala Ala Thr Gly Ala Pro Ile Ile Phe
            260                 265                 270

Leu Gly Ser Gly Glu His Phe Asp Asp Leu Asp Val Phe Asn Pro Gly
        275                 280                 285

Ser Phe Ile Ser Arg Leu Leu Gly Leu Gly Asp Met Arg Gly Phe Leu
    290                 295                 300

Glu Glu Val Ser Ser Leu Gly Ala Arg Glu Gly Gly Lys Glu Arg Gln
305                 310                 315                 320

Glu Ala Met Ala Gln Arg Leu Val Lys Gly Gln Phe Thr Leu Arg Asp
                325                 330                 335

Met Tyr Glu Gln Phe Glu Asn Val Met Lys Leu Gly Pro Leu Ser Lys
            340                 345                 350

Val Met Gly Met Leu Pro Gly Phe Pro Ser Phe Leu Met Gly Gly Gly
```

```
        355                 360                 365

Glu Gly Gly Arg Gly Gly Gln Asp Glu Ala Ala Thr Gly Arg Leu Lys
    370                 375                 380

Arg Phe Leu Thr Met Met Asp Ser Met Thr Asp Ala Glu Leu Asp Gly
385                 390                 395                 400

Lys Val Asp Leu Asn Lys Ser Glu Ser Arg Val Asn Arg Ile Ala Arg
                405                 410                 415

Gly Ser Gly Ala His Pro Met Glu Val Gln Phe Leu Leu Lys Thr Tyr
            420                 425                 430

Ala Gln Phe Ser Gln Met Phe Lys Lys Met Gly Pro Met Met Leu Lys
        435                 440                 445

Gly Gly Glu Gly Gly Ile Gln Arg Gln Met Ala Arg Asn Pro Gly Gly
    450                 455                 460

Val Met Asn Gln Leu Ser Lys Ala Val Asp Pro Arg Met Leu Gln Gln
465                 470                 475                 480

Met Gly Gly Ala Lys Gly Met Met Asp Met Met Lys Ala Met Gly Gly
                485                 490                 495

Gly Met Gly Gly Gly Leu Ala Asp Met Leu Gln Asn Leu Gly Gly Gly
            500                 505                 510

Gly Gly Gly Arg Gly Gly Gly Arg Gly Ser Gly Arg Gly Gly Gly Gly
        515                 520                 525

Met Asp Pro Glu Gln Met Gln Ala Gln Met Ala Gln Met Glu Glu Met
    530                 535                 540

Met Lys Ser Met Gly Met Gly Gly Gly Gly Lys Gly Gly Gly Gly Phe
545                 550                 555                 560

Pro Phe
```

<210> SEQ ID NO 31
<211> LENGTH: 11263
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Construct pSGE-6206 for expressing Cas9

<400> SEQUENCE: 31

```
gcggccgccg tatggtcgac ggttgctcgg atgggggggg cggggagcga tggagggagg      60

aagatcaggt aaggtctcga cagactagag aagcacgagt gcaggtataa gaaacagcaa     120

aaaaaagtaa tgggcccagg cctggagagg gtatttgtct tgtttttctt tggccaggaa     180

cttgttctcc tttcttcgtt tctaggaccc cgatccccgc tcgcatttct ctcttcctca     240

gccgaagcgc agcggtaaag catccatttt atcccaccga aagggcgctc ccagccttcg     300

tcgagcggaa ccggggttac agtgcctcaa ccctcccaga cgtagccaga gggaagcaac     360

tccctgatgc caaccgctgt gggctgccca tcggaatctt tgacaattgc cttgatcccc     420

gggtgcaagt caagcagcac ctgccgacat cgcccgcacg gagacagaat gccgcggttt     480

tcgttcccga tggccactat gcacgtcaga tttccggcag cagccgcagc ggccgttccg     540

aggaccacga gctccgcgca tggccctccg gtgaaatgat atacattcac gccggtaaag     600

atccgaccgt cggacgagag ggctgcactg gccaccgagt agtcctcgct aataggtatg     660

ctgttgatgg tcgcagttgc acgttcgatc agcgtggatt cctcttggga taaaggcttg     720

gccatcgagc tcggtacccg gggatccatg attgttgtat tatgtaccta tgtttgtgat     780
```

```
gagacaataa atatgagaag agaacgttgc ggccactttt ttctccttcc ttcgcgtgct    840
catgttggtg gtttgggagg cagaagatgc atggagcgcc acacattcgg taggacgaaa    900
cagcctcccc cacaaaggga ccatgggtag ctaggatgac gcacaagcga gttcccgctc    960
tcgaagggaa acccaggcat ttccttcctc ttttcaagcc acttgttcac gtgtcaacac   1020
aattttggac taaaatgccc ctcggaactc ggcaggcctc cctctgctcc gttgtcctgg   1080
tcgccgagaa cgcgagaccg tgccgcatgc catcgatctg ctcgtctgta ctactaatcg   1140
tgtgcgtgtt cgtgcttgtt tcgcacgaaa ttgtcctcgt tcggccctca caacggtgga   1200
aatcggtgct agaataaagt gaggtggctt atttcaatgg cggccgtcat catgcgggat   1260
caactgaagt acggcgggtt ctcgagattt catcgtgctc gtccagagca ggtgttttgc   1320
ctgcagctct tcatgtttag ggtcatgat ttcatctgat atgccgtaag aaaaccaata   1380
ttcacttctc aattttccat ggaaaggtga aggcctaggt tgtgtgcgag gcaacgactg   1440
gggagggatc gcaacattct tgctaacctc ccctctatct tggccgctgt gaatcggcat   1500
atttaccggg ctgaattgag aaagtgtttt gagggaatta aaaggtggct gtcttgcaag   1560
cttggcttca gtgcctgctt aattcgaacc gatccagctt gtgatgaggc cttcctaagc   1620
ctggtagtca gaagcgacat ggcgctataa atttcgtctc agttggagag tagaaaagca   1680
tgattcgaac acggttttca actgccaaag atatctccat tgtttccttc aatctgtaca   1740
cctgcacggt gcaccagttg gtacggcata ttatggttta ataagcatac atcatatgaa   1800
tacaattcag cttaaattta tcatacaaag atgtaagtgc agcgtgggtc tgtaacgatc   1860
gggcgtaatt taagataatg cgagggaccg gggaggttt tggaacggaa tgaggaatgg   1920
gtcatggccc ataataataa tatgggtttg gtcgcctcgc acagcaaccg tacgtgcgaa   1980
aaaggaacag atccatttaa taagttgaac gttattcttt cctatgcaat gcgtgtatcg   2040
gaggcgagag caagtcatag gtggctgcgc acaataattg agtctcagct gagcgccgtc   2100
cgcgggtggt gtgagtggtc atcctcctcc cggcctatcg ctcacatcgc ctctcaatgg   2160
tggtggtggg gcctgatatg acctcaatgc cgacccatat taaaacccag taaagcattc   2220
accaacgaac gaggggctct tttgtgtgtg ttttgagtat gattttacac ctctttgtgc   2280
atctctctgg tcttccttgg ttcccgtagt ttgggcatca tcactcacgc ttccctcgac   2340
cttcgttctt cctttacaac cccgacacag gtcagagttg gagtaatcaa aaaaggggtg   2400
cacgaatgag atacattaga ttttgacaga tatcctttta ctggagaggg ttcaagggat   2460
caaatgaaca gcgggcgttg gcaatctagg gagggatcgg aggttggcag cgagcgaaag   2520
cgtgtccatc cttttggctg tcacacctca cgaaccaact gttagcaggc cagcacagat   2580
gacatacgag aatctttatt atatcgtaga ccttatgtgg atgacctttg gtgctgtgtg   2640
tctggcaatg aacctgaagg cttgataggg aggtggctcc cgtaaaccct ttgtcctttc   2700
cacgctgagt ctcccccgca ctgtccttta tacaaattgt tacagtcatc tgcaggcggt   2760
ttttctttgg caggcaaaga tgcccaagaa aaagcggaag gtcggcgact acaaggatga   2820
cgatgacaag ttggagcctg gagagaagcc ctacaaatgc cctgagtgcg gaaagagctt   2880
cagccaatct ggagccttga cccggcatca acgaacgcat acacgagaca agaagtactc   2940
catcgggctg gacatcggga cgaactccgt gggatgggcc gtgatcacag acgaatacaa   3000
ggtgccttcc aagaagttca aggtgctggg gaacacggac agacactcca tcaagaagaa   3060
cctcatcggg gccttgctct tcgactccgg agaaaccgcc gaagcaacgc gattgaaaag   3120
aaccgccaga agacgataca cacgacggaa gaaccgcatc tgctacctcc aggagatctt   3180
```

```
cagcaacgag atggccaagg tggacgactc gttctttcat cgcctggagg agagcttcct   3240
ggtggaggaa gacaagaaac atgagcgcca cccgatcttc gggaacatcg tggacgaagt   3300
ggcctaccac gagaaatacc ccacgatcta ccacttgcgc aagaaactcg tggactccac   3360
ggacaaagcg gacttgcggt tgatctactt ggccttggcc cacatgatca aatttcgggg   3420
ccacttcctg atcgagggcg acttgaatcc cgacaattcc gacgtggaca agctcttcat   3480
ccagctggtg cagacctaca accagctctt cgaggagaac cccatcaatg cctccggagt   3540
ggacgccaaa gccatcttgt ccgcccgatt gtccaaatcc agacgcttgg agaacttgat   3600
cgcacaactt cctggcgaga agaagaacgg cctcttcggc aacttgatcg cgctgtcgct   3660
gggattgacg cctaacttca agtccaactt cgacttggcc gaggacgcca agttgcaact   3720
gtccaaggac acctacgacg acgacctcga caacctgctg gcccaaattg gcgaccaata   3780
cgcggacttg tttttggcgg ccaagaactt gagcgacgcc atcttgttga gcgacatctt   3840
gcgcgtgaat acggagatca ccaaagcccc tttgtccgcc tctatgatca agcggtacga   3900
cgagcaccac caagacttga ccctgttgaa agccctcgtg cggcaacaat tgcccgagaa   3960
gtacaaggag atcttcttcg accagtccaa gaacgggtac gccggctaca tcgacggagg   4020
agcctcccaa gaagagttct acaagttcat caagcccatc ctggagaaga tggacggcac   4080
cgaggagttg ctcgtgaagc tgaaccgcga agacttgttg cgaaaacagc ggacgttcga   4140
caatggcagc atccccccacc aaatccattt gggagagttg cacgccatct tgcgacggca   4200
agaggacttc tacccgttcc tgaaggacaa ccgcgagaaa atcgagaaga tcctgacgtt   4260
cagaatcccc tactacgtgg gacccttggc ccgaggcaat tcccggtttg catggatgac   4320
gcgcaaaagc gaagagacga tcaccccctg gaacttcgaa gaagtggtcg acaaaggagc   4380
atccgcacag agcttcatcg agcgaatgac gaacttcgac aagaacctgc ccaacgagaa   4440
ggtgttgccc aagcattcgc tgctgtacga gtacttcacg gtgtacaacg agctgaccaa   4500
ggtgaagtac gtgaccgagg gcatgcgcaa acccgcgttc ctgtcgggag agcaaaagaa   4560
ggccattgtg gacctgctgt tcaagaccaa ccggaaggtg accgtgaaac agctgaaaga   4620
ggactacttc aagaagatcg agtgcttcga ctccgtggag atctccggcg tggaggaccg   4680
attcaatgcc tccttgggaa cctaccatga cctcctgaag atcatcaagg acaaggactt   4740
cctggacaac gaggagaacg aggacatcct ggaggacatc gtgctgaccc tgaccctgtt   4800
cgaggaccga gagatgatcg aggaacggtt gaaaacgtac gcccacttgt tcgacgacaa   4860
ggtgatgaag cagctgaaac gccgccgcta caccggatgg ggacgattga gccgcaaact   4920
gattaatgga attcgcgaca agcaatccgg aaagaccatc ctggacttcc tgaagtccga   4980
cgggttcgcc aaccgcaact tcatgcagct catccacgac gactccttga ccttcaagga   5040
ggacatccag aaggcccaag tgtccggaca aggagactcc ttgcacgagc acatcgccaa   5100
tttggccgga tcccccgcaa tcaaaaaagg catcttgcaa accgtgaaag tggtcgacga   5160
actggtgaag gtgatgggac ggcacaagcc cgagaacatc gtgatcgaaa tggcccgcga   5220
gaaccaaacc acccaaaaag gacagaagaa ctcccgagag cgcatgaagc ggatcgaaga   5280
gggcatcaag gagttgggct cccagatcct gaaggagcat cccgtggaga atacccaatt   5340
gcaaaacgag aagctctacc tctactacct ccagaacggg cgggacatgt acgtcgacca   5400
agagctggac atcaaccgcc tctccgacta cgatgtggat catattgtgc cccagagctt   5460
cctcaaggac gacagcatcg acaacaaggt cctgacgcgc agcgacaaga accggggcaa   5520
```

```
gtctgacaat gtgccttccg aagaagtcgt gaagaagatg aagaactact ggcggcagct   5580
gctcaacgcc aagctcatca cccaacggaa gttcgacaac ctgaccaagg ccgagagagg   5640
aggattgtcc gagttggaca aagccggctt cattaaacgc caactcgtgg agacccgcca   5700
gatcacgaag cacgtggccc aaatcttgga ctcccggatg aacacgaaat acgacgagaa   5760
tgacaagctg atccgcgagg tgaaggtgat cacgctgaag tccaagctgg tgagcgactt   5820
ccggaaggac ttccagttct acaaggtgcg ggagatcaac aactaccatc acgcccatga   5880
cgcctacctg aacgccgtgg tcggaaccgc cctgatcaag aaatacccca agctggagtc   5940
cgaattcgtg tacggagatt acaaggtcta cgacgtgcgg aagatgatcg cgaagtccga   6000
gcaggagatc ggcaaagcca ccgccaagta cttcttttac tccaacatca tgaacttctt   6060
caagaccgag atcacgctcg ccaacggcga gatccgcaag cgccccctga tcgagaccaa   6120
cggcgagacg ggagagattg tgtgggacaa aggaagagat tttgccacag tgcgcaaggt   6180
gctgtccatg cctcaggtga acatcgtgaa gaagaccgag gtgcaaacag gagggttttc   6240
caaagagtcc attttgccta agaggaattc cgacaagctc atcgcccgca agaaggactg   6300
ggaccccaag aagtacgggg gcttcgactc ccccacggtg gcctactccg tgttggtggt   6360
ggccaaagtg gagaaaggga agagcaagaa gctgaaatcc gtgaaggagt tgctcggaat   6420
cacgatcatg gaacgatcgt cgttcgagaa aaaccccatc gacttcctcg aagccaaagg   6480
gtacaaagag gtgaagaagg acctgatcat caagctgccc aagtactccc tgttcgagct   6540
ggagaacggc cgcaagcgga tgctggcctc cgccggggaa ctgcagaaag ggaacgaatt   6600
ggccttgccc tccaaatacg tgaacttcct ctacttggcc tcccattacg aaaagctcaa   6660
aggatcccct gaggacaatg agcagaagca actcttcgtg gaacaacaca agcactacct   6720
ggacgagatc atcgagcaga tcagcgagtt ctccaagcgc gtgatcctcg ccgacgccaa   6780
cctggacaag gtgctctccg cctacaacaa gcaccgcgac aagcctatcc gcgagcaagc   6840
cgagaatatc attcacctgt ttaccctgac gaatttggga gcccctgccg cctttaaata   6900
ctttgacacc accatcgacc gcaaaagata cacctccacc aaggaagtct tggacgccac   6960
cctcatccac cagtccatca cgggcctcta cgagacgcgc atcgacctct cccaattggg   7020
cggcgactaa agtgatgcgg cctttaggaa acaccacaaa agtaattgac aatctcagga   7080
acgatctgcg tgtttacagc ttcccaaata acaattatac cacgtaccaa aaggggttta   7140
atgtatctca caaattcttc taataggtac agcttctcaa attgggtgta tgatgtgaca   7200
cttcgtctca cacacgtcac gataattcag cgtatggctt cccttcatca cattcacgca   7260
aacttctaca caaccctggg catatttctt gtgttggcaa cactcccgaa atcgattctg   7320
cacacaatgg ttcattcaat gattcaagta cgttttagac ggactaggca gtttaattaa   7380
aaacatctat cctccagatc accagggcca gtgaggccgg cataaaggac ggcaaggaaa   7440
gaaaagaaag aaagaaaagg acacttatag catagtttga agttataagt agtcgcaatc   7500
tgtgtgcagc cgacagatgc tttttttttc cgtttggcag gaggtgtagg gatgtcgaag   7560
accagtccag ctagtatcta tcctacaagt caatcatgct gcgacaaaaa tttctcgcac   7620
gaggcctctc gataaacaaa actttaaaag cacacttcat tgtcatgcag agtaataact   7680
cttccgcgtc gatcaattta tcaatctcta tcatttccgc ccctttcctt gcatagagca   7740
agaaaagcga cccggatgag gataacatgt cctgcgccag tagtgtggca ttgcctgtct   7800
ctcatttaca cgtactgaaa gcataatgca cgcgcatacc aatatttttc gtgtacggag   7860
atgaagagac gcgacacgta agatcacgag aaggcgagca cggttgccaa tggcagacgc   7920
```

```
gctagtctcc attatcgcgt tgttcggtag cttgctgcat gtcttcagtg gcactatatc   7980
cactctgcct cgtcttctac acgagggcca catcggtgca agttcgaaaa atcatatctc   8040
aatcttcaga tcctttccag aaacggtgct caggcgggaa agtgaaggtt ttctactcta   8100
gtggctaccc caattctctc cgactgtcgc agacggtcct tcgttgcgca cgcaccgcgc   8160
actacctctg aaattcgaca accgaagttc aattttacat ctaacttctt tcccattctc   8220
tcaccaaaag cctagcttac atgttggaga gcgacgagag cggcctgccc gccatggaga   8280
tcgagtgccg catcaccggc accctgaacg gcgtggagtt cgagctggtg ggcggcggag   8340
agggcacccc cgagcagggc cgcatgacca acaagatgaa gagcaccaaa ggcgccctga   8400
ccttcagccc ctacctgctg agccacgtga tgggctacgg cttctaccac ttcggcacct   8460
accccagcgg ctacgagaac cccttcctgc acgccatcaa caacggcggc tacaccaaca   8520
cccgcatcga gaagtacgag gacggcggcg tgctgcacgt gagcttcagc taccgctacg   8580
aggccggccg cgtgatcggc gacttcaagg tgatgggcac cggcttcccc gaggacagcg   8640
tgatcttcac cgacaagatc atccgcagca acgccaccgt ggagcacctg caccccatgg   8700
gcgataacga tctggatggc agcttcaccc gcaccttcag cctgcgcgac ggcggctact   8760
acagctccgt ggtggacagc cacatgcact tcaagagcgc catccacccc agcatcctgc   8820
agaacggggg ccccatgttc gccttccgcc gcgtggagga ggatcacagc aacaccgagc   8880
tgggcatcgt ggagtaccag cacgccttca agaccccgga tgcagatgcc ggtgaagaat   8940
aagggtggga aggagtcggg gagggtcctg gcagagcggc gtcctcatga tgtgttggag   9000
acctggagag tcgagagctt cctcgtcacc tgattgtcat gtgtgtatag gttaaggggg   9060
cccactcaaa gccataaaga cgaacacaaa cactaatctc aacaaagtct actagcatgc   9120
cgtctgtcca tctttatttc ctggcgcgcc tatgcttgta aaccgttttg tgaaaaaatt   9180
tttaaaataa aaaaggggac ctctagggtc cccaattaat tagtaatata atctattaaa   9240
ggtcattcaa aaggtcatcc agacgaaagg gcctcgtgat acgcctattt ttataggtta   9300
atgtcatgat aataatggtt tcttagacgt caggtggcac ttttcgggga aatgtgcgcg   9360
gaacccctat ttgtttattt ttctaaatac attcaaatat gtatccgctc atgagacaat   9420
aaccctgata aatgcttcaa taatattgaa aaaggaagag tatgagtatt caacatttcc   9480
gtgtcgccct tattcccttt tttgcggcat tttgccttcc tgtttttgct cacccagaaa   9540
cgctggtgaa agtaaaagat gctgaagatc agttgggtgc acgagtgggt tacatcgaac   9600
tggatctcaa cagcggtaag atccttgaga gttttcgccc cgaagaacgt tttccaatga   9660
tgagcacttt taaagttctg ctatgtggcg cggtattatc ccgtattgac gccgggcaag   9720
agcaactcgg tcgccgcata cactattctc agaatgactt ggttgagtac tcaccagtca   9780
cagaaaagca tcttacggat ggcatgacag taagagaatt atgcagtgct gccataacca   9840
tgagtgataa cactgcggcc aacttacttc tgacaacgat cggaggaccg aaggagctaa   9900
ccgctttttt gcacaacatg ggggatcatg taactcgcct tgatcgttgg gaaccggagc   9960
tgaatgaagc cataccaaac gacgagcgtg acaccacgat gcctgtagca atggcaacaa  10020
cgttgcgcaa actattaact ggcgaactac ttactctagc ttcccggcaa caattaatag  10080
actggatgga ggcggataaa gttgcaggac cacttctgcg ctcggccctt ccggctggct  10140
ggtttattgc tgataaatct ggagccggtg agcgtgggtc tcgcggtatc attgcagcac  10200
tggggccaga tggtaagccc tcccgtatcg tagttatcta cacgacgggg agtcaggcaa  10260
```

```
ctatggatga acgaaataga cagatcgctg agataggtgc ctcactgatt aagcattggt  10320

aactgtcaga ccaagtttac tcatatatac tttagattga tttaaaactt catttttaat  10380

ttaaaaggat ctaggtgaag atcctttttg ataatctcat gaccaaaatc ccttaacgtg  10440

agttttcgtt ccactgagcg tcagaccccg tagaaaagat caaaggatct tcttgagatc  10500

cttttttttct gcgcgtaatc tgctgcttgc aaacaaaaaa accaccgcta ccagcggtgg  10560

tttgtttgcc ggatcaagag ctaccaactc tttttccgaa ggtaactggc ttcagcagag  10620

cgcagatacc aaatactgtc cttctagtgt agccgtagtt aggccaccac ttcaagaact  10680

ctgtagcacc gcctacatac ctcgctctgc taatcctgtt accagtggct gctgccagtg  10740

gcgataagtc gtgtcttacc gggttggact caagacgata gttaccggat aaggcgcagc  10800

ggtcgggctg aacggggggt tcgtgcacac agcccagctt ggagcgaacg acctacaccg  10860

aactgagata cctacagcgt gagctatgag aaagcgccac gcttcccgaa gggagaaagg  10920

cggacaggta tccggtaagc ggcagggtcg gaacaggaga gcgcacgagg gagcttccag  10980

ggggaaacgc ctggtatctt tatagtcctg tcgggtttcg ccacctctga cttgagcgtc  11040

gatttttgtg atgctcgtca ggggggcgga gcctatggaa aaacgccagc aacgcggcct  11100

ttttacggtt cctggccttt tgctggcctt ttgctcacat gttctttcct gcgttatccc  11160

ctgattctgt ggataaccgt attaccgcct ttgagtgagc tgataccgct cgccgcagcc  11220

gaacgaccga gcgcagcgag tcagtgagcg aggaagcgga aga                    11263
```

<210> SEQ ID NO 32
<211> LENGTH: 4101
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 gene codon-optimized for Nannochloropsis

<400> SEQUENCE: 32

```
gacaagaagt actccatcgg gctggacatc gggacgaact ccgtgggatg ggccgtgatc     60

acagacgaat acaaggtgcc ttccaagaag ttcaaggtgc tggggaacac ggacagacac    120

tccatcaaga agaacctcat cggggccttg ctcttcgact ccggagaaac cgccgaagca    180

acgcgattga aaagaaccgc cagaagacga tacacacgac ggaagaaccg catctgctac    240

ctccaggaga tcttcagcaa cgagatggcc aaggtggacg actcgttctt tcatcgcctg    300

gaggagagct tcctggtgga ggaagacaag aaacatgagc gccacccgat cttcgggaac    360

atcgtggacg aagtggccta ccacgagaaa taccccacga tctaccactt gcgcaagaaa    420

ctcgtggact ccacggacaa agcggacttg cggttgatct acttggcctt ggcccacatg    480

atcaaatttc ggggccactt cctgatcgag ggcgacttga atcccgacaa ttccgacgtg    540

gacaagctct tcatccagct ggtgcagacc tacaaccagc tcttcgagga gaaccccatc    600

aatgcctccg gagtggacgc caaagccatc ttgtccgccc gattgtccaa atccagacgc    660

ttggagaact tgatcgcaca acttcctggc gagaagaaga acggcctctt cggcaacttg    720

atcgcgctgt cgctgggatt gacgcctaac ttcaagtcca acttcgactt ggccgaggac    780

gccaagttgc aactgtccaa ggacacctac gacgacgacc tcgacaacct gctggcccaa    840

attggcgacc aatacgcgga cttgtttttg gcggccaaga acttgagcga cgccatcttg    900

ttgagcgaca tcttgcgcgt gaatacggag atcaccaaag ccccttttgtc cgcctctatg    960
```

-continued

```
atcaagcggt acgacgagca ccaccaagac ttgaccctgt tgaaagccct cgtgcggcaa   1020
caattgcccg agaagtacaa ggagatcttc ttcgaccagt ccaagaacgg gtacgccggc   1080
tacatcgacg gaggagcctc ccaagaagag ttctacaagt tcatcaagcc catcctggag   1140
aagatggacg gcaccgagga gttgctcgtg aagctgaacc gcgaagactt gttgcgaaaa   1200
cagcggacgt tcgacaatgg cagcatcccc caccaaatcc atttgggaga gttgcacgcc   1260
atcttgcgac ggcaagagga cttctacccg ttcctgaagg acaaccgcga gaaaatcgag   1320
aagatcctga cgttcagaat cccctactac gtgggaccct tggcccgagg caattcccgg   1380
tttgcatgga tgacgcgcaa aagcgaagag acgatcaccc cctggaactt cgaagaagtg   1440
gtcgacaaag gagcatccgc acagagcttc atcgagcgaa tgacgaactt cgacaagaac   1500
ctgcccaacg agaaggtgtt gcccaagcat tcgctgctgt acgagtactt cacggtgtac   1560
aacgagctga ccaaggtgaa gtacgtgacc gagggcatgc gcaaacccgc gttcctgtcg   1620
ggagagcaaa agaaggccat tgtggacctg ctgttcaaga ccaaccggaa ggtgaccgtg   1680
aaacagctga aagaggacta cttcaagaag atcgagtgct tcgactccgt ggagatctcc   1740
ggcgtggagg accgattcaa tgcctccttg ggaacctacc atgacctcct gaagatcatc   1800
aaggacaagg acttcctgga caacgaggag aacgaggaca tcctggagga catcgtgctg   1860
accctgaccc tgttcgagga ccgagagatg atcgaggaac ggttgaaaac gtacgcccac   1920
ttgttcgacg acaaggtgat gaagcagctg aaacgccgcc gctacaccgg atggggacga   1980
ttgagccgca aactgattaa tggaattcgc gacaagcaat ccggaaagac catcctggac   2040
ttcctgaagt ccgacgggtt cgccaaccgc aacttcatgc agctcatcca cgacgactcc   2100
ttgaccttca aggaggacat ccagaaggcc caagtgtccg gacaaggaga ctccttgcac   2160
gagcacatcg ccaatttggc cggatccccc gcaatcaaaa aaggcatctt gcaaaccgtg   2220
aaagtggtcg acgaactggt gaaggtgatg ggacggcaca agcccgagaa catcgtgatc   2280
gaaatggccc gcgagaacca aaccacccaa aaaggacaga agaactcccg agagcgcatg   2340
aagcggatcg aagagggcat caaggagttg ggctcccaga tcctgaagga gcatcccgtg   2400
gagaataccc aattgcaaaa cgagaagctc tacctctact acctccagaa cgggcgggac   2460
atgtacgtcg accaagagct ggacatcaac cgcctctccg actacgatgt ggatcatatt   2520
gtgccccaga gcttcctcaa ggacgacagc atcgacaaca aggtcctgac gcgcagcgac   2580
aagaaccggg gcaagtctga caatgtgcct tccgaagaag tcgtgaagaa gatgaagaac   2640
tactggcggc agctgctcaa cgccaagctc atcacccaac ggaagttcga caacctgacc   2700
aaggccgaga gaggaggatt gtccgagttg gacaaagccg gcttcattaa acgccaactc   2760
gtggagaccc gccagatcac gaagcacgtg gcccaaatct tggactcccg gatgaacacg   2820
aaatacgacg agaatgacaa gctgatccgc gaggtgaagg tgatcacgct gaagtccaag   2880
ctggtgagcg acttccggaa ggacttccag ttctacaagg tgcgggagat caacaactac   2940
catcacgccc atgacgccta cctgaacgcc gtggtcggaa ccgccctgat caagaaatac   3000
cccaagctgg agtccgaatt cgtgtacgga gattacaagg tctacgacgt gcggaagatg   3060
atcgcgaagt ccgagcagga gatcggcaaa gccaccgcca agtacttctt ttactccaac   3120
atcatgaact tcttcaagac cgagatcacg ctcgccaacg gcgagatccg caagcgcccc   3180
ctgatcgaga ccaacggcga gacgggagag attgtgtggg acaaaggaag agattttgcc   3240
acagtgcgca aggtgctgtc catgcctcag gtgaacatcg tgaagaagac cgaggtgcaa   3300
acaggagggt tttccaaaga gtccattttg cctaagagga attccgacaa gctcatcgcc   3360
```

```
cgcaagaagg actgggaccc caagaagtac gggggcttcg actcccccac ggtggcctac   3420

tccgtgttgg tggtggccaa agtggagaaa gggaagagca agaagctgaa atccgtgaag   3480

gagttgctcg gaatcacgat catggaacga tcgtcgttcg agaaaaaccc catcgacttc   3540

ctcgaagcca aagggtacaa agaggtgaag aaggacctga tcatcaagct gcccaagtac   3600

tccctgttcg agctggagaa cggccgcaag cggatgctgg cctccgccgg ggaactgcag   3660

aaagggaacg aattggcctt gccctccaaa tacgtgaact tcctctactt ggcctcccat   3720

tacgaaaagc tcaaaggatc ccctgaggac aatgagcaga agcaactctt cgtggaacaa   3780

cacaagcact acctggacga gatcatcgag cagatcagcg agttctccaa gcgcgtgatc   3840

ctcgccgacg ccaacctgga caaggtgctc tccgcctaca acaagcaccg cgacaagcct   3900

atccgcgagc aagccgagaa tatcattcac ctgtttaccc tgacgaattt gggagcccct   3960

gccgccttta aatactttga caccaccatc gaccgcaaaa gatacacctc caccaaggaa   4020

gtcttggacg ccaccctcat ccaccagtcc atcacgggcc tctacgagac gcgcatcgac   4080

ctctcccaat tgggcggcga c                                              4101
```

<210> SEQ ID NO 33
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes FLAG tag

<400> SEQUENCE: 33

```
gactacaagg atgacgatga caag                                             24
```

<210> SEQ ID NO 34
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes nuclear localization signal

<400> SEQUENCE: 34

```
cccaagaaaa agcggaaggt cggc                                             24
```

<210> SEQ ID NO 35
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes peptide linker

<400> SEQUENCE: 35

```
atgcccaaga aaaagcggaa ggtcggcgac tacaaggatg acgatgacaa gttggagcct     60

ggagagaagc cctacaaatg ccctgagtgc ggaaagagct tcagccaatc tggagccttg    120

acccggcatc aacgaacgca tacacga                                         147
```

<210> SEQ ID NO 36
<211> LENGTH: 1000

<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 36

```
aataagcata catcatatga atacaattca gcttaaattt atcatacaaa gatgtaagtg     60
cagcgtgggt ctgtaacgat cgggcgtaat ttaagataat gcgagggacc gggggaggtt    120
ttggaacgga atgaggaatg ggtcatggcc cataataata atatgggttt ggtcgcctcg    180
cacagcaacc gtacgtgcga aaaaggaaca gatccattta ataagttgaa cgttattctt    240
tcctatgcaa tgcgtgtatc ggaggcgaga gcaagtcata ggtggctgcg cacaataatt    300
gagtctcagc tgagcgccgt ccgcgggtgg tgtgagtggt catcctcctc ccggcctatc    360
gctcacatcg cctctcaatg gtggtggtgg ggcctgatat gacctcaatg ccgacccata    420
ttaaaaccca gtaaagcatt caccaacgaa cgaggggctc ttttgtgtgt gttttgagta    480
tgattttaca cctctttgtg catctctctg gtcttccttg gttcccgtag tttgggcatc    540
atcactcacg cttccctcga ccttcgttct tcctttacaa ccccgacaca ggtcagagtt    600
ggagtaatca aaaaaggggt gcacgaatga gatacattag attttgacag atatcctttt    660
actggagagg gttcaaggga tcaaatgaac agcgggcgtt ggcaatctag ggagggatcg    720
gaggttggca gcgagcgaaa gcgtgtccat ccttttggct gtcacacctc acgaaccaac    780
tgttagcagg ccagcacaga tgacatacga gaatctttat tatatcgtag accttatgtg    840
gatgaccttt ggtgctgtgt gtctggcaat gaacctgaag gcttgatagg gaggtggctc    900
ccgtaaaccc tttgtccttt ccacgctgag tctcccccgc actgtccttt atacaaattg    960
ttacagtcat ctgcaggcgg tttttctttg gcaggcaaag                         1000
```

<210> SEQ ID NO 37
<211> LENGTH: 317
<212> TYPE: DNA
<213> ORGANISM: Nannochloropsis gaditana
<220> FEATURE:
<221> NAME/KEY: misc_feature
<223> OTHER INFORMATION: Bidirectional terminator 2

<400> SEQUENCE: 37

```
agtgatgcgg cctttaggaa acaccacaaa agtaattgac aatctcagga acgatctgcg     60
tgtttacagc ttcccaaata acaattatac cacgtaccaa aaggggttta atgtatctca    120
caaattcttc taataggtac agcttctcaa attgggtgta tgatgtgaca cttcgtctca    180
cacacgtcac gataattcag cgtatggctt cccttcatca cattcacgca aacttctaca    240
caaccctggg catatttctt gtgttggcaa cactcccgaa atcgattctg cacacaatgg    300
ttcattcaat gattcaa                                                   317
```

<210> SEQ ID NO 38
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Aspergillus terreus BLAST gene codon optimized for N. gaditana

<400> SEQUENCE: 38

```
atggccaagc ctttatccca agaggaatcc acgctgatcg aacgtgcaac tgcgaccatc     60

aacagcatac ctattagcga ggactactcg gtggccagtg cagccctctc gtccgacggt    120

cggatcttta ccggcgtgaa tgtatatcat ttcaccggag ggccatgcgc ggagctcgtg    180

gtcctcggaa cggccgctgc ggctgctgcc ggaaatctga cgtgcatagt ggccatcggg    240

aacgaaaacc gcggcattct gtctccgtgc gggcgatgtc ggcaggtgct gcttgacttg    300

cacccgggga tcaaggcaat tgtcaaagat tccgatgggc agcccacagc ggttggcatc    360

agggagttgc ttccctctgg ctacgtctgg gagggttga                           399
```

```
<210> SEQ ID NO 39
<211> LENGTH: 999
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 39

cgtgcaggtg tacagattga aggaaacaat ggagatatct ttggcagttg aaaaccgtgt     60

tcgaatcatg cttttctact ctccaactga gacgaaattt atagcgccat gtcgcttctg    120

actaccaggc ttaggaaggc ctcatcacaa gctggatcgg ttcgaattaa gcaggcactg    180

aagccaagct tgcaagacag ccacctttta attccctcaa aacactttct caattcagcc    240

cggtaaatat gccgattcac agcggccaag atagagggga ggttagcaag aatgttgcga    300

tccctcccca gtcgttgcct cgcacacaac ctaggccttc acctttccat ggaaaattga    360

gaagtgaata ttggttttct tacggcatat cagatgaaat catgacccct aaacatgaag    420

agctgcaggc aaaacacctg ctctggacga gcacgatgaa atctcgagaa cccgccgtac    480

ttcagttgat cccgcatgat gacggccgcc attgaaataa gccacctcac tttattctag    540

caccgatttc caccgttgtg agggccgaac gaggacaatt tcgtgcgaaa caagcacgaa    600

cacgcacacg attagtagta cagacgagca gatcgatggc atgcggcacg gtctcgcgtt    660

ctcggcgacc aggacaacgg agcagaggga ggcctgccga gttccgaggg gcattttagt    720

ccaaaattgt gttgacacgt gaacaagtgg cttgaaaaga ggaaggaaat gcctgggttt    780

cccttcgaga gcgggaactc gcttgtgcgt catcctagct acccatggtc cctttgtggg    840

ggaggctgtt tcgtcctacc gaatgtgtgg cgctccatgc atcttctgcc tcccaaacca    900

ccaacatgag cacgcgaagg aaggagaaaa aagtggccgc aacgttctct tctcatattt    960

attgtctcat cacaaacata ggtacataat acaacaatc                           999
```

```
<210> SEQ ID NO 40
<211> LENGTH: 317
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 40

agtgatgcgg cctttaggaa acaccacaaa agtaattgac aatctcagga acgatctgcg     60

tgtttacagc ttcccaaata acaattatac cacgtaccaa aaggggttta atgtatctca    120

caaattcttc taataggtac agcttctcaa attgggtgta tgatgtgaca cttcgtctca    180

cacacgtcac gataattcag cgtatggctt cccttcatca cattcacgca aacttctaca    240

caaccctggg catatttctt gtgttggcaa cactcccgaa atcgattctg cacacaatgg    300
```

ttcattcaat gattcaa 317

<210> SEQ ID NO 41
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TurboGFP gene codon optimized for N. gaditana

<400> SEQUENCE: 41
atgttggaga gcgacgagag cggcctgccc gccatggaga tcgagtgccg catcaccggc 60
accctgaacg gcgtggagtt cgagctggtg ggcggcggag agggcacccc cgagcagggc 120
cgcatgacca acaagatgaa gagcaccaaa ggcgccctga ccttcagccc ctacctgctg 180
agccacgtga tgggctacgg cttctaccac ttcggcacct accccagcgg ctacgagaac 240
cccttcctgc acgccatcaa caacggcggc tacaccaaca cccgcatcga gaagtacgag 300
gacggcggcg tgctgcacgt gagcttcagc taccgctacg aggccggccg cgtgatcggc 360
gacttcaagg tgatgggcac cggcttcccc gaggacagcg tgatcttcac cgacaagatc 420
atccgcagca acgccaccgt ggagcacctg caccccatgg gcgataacga tctggatggc 480
agcttcaccc gcaccttcag cctgcgcgac ggcggctact acagctccgt ggtggacagc 540
cacatgcact tcaagagcgc catccacccc agcatcctgc agaacggggg ccccatgttc 600
gccttccgcc gcgtggagga ggatcacagc aacaccgagc tgggcatcgt ggagtaccag 660
cacgccttca agaccccgga tgcagatgcc ggtgaagaat aa 702

<210> SEQ ID NO 42
<211> LENGTH: 822
<212> TYPE: DNA
<213> ORGANISM: Nannochloropsis gaditana
<220> FEATURE:
<221> NAME/KEY: misc_feature
<223> OTHER INFORMATION: 4AIII promoter

<400> SEQUENCE: 42
ggcataaagg acggcaagga aagaaaagaa agaaagaaaa ggacacttat agcatagttt 60
gaagttataa gtagtcgcaa tctgtgtgca gccgacagat gctttttttt tccgtttggc 120
aggaggtgta gggatgtcga agaccagtcc agctagtatc tatcctacaa gtcaatcatg 180
ctgcgacaaa aatttctcgc acgaggcctc tcgataaaca aaactttaaa agcacacttc 240
attgtcatgc agagtaataa ctcttccgcg tcgatcaatt tatcaatctc tatcatttcc 300 gccccttttcc ttgcatagag caagaaaagc gacccggatg aggataacat gtcctgcgcc 360
agtagtgtgg cattgcctgt ctctcattta cacgtactga aagcataatg cacgcgcata 420
ccaatatttt tcgtgtacgg agatgaagag acgcgacacg taagatcacg agaaggcgag 480
cacggttgcc aatggcagac gcgctagtct ccattatcgc gttgttcggt agcttgctgc 540
atgtcttcag tggcactata tccactctgc ctcgtcttct acacgagggc cacatcggtg 600
caagttcgaa aaatcatatc tcaatcttca gatcctttcc agaaacggtg ctcaggcggg 660
aaagtgaagg ttttctactc tagtggctac cccaattctc tccgactgtc gcagacggtc 720
cttcgttgcg cacgcaccgc gcactacctc tgaaattcga caaccgaagt tcaattttac 780
atctaacttc tttcccattc tctcaccaaa agcctagctt ac 822

<210> SEQ ID NO 43
<211> LENGTH: 200
<212> TYPE: DNA
<213> ORGANISM: Nannochloropsis gaditana
<220> FEATURE:
<221> NAME/KEY: misc_feature
<223> OTHER INFORMATION: Bidirectional terminator 5

<400> SEQUENCE: 43
gggtgggaag gagtcgggga gggtcctggc agagcggcgt cctcatgatg tgttggagac 60
ctggagagtc gagagcttcc tcgtcacctg attgtcatgt gtgtataggt taagggggcc 120
cactcaaagc cataaagacg aacacaaaca ctaatctcaa caaagtctac tagcatgccg 180
tctgtccatc tttatttcct 200

<210> SEQ ID NO 44
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Target sequence for cpSRP54 gene

<400> SEQUENCE: 44
ggccacgccc ttgctccgtc 20

<210> SEQ ID NO 45
<211> LENGTH: 2400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HygR cassette

<400> SEQUENCE: 45
tccacagccc gaacccatga gagagaatca taatcaaaga tgagccagcc acgaagctac 60
cggagaattc tgtaagaaaa atgtttaaag ttgaaaatgc taacagtgaa gtgatatcct 120
tttttaatgg agtgttgagg tgaagtctag catcgtaggg gaaaacagga ttctgtgtct 180
tccattctac tccttgataa agcgaagaaa tccgacaaaa ccaaagagat tgttcaagtt 240
taagatttgt aagcgtacaa ctatgaactt cttctctttg taggcctgag tggtcgtatg 300
catacgattc atgaagtgaa tcagtatcgc tggattttgc ttaggagtaa agcacaacta 360
agaaaatatg ctgcctggca ggcatcctga gacatgaggc aagcgacgta gcaattgaat 420
cctaatttaa gccagggcat ctgtatgact ctgttagtta attgatgaac caatgagctt 480
taaaaaaaaa tcgttgcgcg taatgtagtt ttaattctcc gccttgaggt gcggggccat 540
ttcggacaag gttctttgga cggagatggc agcatgtgtc ccttctccaa attggtccgt 600
gtggtagttg agatgctgcc ttaaaattct gctcggtcat cctgccttcg cattcactcc 660
tttcgagctg tcgggttcct cacgaggcct ccgggagcgg attgcgcaga aaggcgaccc 720
ggagacacag agaccataca ccgactaaat tgcactggac gatacggcat ggcgacgacg 780
atggccaagc attgctacgt gattattcgc cttgtcattc agggagaaat gatgacatgt 840
gtgggacggt ctttacatgg gaagagggca tgaaaataac atggcctggc gggatggagc 900
gtcacacctg tgtatgcgtt cgatccacaa gcaactcacc atttgcgtcg gggcctgtct 960
ccaatctgct ttaggctact ttctctaat ttagcctatt ctatacagac agagacacac 1020
agggatcatg gggaagaaac cggaactgac cgctacgtcc gtggagaaat tccttattga 1080
gaagttcgac tctgtctccg acttgatgca actgagcgag ggagaggaga gtagggcgtt 1140
ctcgtttgac gtagggggtc ggggatacgt gttgagggtt aatagttgtg cggacgggtt 1200
ctacaaggat cggtatgtct accgtcattt cgcctccgcc gctctcccca taccagaggt 1260
actggacatt ggggagttta gcgaatctct cacgtactgc atctcgcgcc gagcccaggg 1320
agtgacgttg caagatctgc ccgaaactga attgcctgcc gttttgcaac ccgtggccga 1380
ggccatggac gcgatcgctg ccgcagatct gtctcagacg tccggctttg gaccttttgg 1440
gccccagggc atcgggcagt acacgacctg gcgagacttc atctgcgcca ttgccgatcc 1500
tcacgtctat cattggcaga cagtcatgga tgacaccgtg tctgcatccg tggcccaagc 1560
actggacgaa ctcatgttgt gggccgagga ttgccctgag gtcaggcacc tggtgcacgc 1620
ggatttcggc agcaataacg tacttacaga caatggtcgg attactgctg tcatcgactg 1680
gtccgaagcg atgtttggtg atagccaata cgaagtggcg aacatattct tctggcgtcc 1740
ctggttggcg tgcatggagc agcagacacg ctactttgaa cggaggcacc cggagctggc 1800
cggctcccca cgactccgcg cctatatgtt gcgtatcgga ctcgatcagc tttaccagtc 1860
tctcgtcgac ggcaacttcg acgacgccgc gtgggcgcag ggccgctgcg acgcgatagt 1920
ccgcagcggg gctgggacgg tgggtcggac ccaaatcgca cgccggtcgg ctgcggtgtg 1980
gacagacggc tgtgttgagg tgcttgcgga ctcgggcaac cgtaggccga gcacccgacc 2040
gcgtgcaaag gagtgattga atcattgaat gaaccattgt gtgcagaatc gatttcggga 2100
gtgttgccaa cacaagaaat atgcccaggg ttgtgtagaa gtttgcgtga atgtgatgaa 2160
gggaagccat acgctgaatt atcgtgacgt gtgtgagacg aagtgtcaca tcatacaccc 2220
aatttgagaa gctgtaccta ttagaagaat ttgtgagata cattaaaccc cttttggtac 2280
gtggtataat tgttatttgg gaagctgtaa acacgcagat cgttcctgag attgtcaatt 2340
acttttgtgg tgtttcctaa aggccgcatc actgcccgaa tcgagttgat ggcccgcaaa 2400

<210> SEQ ID NO 46
<211> LENGTH: 1029
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Hygromycin resistance gene, codon optimized for Nannochloropsis

<400> SEQUENCE: 46
atggggaaga aaccggaact gaccgctacg tccgtggaga aattccttat tgagaagttc 60
gactctgtct ccgacttgat gcaactgagc gagggagagg agagtagggc gttctcgttt 120
gacgtagggg gtcggggata cgtgttgagg gttaatagtt gtgcggacgg gttctacaag 180
gatcggtatg tctaccgtca tttcgcctcc gccgctctcc ccataccaga ggtactggac 240
attggggagt ttagcgaatc tctcacgtac tgcatctcgc gccgagccca gggagtgacg 300
ttgcaagatc tgcccgaaac tgaattgcct gccgttttgc aacccgtggc cgaggccatg 360
gacgcgatcg ctgccgcaga tctgtctcag acgtccggct ttggaccttt tgggccccag 420
ggcatcgggc agtacacgac ctggcgagac ttcatctgcg ccattgccga tcctcacgtc 480
tatcattggc agacagtcat ggatgacacc gtgtctgcat ccgtggccca agcactggac 540
gaactcatgt tgtgggccga ggattgccct gaggtcaggc acctggtgca cgcggatttc 600

```
ggcagcaata acgtacttac agacaatggt cggattactg ctgtcatcga ctggtccgaa    660

gcgatgtttg gtgatagcca atacgaagtg gcgaacatat tcttctggcg tccctggttg    720

gcgtgcatgg agcagcagac acgctacttt gaacggaggc acccggagct ggccggctcc    780

ccacgactcc gcgcctatat gttgcgtatc ggactcgatc agctttacca gtctctcgtc    840

gacggcaact tcgacgacgc cgcgtgggcg cagggccgct gcgacgcgat agtccgcagc    900

ggggctggga cggtgggtcg gacccaaatc gcacgccggt cggctgcggt gtggacagac    960

ggctgtgttg aggtgcttgc ggactcgggc aaccgtaggc cgagcacccg accgcgtgca   1020

aaggagtga                                                           1029
```

<210> SEQ ID NO 47
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: EIF3 promoter

<400> SEQUENCE: 47

```
tcataatcaa agatgagcca gccacgaagc taccggagaa ttctgtaaga aaaatgttta     60

aagttgaaaa tgctaacagt gaagtgatat cctttttttaa tggagtgttg aggtgaagtc    120

tagcatcgta ggggaaaaca ggattctgtg tcttccattc tactccttga taaagcgaag    180

aaatccgaca aaaccaaaga gattgttcaa gtttaagatt tgtaagcgta caactatgaa    240

cttcttctct ttgtaggcct gagtggtcgt atgcatacga ttcatgaagt gaatcagtat    300

cgctggattt tgcttaggag taaagcacaa ctaagaaaat atgctgcctg gcaggcatcc    360

tgagacatga ggcaagcgac gtagcaattg aatcctaatt taagccaggg catctgtatg    420

actctgttag ttaattgatg aaccaatgag ctttaaaaaa aaatcgttgc gcgtaatgta    480

gttttaattc tccgccttga ggtgcggggc catttcggac aaggttcttt ggacggagat    540

ggcagcatgt gtcccttctc caaattggtc cgtgtggtag ttgagatgct gccttaaaat    600

tctgctcggt catcctgcct tcgcattcac tcctttcgag ctgtcgggtt cctcacgagg    660

cctccgggag cggattgcgc agaaaggcga cccggagaca cagagaccat acaccgacta    720

aattgcactg gacgatacgg catggcgacg acgatggcca agcattgcta cgtgattatt    780

cgccttgtca ttcagggaga aatgatgaca tgtgtgggac ggtctttaca tgggaagagg    840

gcatgaaaat aacatggcct ggcgggatgg agcgtcacac ctgtgtatgc gttcgatcca    900

caagcaactc accatttgcg tcggggcctg tctccaatct gctttaggct acttttctct    960

aatttagcct attctataca gacagagaca cacagggatc                         1000
```

<210> SEQ ID NO 48
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic
<220> FEATURE:
<221> NAME/KEY: misc_feature
<223> OTHER INFORMATION: 5'ID sequence

<400> SEQUENCE: 48

```
tccacagccc gaacccatga gagagaa                                          27
```

<210> SEQ ID NO 49
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic
<220> FEATURE:
<221> NAME/KEY: misc_feature
<223> OTHER INFORMATION: 3'ID sequence

<400> SEQUENCE: 49
gcccgaatcg agttgatggc ccgcaaa 27

<210> SEQ ID NO 50
<211> LENGTH: 20
<212> TYPE: DNA
<213> ORGANISM: Nannochloropsis gaditana
<220> FEATURE:
<221> NAME/KEY: misc_feature
<223> OTHER INFORMATION: 5' Primer, cpSRP54 locus

<400> SEQUENCE: 50
gcaggacaat gaaattgacg 20

<210> SEQ ID NO 51
<211> LENGTH: 20
<212> TYPE: DNA
<213> ORGANISM: Nannochloropsis gaditana
<220> FEATURE:
<221> NAME/KEY: misc_feature
<223> OTHER INFORMATION: 3' Primer, cpSRP54 locus

<400> SEQUENCE: 51
gtggaggaac gtcagaggac 20

<210> SEQ ID NO 52
<211> LENGTH: 516
<212> TYPE: PRT
<213> ORGANISM: Nannochloropsis gaditana
<220> FEATURE:
<221> NAME/KEY: misc_feature
<223> OTHER INFORMATION: Ftsy polypeptide

<400> SEQUENCE: 52

```
Met Leu Gln Tyr His Leu Leu Leu Leu Pro Leu Leu Met Leu Pro Trp
1               5                   10                  15

Ala Gly Trp Thr Gln Ala Ala Phe Val Thr Pro Arg Val Gly Gly Pro
            20                  25                  30

Arg Ser Tyr Gly Asp Gly Arg Lys Tyr Arg Val Gly Val Pro Phe Tyr
        35                  40                  45

Ser Ser Ile Asp Glu Val Asp Ser Pro Ile Tyr Thr Thr Ala Ser Arg
    50                  55                  60

Ser Arg Arg Gln Gly Glu Ser His Met Met Val Phe Asp Phe Ile Arg
65                  70                  75                  80

Lys Arg Ala Glu Glu Gly Ile Gln Gln Val Gln Asn Ile Ala Thr Lys
                85                  90                  95

Thr Ala Glu Gly Lys Phe Val Glu Ala Leu Gly Asp Thr Ala Ser Tyr
            100                 105                 110

Val Lys Lys Arg Gln Glu Ile Asp Ala Glu Asn Leu Ala Lys Leu Gln
        115                 120                 125
```

```
Glu Gly Leu Ala Lys Ser Arg Gln Arg Leu Met Gly Asp Leu Asp Val
    130                 135                 140

Ile Phe Gly Val Ser Glu Asp Val Gly Leu Thr Lys Thr Leu Asp Lys
145                 150                 155                 160

Leu Glu Glu Val Leu Met Met Ser Asp Ile Gly Ala Ala Thr Thr Gly
                165                 170                 175

Glu Ile Ile Asp Asp Leu Arg Met Val Ala Lys Ala Glu Lys Leu Glu
            180                 185                 190

Pro Asp Asp Val Lys Ser Val Leu Arg Leu Arg Leu Ile Glu Ala Leu
        195                 200                 205

Thr Ala Lys Asp Arg Ser Met Gln Leu Lys Lys Glu Ala Ser Ala Gly
    210                 215                 220

Asn Gly Lys Ser Tyr Pro Arg Val Leu Phe Val Ile Gly Ala Asn Gly
225                 230                 235                 240

Met Gly Lys Thr Thr Thr Ile Gly Lys Ile Ala Ser Arg Leu Lys Asn
                245                 250                 255

Glu Ala Asn Gln Ser Val Leu Val Ala Ala Cys Asp Thr Phe Arg Ala
            260                 265                 270

Ala Ala Val Asp Gln Leu Glu Glu Trp Thr Val Arg Ala Gly Val Asp
        275                 280                 285

Ile His Arg Pro Gly Glu Gly Gln Thr Lys Pro Ala Pro Val Leu Glu
    290                 295                 300

Glu Ala Ile Ser Lys Ala Ile Glu Gly Asp Tyr Asp Val Leu Ile Val
305                 310                 315                 320

Asp Thr Ser Gly Arg Leu Ser Asn Asn Val Ala Leu Asn Glu Glu Leu
                325                 330                 335

Lys Lys Leu Lys Arg Thr Ile Ala Asp Gly Ile Pro Gly Gly Pro His
            340                 345                 350

Glu Thr Leu Leu Val Leu Asp Gly Ala Val Gly Arg Asn Gly Val Asp
        355                 360                 365

Gln Ala Lys Val Trp Asn Arg Glu Val Gly Ile Thr Gly Leu Val Ile
    370                 375                 380

Thr Lys Leu Asp Gly Thr Ala Arg Gly Gly Val Val Val Ser Ile Val
385                 390                 395                 400

Arg Asp Val Gly Val Pro Val Lys Leu Ile Gly Val Gly Glu Gly Ile
                405                 410                 415

Asp Asp Leu Arg Asp Phe Asn Pro Glu Asp Phe Val Asp Ala Leu Leu
            420                 425                 430

Gly Tyr Glu Pro Glu Gln Val Leu Ala Leu Glu Ala Arg Leu Gln Asp
        435                 440                 445

Met Val Gln Gly Lys Leu Ile Lys Pro Lys Arg Gly Val Ile Val Arg
    450                 455                 460

Ser Glu Gly Gly Gly Arg Asp Lys Asn Met Asp Ala Asp Asp Ile Ser
465                 470                 475                 480

Asp Arg Met Arg Arg Lys Val Gln Gly Arg Gly Gly Gln Gly Gly Ser
                485                 490                 495

Ser Ser Gln Arg Gly Gly Gly Lys Gly Gly Lys Ser Gly Gly Gly Lys
            500                 505                 510

Lys Lys Arg Arg
        515
```

<210> SEQ ID NO 53
<211> LENGTH: 1551

```
<212> TYPE: DNA
<213> ORGANISM: Nannochloropsis gaditana
<220> FEATURE:
<221> NAME/KEY: misc_feature
<223> OTHER INFORMATION: Encodes Ftsy polypeptide

<400> SEQUENCE: 53

atgttgcagt atcacctcct cctcctacct ctcctgatgc tgccttgggc aggatggact     60

caagctgcat tcgttactcc aagagttgga ggcccaagat cttatggtga tggaagaaaa    120

tacagagtcg gtgtgccatt ctactcgtca atcgacgagg tagacagtcc tatctacacc    180

acggcatcac gatccagaag gcaaggtgaa agccacatga tggtattcga ttttattcga    240

aagcgggcag aagagggaat acaacaagta caaaacatcg ctactaaaac tgcggagggg    300

aagtttgtgg aagctctagg cgacacagcc tcctacgtca aaaagcgaca ggaaatcgac    360

gctgagaacc ttgcgaagct tcaagaaggc ttagcaaaga gcaggcagcg tctgatgggg    420

gacttggatg tgatttttgg tgtgagcgag gatgtgggcc tcacgaagac tttggataag    480

ctggaggaag tgctgatgat gtcggacata ggggcggcca cgacgggtga aatcatcgac    540

gacctccgca tggtcgccaa ggccgagaaa ctcgagcctg acgacgtcaa gtctgtcctc    600

cgtttgcgtt tgatcgaggc gttgacggcc aaggatagga gtatgcagtt gaaaaaggaa    660

gcgtccgcgg ggaatggaaa gagctaccct cgtgtcctct tcgtcatcgg tgcgaacggg    720

atgggcaaga cgacgacgat cggaaagatc gcctcccgcc tcaaaaatga agcgaatcag    780

agtgtgctgg ttgccgcctg tgacactttt cgcgccgccg ctgtcgacca gctggaggag    840

tggacggtgc gagccggcgt ggacatccac cggccagggg aagggcagac gaaacccgcg    900

cccgtgctgg aagaggctat cagtaaggcg atcgaaggag actacgacgt gctgattgtg    960

gacacatctg ggcggctttc aaataacgtg gccttgaacg aggagctcaa gaagttgaaa   1020

aggaccatcg cggacggcat ccctggtggc ccgcatgaga ccctactcgt cttagacggc   1080

gccgtgggca ggaatggggt agatcaggca aaggtctgga atcgagaggt tggaatcacg   1140

gggttggtca tcacgaaact tgacggcacg gccaggggag gtgtggtggt tagcatcgtg   1200

agggacgtgg gcgtccctgt gaagctcatt ggagtgggcg aggggattga tgacttgcgg   1260

gatttcaatc cagaggattt tgtggatgct ttgttgggat atgagcctga acaggtgctg   1320

gccttggagg cccggcttca agacatggtt caaggcaaac ttatcaagcc gaagagaggg   1380

gtaattgtac gctctgaagg tggtggacgc gataagaata tggatgcaga cgatatcagc   1440

gacaggatga gacggaaagt ccaaggacgg gggggccagg gcggttcctc ctcgcagcgt   1500

ggagggggaa aaggaggaaa aagcggtggt ggcaagaaaa agaggcggta a            1551


<210> SEQ ID NO 54
<211> LENGTH: 19
<212> TYPE: DNA
<213> ORGANISM: Nannochloropsis gaditana
<220> FEATURE:
<221> NAME/KEY: misc_feature
<223> OTHER INFORMATION: Ftsy gene target sequence

<400> SEQUENCE: 54

ggcaggggaa agattaatg                                                   19


<210> SEQ ID NO 55
<211> LENGTH: 489
<212> TYPE: PRT
<213> ORGANISM: Nannochloropsis gaditana
<220> FEATURE:
```

<221> NAME/KEY: misc_feature
<223> OTHER INFORMATION: ALB3 polypeptide

<400> SEQUENCE: 55

```
Met Pro Gln Pro Phe Phe Trp Ser Cys Arg Glu Gln Cys Cys Asp Pro
1               5                   10                  15

Cys Leu Gln His Ser His Arg Ser Glu Leu Ser Tyr Leu Phe Asp Phe
            20                  25                  30

Phe His Ser Asn Arg Met Val Met Arg Thr His Gln Arg Glu Met Trp
        35                  40                  45

Arg Gln Gln Gln Cys Leu Gly Arg Arg Leu Gly Ser Cys Ile Phe Cys
    50                  55                  60

Leu Leu Met Ala Ser Leu Leu Phe Thr Ser Glu Val Val Thr Ala Phe
65                  70                  75                  80

Val Pro Val Ala Thr Arg Arg Pro Asp Leu Leu His Val Ser Arg Pro
                85                  90                  95

Pro Phe Pro Ser Arg Ala Thr Pro Gly Thr Arg Ala Leu Arg Met Val
            100                 105                 110

Leu Gln Pro His Asp Val Val Thr His Leu Asp Pro Ala Trp Leu Ser
        115                 120                 125

His Val Phe Gln Gly Val Ala Asp Ala Ala Val Thr Ser Leu Asp Ala
    130                 135                 140

Thr Asn Ala Ala Val Asp Ala Thr Thr Asp Ala Ala Ala Lys Glu Pro
145                 150                 155                 160

Gly Phe Phe Asp Lys Phe Val Asn Thr Val Met Gly Ala Ile Glu Gly
                165                 170                 175

Val His Ser Glu Leu Val Ser Leu Gly Val Pro Gly Ala Tyr Gly Leu
            180                 185                 190

Ala Ile Ile Leu Phe Thr Ala Gly Val Lys Leu Ala Leu Leu Pro Val
        195                 200                 205

Thr Tyr Lys Gln Met Glu Ser Ala Gln Arg Met Gln Ala Leu Ala Pro
    210                 215                 220

Lys Ala Lys Glu Leu Lys Asp Lys Tyr Gly Lys Asn Lys Ala Leu Leu
225                 230                 235                 240

Asn Gln Leu Thr Ala Lys Leu Tyr Glu Asp Ala Glu Val Asn Pro Leu
                245                 250                 255

Ala Gly Cys Leu Pro Ala Leu Ala Gln Ile Pro Ile Phe Ile Ala Leu
            260                 265                 270

Tyr Arg Ser Leu Ile Asn Leu Ala Gly Asn Ser Asp Phe Asn Glu Pro
        275                 280                 285

Phe Leu Trp Leu Pro Ser Leu Ala Gly Pro Leu Tyr Gly Gln Ala Arg
    290                 295                 300

Gly Thr Asp Trp Leu Phe Lys Asn Trp Val Asp Gly Val Pro Ala Leu
305                 310                 315                 320

Gly Trp His Asp Thr Ile Ala Phe Leu Thr Ile Pro Val Ile Leu Ile
                325                 330                 335

Leu Thr Gln Ser Ile Ser Gln Arg Leu Leu Thr Pro Pro Ser Asp Asp
            340                 345                 350

Pro Lys Thr Ala Gln Thr Gln Arg Val Leu Lys Tyr Leu Pro Ile Met
        355                 360                 365

Val Gly Tyr Phe Ser Leu Ser Val Pro Ser Gly Leu Gly Val Tyr Trp
    370                 375                 380

Ile Thr Asn Asn Leu Ile Ser Thr Ala Ile Ser Ile Ser Ile Lys Glu
385                 390                 395                 400
```

Lys Phe Ala Lys Gln Pro Ile Val Ile Asp Val Asp Val Asp Pro Glu
405 410 415

Asp Leu Gly Tyr Asp Pro Ser Thr Val Ala Met Gly Phe Glu Glu Met
420 425 430

Met Ala Glu Ala Thr Arg Asn Ala Leu Pro Ser Glu Gln Pro Lys Arg
435 440 445

Asp Arg Pro Thr Pro Ser Ser Leu Leu Lys Ala Ser Glu Ser Val Val
450 455 460

Ala Glu Glu Gly Gly Lys Arg Asp Glu Glu Ala Gly Arg Val Gly Glu
465 470 475 480

Glu Arg Glu Lys Ala Gly Val Glu Ala
485

<210> SEQ ID NO 56
<211> LENGTH: 1470
<212> TYPE: DNA
<213> ORGANISM: Nannochloropsis gaditana
<220> FEATURE:
<221> NAME/KEY: misc_feature
<223> OTHER INFORMATION: Encodes ALB3 polypeptide

<400> SEQUENCE: 56
atgccccaac cctttttttg gtcttgccgc gagcagtgct gtgatccgtg cctgcaacat 60
tcacatcgga gcgaactctc atatttgttc gatttttttcc attcaaacag gatggtcatg 120
cggacgcatc agcgtgagat gtggcgtcag cagcaatgtc tgggtagaag actagggtca 180
tgtatattct gtctcctgat ggcatccctt ttgtttactt ccgaggtggt cacagcattt 240
gtgcccgtcg ccacgcgtcg gcccgacctc ctccacgtct ctcgcccccc atttccttcg 300
agagccacgc caggtaccag agctttgcgc atggttttac agccgcacga tgtggtgacg 360
cacctggacc cagcgtggct ttcccacgtc tttcagggcg tggcagatgc ggccgtgact 420
tctttggatg cgacaaatgc cgcggtggac gccaccaccg atgccgccgc gaaggagccg 480
ggcttcttcg ataaattcgt gaacacggtc atgggcgcga tcgagggtgt gcacagtgaa 540
ctggtgtcgc tcggcgtccc tggcgcctac ggcttggcca tcatattgtt caccgcgggc 600
gtcaaactgg ccctgcttcc cgtcacctac aagcagatgg agtcagctca gcgtatgcag 660
gccctagcgc ccaaggcgaa ggagctcaag gacaagtacg ggaagaacaa ggcgctcctg 720
aaccagctga ccgccaagct ctacgaggac gcggaggtga accctctcgc cggctgcctt 780
cccgccctcg cccaaattcc cattttcatt gccctctacc gctccctgat caaccttgcg 840
gggaacagcg acttcaacga gccctttctc tggctgccga gtctggccgg gcctctctac 900
ggccaagccc gaggcacgga ctggctcttc aaaaactggg tggacggcgt cccggccctg 960
ggctggcacg acacaatcgc cttcctcacc atccccgtca tactgatcct cacgcagtct 1020
atctcccaac gactgctcac cccgcccagc gacgacccca agaccgcgca gacccagcgc 1080
gtcctcaaat atctgcccat catggtcggg tacttctctc tgagcgtgcc ctccggcctg 1140
ggtgtctact ggatcaccaa caatttgatc tccacggcca tctcgatcag catcaaggag 1200
aagttcgcca agcagccgat cgtgatcgac gtggatgtgg acccggagga cttgggctac 1260
gacccctcca cggtggccat gggcttcgaa gagatgatgg cggaggcgac gcgcaacgcg 1320
cttccaagcg agcagcccaa gcgggatcga ccgacgccat cctccctttt gaaagcgtca 1380
gagagtgtcg tggctgagga gggggggaag agggacgagg aggccggccg cgtgggggag 1440
gagagagaaa aagcgggcgt ggaggcctga 1470

<210> SEQ ID NO 57
<211> LENGTH: 20
<212> TYPE: DNA
<213> ORGANISM: Nannochloropsis gaditana
<220> FEATURE:
<221> NAME/KEY: misc_feature
<223> OTHER INFORMATION: ALB3 gene target sequence

<400> SEQUENCE: 57
gggaaagcca cgctgggtcc 20

<210> SEQ ID NO 58
<211> LENGTH: 562
<212> TYPE: PRT
<213> ORGANISM: Nannochloropsis gaditana
<220> FEATURE:
<221> NAME/KEY: misc_feature
<223> OTHER INFORMATION: Cytosolic SRP54 polypeptide

<400> SEQUENCE: 58

```
Met Val Leu Gln Glu Leu Gly Asp Lys Leu Thr Gly Ala Leu Arg Arg
1               5                   10                  15

Leu Gln Thr Thr Thr Val Val Asn Asp Asp Val Leu Asn Asp Leu Leu
            20                  25                  30

Gln Asp Val Cys Arg Ala Leu Val Glu Ser Asp Val Asn Ile Lys Val
        35                  40                  45

Val Ala Thr Leu Arg Lys Gly Ile Lys Glu Lys Val Asn Leu Ala Asp
    50                  55                  60

Ala Pro Ala Gly Leu Asn Arg Arg Lys Met Val Gln Arg Ala Val Met
65                  70                  75                  80

Glu Glu Leu Val Arg Leu Val Asp Ser Gly Thr Lys Pro Tyr Gln Met
                85                  90                  95

Arg Lys Gly Lys Ser Asn Val Ile Met Phe Val Gly Leu Gln Gly Ser
            100                 105                 110

Gly Lys Thr Thr Thr Ile Ala Lys Tyr Ala Asn Tyr Tyr Gln Arg Lys
        115                 120                 125

Gly Trp Lys Thr Cys Met Val Cys Ala Asp Thr Phe Arg Ala Gly Ala
    130                 135                 140

Phe Asp Gln Leu Lys Gln Asn Ala Thr Lys Leu Arg Val Pro Phe Tyr
145                 150                 155                 160

Gly Ser Tyr Thr Glu Ala Asp Pro Val Arg Ile Ala Glu Glu Gly Val
                165                 170                 175

Gln Gln Phe Arg Ser Glu Gly Tyr Glu Val Ile Ile Val Asp Thr Ser
            180                 185                 190

Gly Arg His Lys Gln Glu Glu Ala Leu Phe Glu Glu Met Lys Glu Ile
        195                 200                 205

Gln Ala Ala Val Arg Pro Asp Asn Val Val Tyr Val Met Asp Ala Thr
    210                 215                 220

Gln Gly Gln Ala Val Phe Asp Gln Ala Gln Gly Phe His Gln Ala Ala
225                 230                 235                 240

Ala Val Gly Ser Val Ile Val Thr Lys Leu Asp Gly His Ala Lys Gly
                245                 250                 255

Gly Gly Ala Leu Ser Ala Val Ala Ala Thr Gly Ala Pro Ile Ile Phe
            260                 265                 270

Leu Gly Ser Gly Glu His Phe Asp Asp Leu Asp Val Phe Asn Pro Gly
        275                 280                 285
```

```
Ser Phe Ile Ser Arg Leu Leu Gly Leu Gly Asp Met Arg Gly Phe Leu
    290                 295                 300

Glu Glu Val Ser Ser Leu Gly Ala Arg Glu Gly Gly Lys Glu Arg Gln
305                 310                 315                 320

Glu Ala Met Ala Gln Arg Leu Val Lys Gly Gln Phe Thr Leu Arg Asp
                325                 330                 335

Met Tyr Glu Gln Phe Glu Asn Val Met Lys Leu Gly Pro Leu Ser Lys
            340                 345                 350

Val Met Gly Met Leu Pro Gly Phe Pro Ser Phe Leu Met Gly Gly Gly
        355                 360                 365

Glu Gly Gly Arg Gly Gly Gln Asp Glu Ala Ala Thr Gly Arg Leu Lys
    370                 375                 380

Arg Phe Leu Thr Met Met Asp Ser Met Thr Asp Ala Glu Leu Asp Gly
385                 390                 395                 400

Lys Val Asp Leu Asn Lys Ser Glu Ser Arg Val Asn Arg Ile Ala Arg
                405                 410                 415

Gly Ser Gly Ala His Pro Met Glu Val Gln Phe Leu Leu Lys Thr Tyr
            420                 425                 430

Ala Gln Phe Ser Gln Met Phe Lys Lys Met Gly Pro Met Met Leu Lys
        435                 440                 445

Gly Gly Glu Gly Gly Ile Gln Arg Gln Met Ala Arg Asn Pro Gly Gly
    450                 455                 460

Val Met Asn Gln Leu Ser Lys Ala Val Asp Pro Arg Met Leu Gln Gln
465                 470                 475                 480

Met Gly Gly Ala Lys Gly Met Met Asp Met Met Lys Ala Met Gly Gly
                485                 490                 495

Gly Met Gly Gly Gly Leu Ala Asp Met Leu Gln Asn Leu Gly Gly Gly
            500                 505                 510

Gly Gly Gly Arg Gly Gly Gly Arg Gly Ser Gly Arg Gly Gly Gly Gly
        515                 520                 525

Met Asp Pro Glu Gln Met Gln Ala Gln Met Ala Gln Met Glu Glu Met
    530                 535                 540

Met Lys Ser Met Gly Met Gly Gly Gly Gly Lys Gly Gly Gly Gly Phe
545                 550                 555                 560

Pro Phe


<210> SEQ ID NO 59
<211> LENGTH: 1689
<212> TYPE: DNA
<213> ORGANISM: Nannochloropsis gaditana
<220> FEATURE:
<221> NAME/KEY: misc_feature
<223> OTHER INFORMATION: Encodes Cytosolic SRP54 polypeptide

<400> SEQUENCE: 59

atggtgttgc aggagctcgg tgacaagctt acgggggctc tacgccggct gcagaccacc      60

acggtcgtca acgacgacgt cctcaacgac ctgctccagg acgtatgccg tgcgttagtc     120

gaatccgatg tgaatatcaa ggtagtggcg accctaagaa agggcatcaa ggagaaagtc     180

aaccttgcag atgccccgc tggcctgaac agacggaaaa tggtgcagcg ggcggtgatg     240

gaggaattgg tccgcctggt cgactcggga acaaagccgt accaaatgag gaagggaaag     300

tcgaacgtga tcatgtttgt gggcttgcaa ggctcgggga aaactaccac cattgccaaa     360

tacgccaact attaccagcg gaagggatgg aagacgtgca tggtgtgtgc cgataccttt     420

cgtgccggag ccttcgatca gctgaagcag aatgcgacaa aactccgtgt gcctttttac     480
```

```
ggctcctaca cggaggcgga cccggtacgg atcgccgagg agggcgtcca gcagttccgt    540

tcagagggat acgaggttat cattgtcgat acctcgggcc ggcacaagca ggaagaagcc    600

ctgtttgagg agatgaaaga gatccaagcg gcggtccgtc ccgacaacgt ggtgtacgtc    660

atggacgcca cccagggcca agccgtcttc gaccaggcac agggtttcca ccaggccgcc    720

gcggtgggct ccgtcattgt caccaagctg gacgggcacg ccaagggggg aggcgccttg    780

tcggccgtgg cggcgacggg ggcgcctatc atatttttgg gctcggggga gcattttgac    840

gacctggacg tcttcaaccc cgggagtttc atcagtcggt tgctgggctt gggggacatg    900

cggggttttt tggaggaagt gagcagcctg ggggcgaggg aaggagggaa agagaggcag    960

gaggccatgg cccagcggct cgtcaagggc cagttcaccc tccgcgacat gtacgagcag   1020

tttgagaacg tgatgaagct ggggcccctt tccaaggtca tgggcatgct gccgggcttt   1080

ccctcttttc tgatgggggg gggggaagga gggagggggg ggcaggacga agctgccacg   1140

ggccggctga agcgtttctt gaccatgatg gacagcatga cggacgcgga gctcgatggg   1200

aaggtggacc tgaacaagag cgagagccgc gtgaaccgga ttgctcgagg aagcggggca   1260

cacccgatgg aagtccaatt tttgctcaag acgtacgcgc aattctcgca aatgttcaag   1320

aagatgggcc cgatgatgtt gaaaggcggg gagggtggca tacagcggca gatggcacgc   1380

aacccgggag gcgtgatgaa tcagttgagc aaggcggtgg acccgcgaat gctacagcag   1440

atgggaggcg caaaaggaat gatggacatg atgaaagcga tgggaggagg aatggggggg   1500

gggcttgcgg acatgctgca gaacttgggg ggaggggggg gagggagagg gggaggaaga   1560

gggagtggac gaggaggggg tggatggat ccagaacaga tgcaggcgca gatggcgcaa    1620

atggaagaga tgatgaaaag tatgggaatg ggtggaggag ggaaaggagg tggagggttc   1680

cctttctga                                                           1689
```

<210> SEQ ID NO 60
<211> LENGTH: 20
<212> TYPE: DNA
<213> ORGANISM: Nannochloropsis gaditana
<220> FEATURE:
<221> NAME/KEY: misc_feature
<223> OTHER INFORMATION: Cytosolic SRP54 gene target sequence

<400> SEQUENCE: 60

```
ggccagcggg ggcatctgca                                                 20
```

<210> SEQ ID NO 61
<211> LENGTH: 5607
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 gene codon optimized for Parachlorella and including Parachlorella introns, FLAG tag NLS, peptide linker

<400> SEQUENCE: 61

```
atgcccaaga agaagcggaa agtcggggac tacaaggacg acgatgacaa actggagcct     60

ggggagaagc cctataagtg tcctgagtgc gggaagagct tcagccaatc tggagcactg    120

acaaggcacc agaggacaca tacacgcgac aagaagtaca gcatcgggct ggatatcggg    180

accaattctg tgggatgggc cgtgattacc gacgagtata aggtgcccag caagaagttc    240

aaggtgctgg ggaacacaga ccgccacagc attaagaaga acctgatcgg ggcgctgctg    300
```

-continued

```
tttgattctg gagagacagc agaggcaacc gtgagtgaga acagttttca gatcgaatag    360
caccccccccg cctctgcagc agtcgcatac cggctgcagt aatagcttgg ttcaacggcg    420
acctgaacaa gtactgtagt ttctatgcat acgaacttta tcgaatagaa tcacgcttgg    480
gtatcgatca taccttagcg ctcaatttca ttggctgcta cagaccatat tttcctcttc    540
acttgttgca gcgcctgaaa agaacagcaa gaaggcgcta cacccgccgc aagaatagga    600
tttgctacct gcaagagatc ttcagcaacg agatggccaa ggtggacgac agcttcttcc    660
atagactgga ggagtcgttc ctggtggagg aggataagaa gcacgagagg caccccatct    720
tcggtgagaa gagtttggct accaaatcta tcttttcata tcacatatac cgcctgatat    780
tctgaggtgg tggcttttgt ctttttcttt cagtattttt cttcgttggg aacctaccgc    840
gagggcattc attgtggcgg atctgtaagt gcgaccaggc tgtatccaat attttttcct    900
atcgcaggga acattgtgga tgaggtggcc taccacgaga agtaccccac aatctaccac    960
ctgcgcaaga agctggtgag aatctctgct tgtcgaatgt gtccagttgt gtcttgaatc   1020
ctggcaagat gttcttttca ccatccgtcc tgcaaaagtg tcagaagtag catctctcga   1080
tcgcgttgtc acttcaacgc ctccgcaact ccccccgttg tgaatcctgt ggtcatggct   1140
cagcttttca gatctctacc tgcatgttgt ttgcctgtct cagtcctgcc tgcacaaatc   1200
atcgcccttg tttactcctt gcaatcacgg attgtgtgca ggtggacagc acagataagg   1260
ccgatctgag gctgatctac ctggcattgg cccacatgat caagtttagg gggcacttcc   1320
tcatcgaggg ggatttgaac cccgacaaca gcgatgtgga caagctgttc atccagctgg   1380
tgagtggagg gctggggttt gggggtgggg ggtggggagg gaggcacgga tggtgttttc   1440
tcatgtccaa ccgtggttca tgcaaccgaa cagcagtttc acaagatggt tccaacaggg   1500
tgctccattt ctccctgaca aaacctcgtg cggtccatct ggtatagctg ggttagtagg   1560
gggttgtggg ctgtccacag tcagtgcgaa gcaggctcta ttgagcgtgt gctagtgtgt   1620
gctgtgctga ttggcatttt gttgggccga gtgttaggat tagggtaaat caccctaatt   1680
aaccttacat aataggactg tatgcaaatt tgttttccaa aaactctacc cagcgtggtc   1740
agactgcatg cactgtggag catgcatggg gctgaccctg ttgatcctgc tcattctgct   1800
tcctccaggt gcagacctac aaccagctgt ttgaggagaa ccccatcaac gcatctgggg   1860
ttgacgcaaa ggccattctg tctgcaaggt aggtgcagga agaagtgaat gatgcacaca   1920
tggtggaatc gtgatacaag cagcagcaag tgttggacca agacatgtgc gtgctttgct   1980
gctgccaagc tggcactgca ccaggtcgtg cattgatctg cacatttgat atactgtgag   2040
agtcagacga cgtcctttca gagcctgtgt gtgattctcc aggggttaac acgagtttcc   2100
tttctgccag tgagtcaccc tctcgctgct cgctcctggt gcaggctgag caagtcaagg   2160
agactggaga acctgatcgc ccaattgcct ggagagaaga agaacgggct gttcgggaac   2220
ctgatcgcat tgtctctggg gttgaccccc aacttcaaga gcaacttcga cctggcagag   2280
gacgcaaaac tgcagctgag caaggacacc tacgacgatg atctggacaa cctgctggcc   2340
cagattggag atcagtacgc agacctgttc ctggcagcca agaatctgag cgacgcaatt   2400
ctgctgagcg acattctgcg cgtgaacacc gagatcacca aggcacctct gagcgcaagc   2460
atgatcaaga ggtacgacga gcaccaccaa gacctgacac tgctgaaagc actggtgaga   2520
cagcagctgc ctgagaagta caaggagatc ttcttcgacc agagcaagaa cgggtacgct   2580
gggtacattg atggaggagc aagccaagag gagttctaca agttcatcaa gcccatcctg   2640
```

-continued

```
gagaagatgg acgggacaga agagttgctg gtgaagctga atcgcgagga tctgctgagg   2700
aagcagagga cattcgacaa tgggagcatc ccacaccaga tccatctggg agagctgcac   2760
gcaattctga ggagacaaga ggacttctac ccgttcctga aggacaatcg cgagaagatc   2820
gagaagatcc tcacgttccg catcccgtac tatgtgggac ctctggcaag gggaactct    2880
agatttgcct ggatgacccg caagagcgag gagacaatta caccctggaa cttcgaggag   2940
gtggtggata aaggggcatc tgcacagagc ttcatcgaga ggatgaccaa cttcgacaag   3000
aacctgccca acgagaaggt actgcctaag cattcactgc tgtacgagta cttcaccgtg   3060
tacaacgagc tgaccaaggt gaagtacgtg acagagggga tgaggaagcc agcatttctg   3120
agcggagagc aaaagaaggc catcgtggat ctgctgttca agaccaaccg caaggtgacc   3180
gtgaagcagc tgaaggagga ctacttcaag aagatcgagt gcttcgacag cgtggagatt   3240
tctggagtgg aggaccgctt caacgcatct ttggggacat accacgacct gctgaagatc   3300
atcaaggaca aggacttcct ggacaacgag gagaacgagg acatcctgga ggacattgtg   3360
ctgacactga ccctgttcga ggatagggag atgatcgagg agcgcctgaa gacatacgca   3420
cacctgtttg acgacaaggt gatgaagcag ctgaagagga ggcgctatac tggatgggga   3480
aggctgtcaa ggaagctgat taacgggatc cgcgacaagc agagcgggaa gacaattctg   3540
gacttcctga agagcgacgg gttcgcaaac cgcaacttca tgcagctgat ccacgacgat   3600
agcctgacct tcaaggagga catccagaag gcccaagtgt ctggacaagg ggatagcctg   3660
catgagcaca tcgcaaatct ggctgggtca cccgcaatca agaagggaat tctgcagacc   3720
gtgaaggtgg tggatgagct ggtgaaggtg atgggaaggc acaaacccga gaacatcgtg   3780
atcgagatgg caagggagaa ccagacaacc cagaagggac agaagaactc tagggagcgc   3840
atgaagcgca tcgaggaggg aattaaggag ctgggaagcc agatcctgaa ggagcatcct   3900
gtggagaaca cccaactgca gaacgagaag ctgtacctgt actacctgca gaacgggagg   3960
gacatgtacg tggatcaaga gctggacatc aaccgcctga gcgactatga cgtggaccac   4020
attgtgcctc agtcgttcct gaaggacgac agcatcgaca acaaggtgct gacaaggagc   4080
gacaagaatc gcggaaagag cgacaacgtg ccttcagaag aggtggtgaa gaagatgaag   4140
aactactggc gccagctgct gaacgcaaag ctgattacac agcgcaagtt cgacaacctg   4200
accaaggcag agaggggagg actgtcagaa ctggataagg ccgggttcat caagaggcaa   4260
ctggtggaga cacgccagat cacaaagcat gtggcccaga ttctggacag ccgcatgaac   4320
accaagtacg acgagaacga caagctgatc cgcgaggtga aggtgattac cctgaagagc   4380
aagctggtga gcgactttcg caaggacttc cagttctaca aggtgcgcga gatcaacaac   4440
taccaccacg cacacgacgc ctacctgaat gcagttgtgg gaacagccct gatcaagaag   4500
taccccaagc tggagagcga gttcgtgtat ggggactaca aggtgtacga cgtgcgcaag   4560
atgatcgcca agtctgagca agagatcggg aaggcaaccg ccaagtactt cttctacagc   4620
aacatcatga acttcttcaa gaccgagatc accctggcca atggggagat taggaagaga   4680
cccctgatcg agaccaacgg agagactgga gagatcgtgt gggataaggg gagggacttt   4740
gcaacagtgc gcaaagtgct gagcatgcct caagtgaaca tcgtgaagaa gaccgaggtg   4800
cagactgggg gattctcaaa ggagagcatt ctgcccaagc gcaacagcga taagctgatt   4860
gcacgcaaga aggactggga ccccaagaag tatgggggggt ttgatagccc caccgtggca   4920
tattctgtgt tggttgtggc caaggtggag aaggggaaga gcaagaagct gaagagcgtg   4980
aaggagctgc tggggatcac cattatggag aggagcagct tcgagaagaa ccccatcgac   5040
```

```
ttcctggagg caaaggggta taaggaggtg aagaaggacc tgatcatcaa gctgcccaag   5100
tacagcctgt tcgagctgga gaatgggagg aagaggatgc tggcatctgc tggagaactg   5160
cagaagggga atgagttggc actgcctagc aagtacgtga acttcctgta cctggccagc   5220
cactacgaga agctgaaggg atcacccgag gacaatgagc agaagcagct gtttgtggag   5280
cagcacaagc actacctgga cgagatcatc gagcagatca gcgagttcag caagcgcgtg   5340
attctggcag acgcaaacct ggataaggtg ctgagcgcct acaacaagca ccgcgataag   5400
cccattcgcg agcaagcaga gaacatcatc cacctgttca ccctgaccaa cctgggagca   5460
cctgcagcat tcaagtactt cgacaccacc atcgaccgca agaggtacac aagcaccaag   5520
gaagtgctgg acgcaaccct gattcaccag agcattactg ggctgtacga gacacgcatc   5580
gacctgtcac aactgggagg ggactga                                        5607
```

```
<210> SEQ ID NO 62
<211> LENGTH: 588
<212> TYPE: DNA
<213> ORGANISM: Parachlorella sp.
<220> FEATURE:
<221> NAME/KEY: misc_feature
<223> OTHER INFORMATION: RPS17 promoter

<400> SEQUENCE: 62

caacacctag ttggtaaata ccgttgctga tattgctctg taccagtaaa agagggctgc     60
gatgagcgtt tttagtgcac ttcttcaaca cggaatattt ttcacaaatt ggtatgagaa    120
ccaattttgc aaaatgttcg ccctgtaaag tatcgctctg ggacgatcag cttgacgtaa    180
ttgtaggcga aaagggcgtt caaagtgcag ctttatgtat gaacgtcata aaatataaag    240
catagcacaa tcactgatag aaaatatttg tgcgcattaa aactctcact tctgttgcgg    300
atacaacgac ggaaatgaga agcttgtgta agaagcaatt caagttttca ttttgtcatc    360
taaggtgtga tcctccgata ttcattaccg aatgctgatc tgagttggaa agatggcaat    420
atttagctgt gcacactttg acctccaggc cttggcggga atttagtatt ctagctttcc    480
tattggaacg ataggccagc caagtctcca gcttgtatac gctacaccag cagacatgct    540
ctcaatttag ctgacagtgt cttcatattt gtattatctg ttgtgtct                 588
```

```
<210> SEQ ID NO 63
<211> LENGTH: 455
<212> TYPE: DNA
<213> ORGANISM: Parachlorella sp.
<220> FEATURE:
<221> NAME/KEY: misc_feature
<223> OTHER INFORMATION: RPS17 terminator

<400> SEQUENCE: 63

ggtgcgaata gtgcttcagt aaaaaagtag caacttggtg caatatcgtc agggtcgtgt     60
ggtctgctcg ccagcaagtt ttttggcaca ggagagcgct ttttccgagt accgccaaag    120
ttcaagcatg tgctgtgatt cgctgttgcc tcttatgata attgctcaaa gtttccaagc    180
attctatgtc caccctgcac cactaagttg tatggtgctt attctgcagg ggatgattca    240
tggtgcctaa aaattttgtg ctgctgtcgc gtctgttttc tgtcgcagtt tagtgaatgt    300
aactccaaat accaaacttt tcatcacaat catattgatg cctttgtaag tgaattacag    360
cgtttttttgc cataaaaaga agtaccgtga cattggggtc gtcataacaa gaagctttat   420
gaacaagcag cttgatctac gagacttata cataa                               455
```

```
<210> SEQ ID NO 64
<211> LENGTH: 2691
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Blasticidin resistance gene from Aspergillus
      terreus codon optimized for Parachlorella and containing
      Parachlorella introns

<400> SEQUENCE: 64

atggcaaaac ctctctccca ggaagagtct accctgattg aaagggcaac agcaaccatc     60

aacagcattc ccattagcga ggactactct gttgtgagtt ctgagaagct gattgttgtt    120

taacttcttt gaaagcttta tcgaagattc tgcaagcgat gaacattgct tgtcaagacc    180

gagagctgca tgcccacttg acatccagct ttgaacggct cttcatgttt gatttgtttc    240

tgattgtagg catctgcagc attgagctct gatggaagga tctttacagg agtgagtgca    300

gcgtcagctg tggcagttgt tggctttcgt ctcagtcagt agtttgctgg gattgattat    360

ggagggcaca gttgcaattt tgagttgcac gttgcgacaa gcgtgttgac aaagcgtggt    420

caagccggcc agtcttgccg gtggcgggtg gcttggtcta acttccgctc tacggcaatc    480

gttttgttca tggttacggg gctggcgtgc cagaaagtcc tggtcagcca ccctcgcttc    540

aaagccgtag cccaacaact ttgcgaatat gttcgatttg caggtgaacg tgtaccactt    600

tacaggagga ccttgtgcag aattggtggt gttaggtaca gctctgcgtg caacaggttg    660

caagatgcag cgcaggtctt ccctggtcaa acgatgtatg cagagttgag aggcacttga    720

gctgggtgaa tggcgtgggc tcgtaggtag tgtgcagggc aggaagggca gccaattttg    780

gagttgtggt ccggtgtcgt tgcttcgagc cttattagga ctcttgctca tcaaagcgtt    840

agttgtgaat aagttgatct gaaaggatgt tatgtacagc aagcagcagc agttaagagt    900

ctggggagta gctgcacagg gcgaggtgtc aagatgggaa gggtcctgcc tccttatgtg    960

tttttccctg taggggagga agcctcttat gggcaatggt tgggcatatt ttccagccag   1020

cccttctttc tataggggcc agggtgggcc cagctcgtct tggcttccac caccaggaga   1080

gtgagggcat tgaagggcca taaatagtcc tcccatctac gtgcaccaga gggtgtcgtc   1140

taggctgtgc atgccacgag gggaaggagc caagaatgag tgtatgggtt gttttcatgt   1200

ttaggctggg ataaaactgt tttcaattgc gcctgccggg tgaaaaccac agcagcatca   1260

gcaagcttgg agaaggccag cccgcccagc acaggctcac gttcccactc aggcggtcag   1320

tcgggcgggg gtgtgagtca ggcaggcgag ggtgtctgtg cctgacatca gcacctctgc   1380

ttagccactg cagcccctgg agcagggtag ggcgtcattt gcagcaatca cctgctgcct   1440

cacacgtcgc agcttggaat ttcaacgacc atcagcgctg gggttgttga gggatcatag   1500

cagattttgg tgcagcctgg ttgtcatgct ctttgtggaa tggcctctat gttcgagcaa   1560

ttcgttggat gttgaggtgc ttggggacag agagtcgaat gatgggccag ggtcaaacat   1620

gcgagcgttt ggctgagtca gcggtttttg ctggtcactt tttcttttgt ttcttattta   1680

ggtttgatgg atgtgttttg tgctgctgcc ctgaagctgc agcagcgtgt ctgccctgcg   1740

ctactgcggg caccaaggct atgtgctggt gcactcggct gcgctgcacc tgtgcacctc   1800

gcactccgtc cagcctccat gcagcacacg tactcacggt gtcctcctga cctgtcgtac   1860

gctattccaa acttgctctt ttgctgccgc tgctctcgta cacaattgct gttgattatc   1920
```

```
gatatctaat cgagcgcctg ctgactgaac tccgcaggta cagcagctgc agcagcagca   1980

ggaaatttga catgcattgt ggcaataggt gggtgggctc tgaaggagga ggagggagcg   2040

ggtgattaaa cagggcctgc atgaagagga gcaggggctg cgtggacagc agggggaagg   2100

tgcagaaggg agggtcaagc ggggttcagg tggctgtggg tttctgcacg agcagtgaaa   2160

gaagctgtat ccttccacct gcttccactg gcgaaaggtt gaaaacagga tgtcgcagct   2220

ggaaagatgt tgcgctgtca agtgcaagcc atggttgagg gtatgcctgt gtgcatgtgc   2280

ttcttaaagt tactcctgtt ctatggttct gggtgcttgt tgtttgtggt gcagggaacg   2340

agaatagggg gattttgtca ccttgcggaa gatgtagaca ggtgttgttg gatctgcatc   2400

ccgggattaa ggtgaggggg catgtaagca atggcaggca attcaagaac gaatcattgc   2460

tgcaaatgct gggatggtat gcagctgagg tatctattgc cttgtatttt gtctcgcatt   2520

gcatcggtgg tgcgttctgt ggcctgaggc acagttcttg ctgtttgata agggttcgac   2580

tgagttgtcg tgtgtgctgt gctgcaggca atcgtgaagg attcagatgg gcagcctaca   2640

gcagtgggaa ttagagaact gctgccttct gggtatgtgt gggaaggata a            2691
```

<210> SEQ ID NO 65
<211> LENGTH: 530
<212> TYPE: DNA
<213> ORGANISM: Parachlorella sp.
<220> FEATURE:
<221> NAME/KEY: misc_feature
<223> OTHER INFORMATION: RPS4 promoter

<400> SEQUENCE: 65

```
ccaccatggg ggaggtttga agtgtgcgcc tgatataatc atacacctaa aagcaccact     60

tgctgattgt gaagggacta tgtcgtttat gacgggacgt tacgctggcc gatggtttga    120

atttggacgc tgtggtagaa tgttatatgg acgtaaaggt tggcatattg aaaatcgtct    180

tcgcaggcaa acttctagac gtgtgaccca ccggtaaaac gacaagcgtg gcgcgtcgat    240

tgcgctttga acgtcgtttg ttggactcca gatgaacctc aaaatcaaag cggtgattga    300

cgaaaatcaa atgacagccc gcaaaatttc atcagccttc ggatcggatt ctcagaatct    360

gattgtccct gctggctaca tttatgaaat ttcgtacatt ttggcagaaa tgtcccaata    420

ccatagcact gccgcctgag ctcacccgag caatgcatac tgggtacctc gcccatctcg    480

ccctctttcc aagcccagtg ctgttgtaat agccaaaggg ctcagtaaca               530
```

<210> SEQ ID NO 66
<211> LENGTH: 546
<212> TYPE: DNA
<213> ORGANISM: Parachlorella sp.
<220> FEATURE:
<221> NAME/KEY: misc_feature
<223> OTHER INFORMATION: RPS4 terminator

<400> SEQUENCE: 66

```
gcatagcatc agcctgtggc agggttgtgg tagggctgag tggcagggtt aaaggggttg     60

cctaccccac ccctactctc atgacaccag caacagcagc agctcatgca gtactcaaat    120

cactgatgtc aatggtgtga cacatttggt taaggctgct ttttaaagtg ctgctttggg    180

ggcagtgact gtgcagagct tggagcgtat ccccatgtaa tcagaaccga cgagagttcg    240

gggcaacctt tcatcttcac attttttgtg atcagctaca gagtctgaaa tcaaatagag    300

gctgccatct aaacgcagga gtcacaacga aggcgaaaac tccaattgct gtactcaatg    360

cactaagtga ttgttcaatg gataaataca ctatgctcaa ttcatgccag cagagctgct    420
```

```
ccttccagcc agctacaatg gctttttcca cgccttttga agtatgaatg ttcagcttgc    480

tgtgcttgat gcatcaccat aaacacaatt ctacaacatt tcatgccaac aacagtacgg    540

gctttc                                                               546


<210> SEQ ID NO 67
<211> LENGTH: 572
<212> TYPE: DNA
<213> ORGANISM: Parachlorella sp.
<220> FEATURE:
<221> NAME/KEY: misc_feature
<223> OTHER INFORMATION: ACP1 promoter

<400> SEQUENCE: 67

agtttgcata gttaagtatg ctggctattg cagtacctta tatgcaaaca agtgctcaat     60

ctgtttcatc attgtctgtg ggcaaattgc ctgccaatat tctccagtta ttgcctgttg    120

tttcaaatga ttgaaattgg aagttgtatt gctctacatt tttgacttgt gatttttttca    180

tttgttgata tctgacaact gtgaactgca ctgaacttgc tgtgcttata aatgcatttt    240

tttgttttgg gccacgttga ttccttgtga tactttcctg ctatcaaacc aaaaatatac    300

tctcatgact gacgtgcaac aaatgcatgg aagctttcaa cgttacgaca gctgcttgcc    360

ccccatcagc tattctacat gtgtaaccta ccttgcatgg ccaccacaac gctactgcat    420

gcaagatctg gcgcaactgg atgtcccaat agtagaagta tccggattat ctccgagagt    480

tttacatatg taatcgacgc catttctgtc atcaactata aatccattgc tcctgcattt    540

ctggcactga cattctacca caagcaatac ca                                  572


<210> SEQ ID NO 68
<211> LENGTH: 869
<212> TYPE: DNA
<213> ORGANISM: Parachlorella sp.
<220> FEATURE:
<221> NAME/KEY: misc_feature
<223> OTHER INFORMATION: ACP1 terminator

<400> SEQUENCE: 68

gcagcagctt gttatgcctt ccccatgggc atcagcatgc tgcaagctgt ctagatatcc     60

agctttcagt ggaggttgag cgagggtcag cagcggttcc ctggcgatgg cggtcagctt    120

ttctggaagc cttcactagg actgcgccca gcgcatgtga cgccaatcga acttgtgtgc    180

aaggccaaat tttgtgaccc tgtgctgcac ttcatgtatt caagaattga gaagaaattt    240

cattgctgcc cttctttcac tttaatttcc atccctggat ccacctccca ccattgtggt    300

tgatgggtag gggttttggg taggtgcagt tcgttgtgca cgttgacatg tgtaacggtg    360

agcaaaggaa ttgctgggca agtagctatt gcagcttaag ggcatggtga aacacttgtg    420

ctgtatttac agaggaagcc agacaggtaa ggagtgtgtg gcagcttgga acaggagggc    480

tggtcgcaac aagtatgcat atcccatgat tgttgacata agagcagcag gtgcatattg    540

ccagcctttg tgaaagtgga ttgaaaatcg attagttggt gtgatagctg aggctaggca    600

ctgccaacct gcagtgaaat gaggctccaa gaccgggtaa taatacaggc aatcgaatcc    660

agttgaaatt acggcgatta aatccaagcg agcgttgtaa gaacatctgc acctgtctga    720

agtagtgagc ggataatgag cattgcttgc cttctatcac tatacctgac agttacgtgt    780

cacacactct caagcacaac acacagcggc aaagttactt gctaaacctc acagtcaagc    840

tgaaaataaa ggctaaatta cgtgagacc                                      869
```

<210> SEQ ID NO 69
<211> LENGTH: 1707
<212> TYPE: DNA
<213> ORGANISM: Parachlorella sp.
<220> FEATURE:
<221> NAME/KEY: misc_feature
<223> OTHER INFORMATION: Chloroplastic SRP54 coding sequence

<400> SEQUENCE: 69

```
atgcttcggc agcagctgtt gcacagcggc aggcagccgg gtgcgacatg cagcttacta     60
acctgctcga catggcgacc gtctgccttg ttcggccgtc ctaagcccca aaaactgcac    120
agccagcgct tgcagcatca gggccgcccc tcccgcctcg tcgtgcgcag cgcaatgttc    180
gacaacctga gccgcagcct ggagagggcg tgggacatgg tgcgcaagga cgggcggcta    240
acggcggaca acatcaagga gcccatgcgg gagattcgca gggcgctgct tgaggcggat    300
gtgaggctgg gggcgccgct gatcagattc ttggtatcta cccccccccc ctcccaggtc    360
tccctccccg tggtgcgcaa gtttgtgaag gcggtggagg agaaggcgct gggttctgca    420
gtgaccaagg gtgtcacccc cgaccagcag ctggtgaagg tggtgtacga ccagctgcgg    480
gagctgatgg gggggcagca ggaagggctg gtgcccactt cgccagagga gccgcaggtg    540
atcttgatgg cggggctgca gggcacgggg aagacgacag ctgcggggaa gctggccttg    600
ttcctgcaga agaaggggca gaaggtgctg ctggtggcca ccgacatcta ccgccccgcc    660
gccatcgacc agctggtgaa gctgggcgac aggatagggg tgccggtgtt ccagctggga    720
acccaggtgc agccgccgga gattgcaagg caggggctgg agaaggcgcg agcagagggg    780
tttgacgccg tcatcgtcga cacggcgggg cggctgcaga tcgaccagag catgatggag    840
gagctggtgc agatcaagtc cacggtgaag ccctccgaca cgctgctagt ggtcgatgcg    900
atgacggggc aggaggcagc cggctggtg aaggcgttca atgatgccgt ggacatcaca    960
ggcgccgtgc tgaccaagct tgacggggac agccgcggcg gcgccgcgct gagcgtgcgc   1020
caggtcagcg ggcggcccat caagtttgtg ggcatggggg agggcatgga ggcgctggag   1080
cccttctacc ccgagcgcat ggccagcagg attctgggca tgggtgacgt ggtcaccctg   1140
gtggagaagg ctgaggagag catcaaggaa gaggaggcgc aggagatatc gcggaagatg   1200
ctgtcggcca aatttgactt tgacgacttc ctgaagcagt acaagatggt ggcggggatg   1260
gggaacatgg cccaaatcat gaagatgctg ccaggcatga acaagtttac ggagaagcag   1320
ctggcgggcg ttgagaagca gtacaaggtg tacgagagca tgatccagag catgacggtg   1380
aaggagcgca agcagccgga gctgttggtg aagtcgccct ccaggaggcg gcgcatagcg   1440
cgcgggtcgg ggcgctcgga gcgggaggtc acagagctgc tgggggtgtt caccaacctg   1500
cggacgcaga tgcagagctt ctccaaaatg atggccatgg gggggatggg catgggctcc   1560
atgatgagcg acgaggagat gatgcaggcc acgctggcag gcgccggccc ccgccccgtg   1620
ccagctggca aggtgcggcg gaagaagctg gccgcggcgg gcgggtcgcg gggcatggct   1680
gagctggcat ccctgaaggc agaatga                                        1707
```

<210> SEQ ID NO 70
<211> LENGTH: 2667
<212> TYPE: DNA
<213> ORGANISM: Parachlorella sp.
<220> FEATURE:
<221> NAME/KEY: misc_feature
<223> OTHER INFORMATION: Bleomycin resistance gene codon optimized for Parachlorella and containing Parachlorella introns

<400> SEQUENCE: 70

```
atggccaaac tgacatccgc tgttcctgtg ttgacagcaa gagatgttgc aggtgcagtg     60
gagttttgtg agttctgaga agctgattgt tgtttaactt ctttgaaagc tttatcgaag    120
attctgcaag cgatgaacat tgcttgtcaa gaccgagagc tgcatgccca cttgacatcc    180
agctttgaac ggctcttcat gtttgatttg tttctgattg tagggacaga tagactgggg    240
tttagcaggg actttgtgga ggacgatttt gcaggagtgg tgagggatga tgtgacactg    300
tttatctcag cagtgcagga tcaagtgagt gcagcgtcag ctgtggcagt tgttggcttt    360
cgtctcagtc agtagtttgc tgggattgat tatggagggc acagttgcaa ttttgagttg    420
cacgttgcga caagcgtgtt gacaaagcgt ggtcaagccg gccagtcttg ccggtggcgg    480
gtggcttggt ctaacttccg ctctacagca atcgttttgt tcatggttac ggggctggcg    540
tgccagaaag tcctggtcag ccaccctcgc ttcaaagccg tagcccaaca actttgcgaa    600
tatgttcgat ttgcaggtgg tgcccgataa tacactggca tgggtttggg tgagaggtac    660
agctctgcgt gcaacaggtt gcaagatgca gcgcaggtct tccctggtca aacgatgtat    720
gcagagttga gaggcacttg agctgggtga atggcgtggg ctcgtaggta gtgtgcaggg    780
caggaagggc agccaatttt ggagttgtgg tccggtgtcg ttgcttcgag ccttattagg    840
actcttgctc atcaaagcgt tagttgtgaa taagttgatc tgaaaggatg ttatgtacag    900
caagcagcag cagttaagag tctggggagt agctgcacag ggcgaggtgt caagatggga    960
agggtcctgc ctccttatgt gtttttccct gtaggggagg aagcctctta tgggcaatgg   1020
ttgggcatat tttccagcca gcccttcttt ctataggggc cagggtgggc ccagctcgtc   1080
ttggcttcca ccaccaggag agtgagggca ttgaagggcc ataaatagtc ctcccatcta   1140
cgtgcaccag agggtgtcgt ctaggctgtg catgccacga ggggaaggag ccaagaatga   1200
gtgtatgggt tgttttcatg tttaggctgg gataaaactg ttttcaattg cgcctgccgg   1260
gtgaaaacca cagcagcatc agcaagcttg gagaaggcca gcccgcccag cacaggctca   1320
cgttcccact caggcggtca gtcgggcggg ggtgtgagtc aggcaggcga gggtgtctgt   1380
gcctgacatc agcacctctg cttagccact gcagcccctg gagcagggta gggcgtcatt   1440
tgcagcaatc acctgctgcc tcacacgtcg cagcttggaa tttcaacgac catcagcgct   1500
ggggttgttg agggatcata gcagattttg gtgcagcctg gttgtcatgc tctttgtgga   1560
atggcctcta tgttcgagca attcgttgga tgttgaggtg cttggggaca gagagtcgaa   1620
tgatgggcca gggtcaaaca tgcgagcgtt tggctgagtc agcggttttt gctggtcact   1680
ttttcttttg tttcttattt aggtttgatg gatgtgtttt gtgctgctgc cctgaagctg   1740
cagcagcgtg tctgccctgc gctactgcgg gcaccaaggc tatgtgctgg tgcactcggc   1800
tgcgctgcac ctgtgcacct cgcactccgt ccagcctcca tgcagcacac gtactcacgg   1860
tgtcctcctg acctgtcgta cgctattcca aacttgctct tttgctgccg ctgctctcgt   1920
acacaattgc tgttgattat cgatatctaa tcgagcgcct gctgactgaa ctccgcaggt   1980
ttggatgaac tgtatgcaga gtggtctgaa gtggtgagca ccaactttag gtgggtgggc   2040
tctgaaggag gaggagggag cgggtgatta aacagggcct gcatgaagag gagcaggggc   2100
tgcatggaca gcagggggaa ggtgcagaag ggagggtcaa gcggggttca ggtggctgtg   2160
ggtttctgca cgagcagtga aagaagctgt atccttccac ctgctttcac tggcgaaagg   2220
ttgaaaacag gatgtcgcag ctggaaagat gttgcgctgt caagtgcaag ccatggttga   2280
gggtatgcct gtgtgcatgt gcttcttaaa gttactcctg ttctatggtt ctgggtgctt   2340
```

-continued

```
gttgtttgtg gtgcagggat gcaagcggac ctgcaatgac agagattgga gaacaacctt   2400

ggggaaggga gtttgcattg agagatcctg caggtgaggg ggcatgtaag caatggcagg   2460

caattcaaga acgaatcatt gctgcaaatg ctgggatggt atgcagctga ggtatctatt   2520

gccttgtatt ttgtctcgca ttgcatcggt ggtgcgttct gtggcctgag gcacagttct   2580

tgctgtttga taagggttcg actgagttgt cgtgtgtgct gtgctgcagg caattgcgtg   2640

cactttgttg cagaagaaca ggactga                                       2667


<210> SEQ ID NO 71
<211> LENGTH: 32
<212> TYPE: DNA
<213> ORGANISM: Artificial Sequence
<220> FEATURE:
<223> OTHER INFORMATION: Synthetic

<400> SEQUENCE: 71

tgcgacatgc agcttactaa cctgctcgac at                                   32


<210> SEQ ID NO 72
<211> LENGTH: 28
<212> TYPE: DNA
<213> ORGANISM: Artificial Sequence
<220> FEATURE:
<223> OTHER INFORMATION: Synthetic

<400> SEQUENCE: 72

atgggctcct tgatgttgtc cgccgtta                                        28


<210> SEQ ID NO 73
<211> LENGTH: 21
<212> TYPE: DNA
<213> ORGANISM: Artificial Sequence
<220> FEATURE:
<223> OTHER INFORMATION: Synthetic

<400> SEQUENCE: 73

acccaaaccc atgccagtgt a                                               21


<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74

actgtatgca gagtggtctg aagtg                                           25
```

ALGAL CHLOROPLASTIC SRP54 MUTANTS

CROSS-REFERENCE TO RELATED APPLICATIONS

This application claims benefit of priority under 35 U.S.C. § 119(e) of U.S. Ser. No. 62/148,071, filed Apr. 15, 2015, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI1880_1WO_Sequence_Listing.txt, was created on 15 Apr. 2016, and is 172 kb. The file can be assessed using Microsoft Word on a computer that uses Windows OS.

BACKGROUND OF THE INVENTION

The present invention relates to algal strains having increased photosynthetic efficiency and productivity and to their use in producing products under photoautotrophic conditions.

The productivity of photosynthetic algal cultures depends on the ability of the algae to efficiently utilize available light. In large scale cultures, the efficiency of light utilization is reduced by self-shading as the cell density of the culture increases. Self-shading within cultures is further increased by the tendency of individual cells to maximize their light harvesting antennae in response to increasingly limited light, causing further reduction in the ability of available light to penetrate into the culture (Formighieri et al. (2012) *J. Biotechnol* 162:113-123). In such cultures, the light absorbed at the uppermost level of the culture is in excess of the amount that can be utilized by the algal cells. The excess light energy absorbed by the upper layer of cells is dissipated by nonphotochemical quenching (NPQ) mechanisms, while cells beneath the upper layer receive suboptimal light.

U.S. Patent Application Publication No. US2014/0220638 describes a screen for mutants having increased photosynthetic efficiency that have a locked-in high light acclimated (LIHLA) phenotype and mutants isolated using the screen. LIHLA mutants are deregulated in low light acclimation, that is, they do not substantially increase their light harvesting antennae when transferred from high to low light, allowing light to penetrate to greater culture depth.

The light harvesting antennae of higher plants and many algae, including, among others, green algae, diatoms, and eustigmatophytes, consists of chlorophyll molecules bound by light harvesting chlorophyll binding proteins, or LHCPs. The LHCPs are encoded by nuclear genes and are post-translationally transported into the chloroplast. Once inside the chloroplast, the LHCs are inserted into the thylakoid membranes by their interaction with a chloroplastic signal recognition particle (SRP) complex that includes the polypeptides cpSRP43 and cpSRP54. cpSRP43 binds the imported LHCP and acts as a chaperonin to maintain the solubility of the LHCP prior to its assembly into the membrane. cpSRP54 (chloroplastic signal recognition particle 54 kilodalton polypeptide) is homologous to both eukarotic cytosolic SRP54 and the prokaryotic SRP54-homologous Ffh protein that mediates protein translocation into and across cell membranes. The LHCP-SRP complex interacts with the thylakoid protein insertion machinery in the chloroplast (cpFTSY, the chloroplastic SRP receptor, and ALB3.1, a thylakoid insertase, both of which, like cpSRP54, are encoded by nuclear genes), to insert the LHCP into the thylakoid membrane (Kirst & Melis (2014) *Biotechnol Adv* 32:66-72). Mutants in green algae (chlorophytes) displaying reduced antenna size have been isolated that have reduced or eliminated expression of, independently, the cpSRP43 gene, the ALB3.1 gene, and the CpFTSY gene (Bellafiore et al. (2002) *The Plant Cell* 14:2303-2314; Kirst et al. (2012) *Plant Physiol* 158:930-945; Kirst et al. (2012) *Plant Physiol* 160:2251-2260). The algal knockout mutants of the ALB3.1, CpFTSY, and cpSRP43 genes are reported to be leaky however, resulting in some assembly of the LHC proteins into the thylakoid, indicating possible functional overlap among these proteins (Kirst & Melis (2014) supra). No cpSRP54 mutants have been isolated in algae.

SUMMARY OF THE INVENTION

As described in the Examples herein, mutants of a green algal (Chlorophyte) *Parachlorella* strain that are impaired in their ability to increase their light harvesting antennae in response to low light were isolated. Genome analysis of these mutants revealed that several isolates have lesions in the cpSRP54 gene. These mutants exhibit enhanced photosynthetic efficiency and also demonstrate improved biomass productivity in assays in which the algae are exposed to continuous bright light as well as when assayed under a diel cycle light regimen that simulates outdoor pond light conditions. Further, a cytosolic SRP54 mutant in *Nannochloropsis*, a Eustigmatophyte alga, was found to have increased lipid productivity with respect to wild type cells A first aspect of the invention is an algal mutant that has a mutated or attenuated cpSRP54 gene. The mutant can be a classically-derived mutant or can be a recombinant alga. In some examples a mutant as provided herein that has a mutated or attenuated cpSRP54 gene can be obtained by chemical, UV, or gamma irradiation mutagenesis and screened for reduced chlorophyll under low light conditions using methods disclosed herein. Alternatively the mutant can be obtained by transformation with a nucleic acid construct that can insert in a non-targeted fashion into the genome to disrupt genes. In additional examples, a mutant having an altered, disrupted, or attenuated cpSRP54 gene can be an engineered mutant in which a gene encoding a cpSRP54 is targeted for mutation to result in a truncated, altered, deleted, or disrupted cpSRP54 gene. In some examples the mutated cpSRP54 gene is not mutated within the sequence encoding the first 169 amino acids of the GTPase domain of the cpSRP54 polypeptide. In some examples, a construct targeting expression of the cpSRP54 gene, such as, for example, an antisense construct, RNAi construct, or ribozyme construct, is introduced into an algal cell to reduce expression of the cpSRP54 gene. In additional examples, an engineered strain can be a strain in which a gene encoding cpSRP54 is knocked out, disrupted, or altered by homologous recombination or by genome editing, for example, using a TALEN or a cas/CRISPR system.

An algal mutant having a mutated cpSRP54 gene or attenuated expression of a cpSRP54 gene can have one or more of the following traits with respect to a control algal strain: total chlorophyll reduced by at least 20%, for example, reduced by at least 30%, at least 40%, at least 50%, at least 60%, or at least 65%; a chlorophyll a:b ratio (for chlorophyte and charophyte algal mutants) that is increased by at least 20%, for example, by at least 25%, at least 30%, at least 40%, at least 50%, at least 60%, at least 70%, or at least 80%; higher photochemical quenching (qP) at all physiological light intensities greater than about 250 μmol photons $m^{-2}$ $sec^{-1}$, e.g., at all physiological light intensities greater than 150 μmol photons $m^{-2}$ $sec^{-1}$, greater than 75 μmol photons $m^{-2}$ $sec^{-1}$, or greater than 40 μmol photons $m^{-2}$ $sec^{-1}$ and up to about 2800 μmol photons $m^{-2}$ $sec^{-1}$; decreased nonphotochemical quenching (NPQ) at all physiological light intensities greater than 250 μmol photons $m^{-2}$ $sec^{-1}$, e.g., at all physiological light intensities greater than 150 μmol photons $m^{-2}$ $sec^{-1}$, greater than 75 μmol photons $m^{-2}$ $sec^{-1}$, or greater than 40 μmol photons $m^{-2}$ $sec^{-1}$ and up to about 2800 μmol photons $m^{-2}$ $sec^{-1}$; higher rates of electron transport through photosystem II (ETR(II)) at all physiological light intensities greater than about 250 μmol photons $m^{-2}$ $sec^{-1}$, e.g., greater than 150 μmol photons $m^{-2}$ $sec^{-1}$, greater than 75 μmol photons $m^{-2}$ $sec^{-1}$, or greater than 40 μmol photons $m^{-2}$ $sec^{-1}$ and up to about 2800 μmol photons $m^{-2}$ $sec^{-1}$; and greater photosynthetic efficiency (Y(II)) at all physiological light intensities greater than 250 μmol photons $m^{-2}$ $sec^{-1}$ e.g., greater than 150 μmol photons $m^{-2}$ $sec^{-1}$, greater than 75 μmol photons $m^{-2}$ $sec^{-1}$, or greater than 40 μmol photons $m^{-2}$ $sec^{-1}$ and up to about 2800 μmol photons $m^{-2}$ $sec^{-1}$. In some exemplary embodiments, an algal mutant having a mutated or attenuated cpSRP54 gene can have all of the following traits with respect to a control algal strain: total chlorophyll reduced by at least 20%, increased chlorophyll a:b ratio (for chlorophyte or charyophyte algae) by at least 20%, and higher photochemical quenching (qP), decreased NPQ, higher rates of electron transport through photosystem II (ETR(II)), and greater photosynthetic efficiency (Y(II)) at all physiological light intensities greater than 250 μmol photons $m^{-2}$ $sec^{-1}$ and up to about 2800 μmol photons $m^{-2}$ $sec^{-1}$.

In any of the examples or embodiments set for the herein, comparisons with a control alga refer to comparisons with an alga that is substantially identical in all relevant respects to the mutant alga described and cultured and tested under identical conditions as described for the mutant alga, with the exception that the control alga does not have a mutated or attenuated SRP54 gene. For example, a control alga is of the same species and, with the exception of alterations to the cpSRP54 or cytosolic SRP54 gene or constructs for attenuating the cpSRP54 or cytosolic SRP54 gene present in the mutant, is genetically identical with the exception of small genome changes (e.g., "SNPs") that do not affect cell physiology that may be incurred during mutagenesis through normal propagation. In various embodiments a control alga is a strain from which the mutant alga having attenuated expression of a cpSRP54 gene, or is a strain from which the mutant alga having attenuated expression of a cytosolic SRP54 gene is derived.

An algal mutant having a mutated cpSRP54 gene or an attenuated cpSRP54 gene can also have a higher rate of oxygen evolution than a control algal cell on a per chlorophyll basis. For example, an algal cpSRP54 mutant as provided herein can have at least 50%, at least 100%, at least 200%, at least 300%, or at least 400% greater oxygen evolution per mg chlorophyll with respect to a control alga. An algal mutant having a mutated cpSRP54 gene or an attenuated cpSRP54 gene can also have a higher rate of carbon fixation than a control algal cell on a per chlorophyll basis. For example, an algal cpSRP54 mutant as provided herein can have at least a 50%, at least a 60%, at least an 80%, or at least a 100% increase in the rate of carbon fixation per mg chlorophyll with respect to a control alga.

Further, an algal cpSRP54 mutant, i.e., an algal strain as provided herein having attentuated expression of a cpSRP54 gene or an altered or disrupted cpSRP54 gene can exhibit greater biomass productivity as compared with a control strain under diel cycle conditions. For example, an algal cpSRP54 mutant as provided herein can demonstrate greater biomass productivity when cultured under a diel cycle in which the light intensity changes throughout the light period to mimic exposure to natural light, under a diel cycle in which the light period has a constant light intensity, and under constant light.

The cpSRP54 gene that is mutated or whose expression is attenuated in an algal mutant as provided herein can be identified by homology to known cpSRP54 genes, and can include an SRP54 GTPase domain, and an SRP signal binding (SB) domain, and in some examples, further includes an N-terminal helical bundle domain. In nonlimiting examples, a cpSRP54 gene that is mutated or whose expression is attenuated can encode a polypeptide that has at least 50%, at least 55%, at least 60%, at least 65%, at least 70%, at least 75%, at least 80%, at least 85%, at least 90%, or at least 95% identity to any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:12, SEQ ID NO:13, or SEQ ID NO:14. Alternatively or in addition, the cpSRP54 gene that is mutated or whose expression is attenuated in an algal mutant as provided herein can be a gene encoding a GTPase domain (e.g., an SRP GTPase domain) having at least 60%, at least 65%, at least 70%, at least 75%, at least 80%, at least 85%, at least 90%, or at least 95% identity to any of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:25, SEQ ID NO:26, or SEQ ID NO:27. In some examples the mutated cpSRP54 gene is not mutated within the sequence encoding the first 165, 166, 167, 168, or 169 amino acids of the GTPase domain of the cpSRP54 polypeptide or is not mutated within the sequence encoding the GTPase domain.

An alga strain that has a mutated cpSRP54 gene can be any type of alga, and can be, as nonlimiting examples, a member of the green algae (chlorophytes), charophytes, or a member of the chromophytes, and can be a member of the diatoms (e.g., members of the bacillariophceae, coscinodisophyceae, or fragilariophyceae), pelagophytes, prasinophytes, glaucophytes, chlorarachniophytes, euglenophytes, eustigmatophytes, chromophytes, xanthophytes (yellow-green algae), or dinoflagellates. As nonlimiting examples, algal species used in the invention herein can be members of any of the genera *Amphora, Ankistrodesmus, Aplanochytrium, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chroomonas, Chrysophyceae, Chrysosphaera, Cricosphaera, Crypthecodinium, Cryptomonas, Cyclotella, Cyanidioschyzon, Desmodesmus, Dunaliella, Elina, Ellipsoidon, Emiliania, Eremosphaera, Ernodesmius, Euglena, Eustigmatos, Fragilaria, Fragilariopsis, Franceia, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spyrogyra, Staurastrum, Stichococcus, Tetrachlorella, Tetraselmis,*

*Thalassiosira, Tribonema, Vaucheria, Viridiella, Vischeria*, and *Volvox*. In some embodiments, an algal mutant as provided herein having attenuated expression of a cpSRP54 gene is a member of the chlorophytes or charophytes, and may be, for example, a member of any of the Chlorophyte classes Chlorophyceae, Trebouxiophyceae, Chlorodendrophyceae, Ulvophyceae, Pedinophyceae, or Prasinophyceae. For example, the algal mutant having attenuated expression of a cpSRP54 gene can be a species belonging to Chlorophyceae, Trebouxiophyceae, or Chlorodendrophyceae. In some embodiments, the mutant algal cell is a Chlorophyte algal cell, and may be a Chlorophyte algal cell of the Trebouxiophyceae class, for example, an algal cell of a species of a genus such as *Botryococcus, Chlorella, Auxenochlorella, Heveochlorella, Marinichlorella, Parachlorella, Pseudochlorella, Tetrachlorella, Eremosphaera, Franceia, Micractinium, Nannochloris, Oocystis, Picochlorum*, or *Prototheca*. In some aspects, the mutant alga having attenuated expression of a chloroplastic SRP54 gene can be a species belonging to a species of *Auxenochlorella, Chlorella, Heveochlorella, Marinichlorella, Parachlorella, Pseudochlorella* or *Tetrachlorella*.

Another aspect of the invention is a nucleic acid molecule comprising a nucleic acid sequence encoding a polypeptide having at least 80%, at least 85%, at least 90%, or at least 95% identity to SEQ ID NO:2. The polypeptide having at least 80% identity to SEQ ID NO:2 or SEQ ID NO:11 can include an amino acid sequence having at least 80%, at least 85%, at least 90%, or at least 95% identity to SEQ ID NO:15. The nucleic acid molecule in various examples can be or comprise a cDNA that lacks one or more introns present in the naturally-occurring gene. The nucleic acid molecule in various examples can have a sequence that is not 100% identical to a naturally-occurring gene. The nucleic acid molecule in various examples can comprise a heterologous promoter operably linked to the sequence encoding a polypeptide having at least 80%, at least 85%, at least 90%, or at least 95% identity to SEQ ID NO:2 and/or can comprise a vector that includes a sequence encoding a polypeptide having at least 80%, at least 85%, at least 90%, or at least 95% identity to SEQ ID NO:2.

A further aspect of the invention is a construct designed for attenuating expression of a gene encoding a cpSRP54 polypeptide. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring cpSRP54 gene of an alga or sequences adjacent thereto. For example, the construct can include at least a portion of a cpSRP54 gene, e.g., a sequence homologous to at least a portion of an cpSRP54 gene that encodes a polypeptide having at least 50%, at least 55%, at least 60%, at least 65%, at least 70%, at least 75%, at least 80%, at least 85%, at least 90%, or at least 95% identity to any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:14. The construct can include, for example, at least a portion of the coding region of a cpSRP54 gene, at least a portion of an intron of a cpSRP54 gene, at least a portion of a 5'UTR of a cpSRP54 gene, at least a portion of the promoter region of a cpSRP54 gene, and/or at least a portion of a 3' UTR of a cpSRP54 gene. In some examples, the construct can be an RNAi, ribozyme, or antisense construct and can include a sequence from the transcribed region of the cpSRP54 gene in either sense or antisense orientation. In further examples a construct can be designed for the in vitro or in vivo expression of a guide RNA designed to target a cpSRP54 gene, and can include a sequence homologous to a portion of a cpSRP54 gene, including, for example, an intron, a 5'UTR, a promoter region, and/or a 3' UTR of a cpSRP54 gene. In yet further examples, a construct for attenuating expression a gene encoding a cpSRP54 polypeptide can be a guide RNA or antisense oligonucleotide, where the sequence having homology to a transcribed region of a cpSRP54 gene in antisense orientation.

Yet another aspect of the invention is a method of producing biomass or at least one algal product using a mutant alga of the invention. The methods can include culturing the alga having a mutant or attenuated cpSRP54 gene as provided herein to produce biomass or a product such as but not limited to one or more lipids, a polymer, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant. The method optionally further includes isolating at least one product from the culture. The mutant can produce more biomass or more of the algal product than is produced by a culture of a control microorganism that does not have a mutated or attenuated cpSRP54 gene. The mutant alga can be cultured phototrophically and can be cultured in a pond or raceway. Also provided is a product made by an algal mutant as disclosed herein. Further included herein is an algal biomass comprising a mutant alga having a mutated or attenuated cpSRP54 gene.

A further aspect of the invention is a mutant microorganism having attenuated expression of a gene encoding a gene encoding a cytosolic SRP54 polypeptide, where the mutant microorganism produces more lipid than a control microorganism that does not have attenuated expression of the cytosolic SRP54 gene. A mutant as provided herein is a mutant generated by human manipulation, for example, a mutant obtained by classical mutagenesis using chemicals, UV irradiation, or gamma irradiation, or a mutant obtained by genetic engineering, for example, gene disruption, gene insertion, homologous recombination, antisense constructs, ribozymes, RNAi, or genome editing using TALENs or RNA-guided endonucleases, for example. The mutant microorganism having attenuated expression of a gene encoding a gene encoding a cytosolic SRP54 polypeptide can be a photosynthetic microorganism, such as an alga, can be, for example a Chlorophyte, Charyophyte, Eustigmatophyte, or Bacillariophyte alga. In some embodiments the mutant microorganism can be a eukaryotic alga of the Bacillariophyte class, such as, for example, *Achnanthes, Amphora, Amphiprora, Chaetoceros, Cyclotella Cylindrotheca, Fragilaria, Fragilariopsis, Navicula, Nitzschia, Phaeodactylum, Skeletonema*, or *Thalassiosira*. In other embodiments the eukaryotic microagla having attenuated expression of a gene encoding a cytosolic SRP54 polypeptide is a eukarytoic microalga of the Eustigmatophyte class, and can be, for example, a species of *Ellipsoidion, Eustigmatos, Monodus, Nannochloropsis, Pseudostaurastrum*, or *Vischeria*. For example, in some embodiments the mutant that has attenuated expression of a cytosolic SRP54 polypeptide and demonstrates increased lipid productivity with respect to a control alga can be a species of *Nannochloropsis*. The mutant microorganism can have expression of the gene encoding a cytosolic SRP54 polypeptide that is reduced but not eliminated with respect to a control microorganism, that is, some amount of functional protein is made that is less than the amount of functional protein made by a control or wild type microorganism or the mutant having attenuated expression of the gene encoding a cytosolic SRP54 polypeptide can lack a functional cytosolic SRP54 polypeptide, for example, due to mutation such as but not limited to, introduction of a stop codon or reading frame shift or deletion of all or a portion of the gene such that essentially no functional protein is made. In some embodiments the mutant microorganism has attenuated expression of a cytosolic SRP54 gene that (in non-mutated form) encodes a polypeptide having at least 50%, at least 55%, at least 60%, at least 65%, at least 70%, at least 75%, at least 80%, at least 85%, at least 90%, or at least 95% identity to SEQ ID NO:30. Alternatively or in addition, a mutant microorganism that has attenuated expression of a cytosolic SRP54 gene can have attenuated expression of a gene whose coding sequence has at least 40%, at least 45%, at least 50%, at least 55%, at least 60%, at least 65%, at least 70%, at least 75%, at least 80%, at least 85%, at least 90%, or at least 95% identity to SEQ ID NO:29.

Further provided is a method of making lipid using a mutant microorganism having attenuated expression of a gene encoding a gene encoding a cytosolic SRP54 polypeptide. The mutant microorganism can be any disclosed herein. The method includes: culturing a mutant microorganism having attenuated expression of a gene encoding a gene encoding a cytosolic SRP54 polypeptide under conditions in which the mutant microorganism produces lipid. In various embodiments the method includes isolating at least one lipid from the microorganism, the culture medium or both. In various examples the mutant microorganism produces more lipid that a control microorganism substantially identical to the mutant microorganism having attenuated expression of a cytosolic SRP54 gene. The culture can be a batch, semi-continuous, or continuous culture, and in various embodiments the culture conditions are nitrogen replete. In various embodiments the culture conditions are nutrient replete. The culture conditions can be photoautotrophic, for example, the culture medium can lack an added sugar, organic acid, or other reduced carbon source able to be metabolized by the algal microorganism and can include inorganic carbon (e.g., carbonic acid, a carbonate salt, or carbon dioxide) as substantially the sole source of carbon for incorporation into cellular products such as lipid.

These and other objects and features of the invention will become more fully apparent when the following detailed description of the invention is read in conjunction with the accompanying drawings.

BRIEF DESCRIPTION OF THE DRAWINGS

FIGS. 2A-2C FIG. 2A) shows the readout from flow cytometry performed on a host cell line transformed with construct pSGE6202 that demonstrates full penetrance (single peak, shifted to the right with respect to control). FIG. 2B) shows the readout from flow cytometry performed on a host cell line transformed with construct pSGE6202 that does not demonstrate full penetrance (two peaks, one of which is coincident with control peak); FIG. 2C) is a Western blot of pSGE-6206 transformants with an antibody that recognizes the FLAG-tagged cas9 protein.

FIGS. 3A-3B FIG. 3A) is a graph showing the amount of chlorophyll per unit biomass of various SRP pathway *Nannochloropsis* mutants; FIG. 3B) provides the amount of chlorophyll per cell for the same mutants. GE-14792, cytosolic SRP54 knockout; GE-15272, chloroplastic Ftsy knockout; GE-15274, chloroplastic SRP54 (cpSRP54) knockout; GE-15315, Alb3 knockout.

FIGS. 4A-4B FIG. 4A) provides photosynthesis (oxygen evolution) versus light intensity curves (P-I curves) for the SRP pathway mutants, and FIG. 4B) provides the maximal photosynthesis rate ($O_2$ evolution) for each of the mutants. GE-14792, cytosolic SRP54 knockout; GE-15272, chloroplastic Ftsy knockout; GE-15274, chloroplastic SRP54 (cpSRP54) knockout; GE-15315, Alb3 knockout.

FIGS. 5A-5B FIG. 5A) provides a comparison of Pmax as assessed by 14C incorporation assays for various SRP pathway mutants, and FIG. 5B) provides the average total organic carbon (TOC) productivity of the mutants over a week-long culture period. GE-14792, cytosolic SRP54 knockout; GE-15272, chloroplastic Ftsy knockout; GE-15274, chloroplastic SRP54 (cpSRP54) knockout; GE-15315, Alb3 knockout.

FIGS. 6A-6B FIG. 6A) provides the average lipid (FAME) productivity of the mutants over the same day culture period as shown in FIG. 5B, and FIG. 6B) provides the FAME/TOC values over the course of the assay. GE-14792, cytosolic SRP54 knockout; GE-15272, chloroplastic Ftsy knockout; GE-15274, chloroplastic SRP54 (cpSRP54) knockout; GE-15315, Alb3 knockout.

FIGS. 7A-7B FIG. 7A) is a graph of maximum quantum yield (Fv/Fm) in response to increasing light intensity in *Parachlorella* cpSRP54 mutants NE-07542, NE-07548, NE-07557, NE-07564, and NE-07837, and FIG. 7B) is a graph of photochemical quenching (qP) in response to increasing light intensity in cpSRP54 mutants NE-07542, NE-07548, NE-07557, NE-07564, and NE-07837.

FIGS. 9A-9B FIG. 9A) is a graph showing electron transport rates through photosystem II (ETR(II)) in cpSRP54 mutants NE-07542, NE-07548, NE-07557, NE-07564, and NE-07837, and FIG. 9B) is a graph of photosynthetic efficiency (Y(II)) in response to increasing light intensity in cpSRP54 mutants NE-07542, NE-07548, NE-07557, NE-07564, and NE-07837.

FIGS. 12A-12B FIG. 12A) is a graph of biomass (total organic carbon) produced on successive days in a semicontinuous CL2000 assay culture of cpSRP54 mutant NE-07557 (diamonds) and wild-type (squares). Each point represents the TOC average of three cultures. FIG. 12B) is a graph of biomass (total organic carbon) produced on successive days in a semicontinuous HL2000 assay culture of cpSRP54 mutant NE-07557 (diamonds) and wild-type (squares). Each point represents the TOC average of three cultures.

FIGS. 13A-13B FIG. 13A) is a graphic depiction of the light intensity used during the light period of the SPCA assay over the course of the day (x axis), and FIG. 13B) is a graph of biomass (total organic carbon) produced on successive days in a semicontinuous assay (SCPA) culture of cpSRP54 mutant NE-07837 (diamonds) and wild-type (squares). The light varied in intensity throughout the day to mimic natural sunlight. Each point represents the TOC average of three cultures.

DETAILED DESCRIPTION OF THE INVENTION

Figure 1:
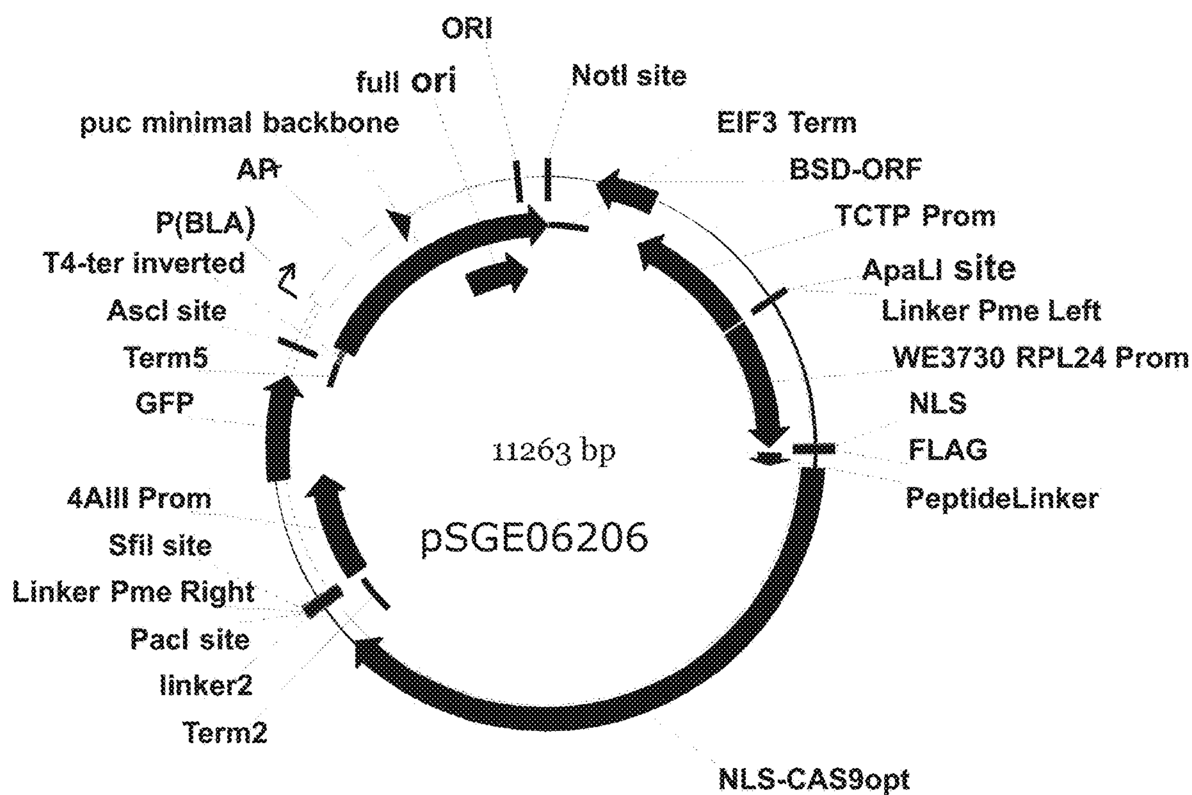
FIG. 1 is a diagram of vector pSGE-6206 that includes a Cas9 protein codon optimized for *Nannochloropsis* that includes a nuclear localization sequence (NLS). Vector pSGE-6206 also includes a GFP gene.

Unless defined otherwise, all technical and scientific terms used herein have the same meaning as commonly understood by one of ordinary skill in the art to which this invention is related. Many of the techniques and procedures described or referenced herein are well understood and commonly employed using conventional methodology by those skilled in the art. The following terms are defined for purposes of the invention as described herein.

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

As used in the present disclosure and claims, the singular forms "a," "an," and "the" also include plural forms unless the context clearly dictates otherwise.

All ranges provided within the application are inclusive of the values of the upper and lower ends of the range.

The term "and/or" as used in a phrase such as "A and/or B" herein is intended to include "A and B", "A or B", "A", and "B".

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid that comprises a gene or a portion thereof can be a coding (sense) strand or a non-coding (antisense) strand.

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation), having decreased expression due to alteration or disruption of gene regulatory sequences, or may be a gene targeted by a construct that reduces expression of the gene, such as, for example, an antisense RNA, microRNA, RNAi molecule, or ribozyme.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or exogenous recombinant nucleic acid sequence into the organism, and includes gene knockouts, targeted mutations, gene replacement, and promoter replacement, deletion, or insertion, as well as introduction of transgenes or synthetic genes into the organism. Recombinant or genetically engineered organisms can also be organisms into which constructs for gene "knock down" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided herein in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that has arisen spontaneously or is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; can be a gene that has one or more point mutations leading to a change in the amino acid of the encoded protein or results in aberrant splicing of the gene transcript, etc.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 27.0 (March 2013) based on the UniProt protein database release 2012_06. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

When referring to a photosynthetic organism, such as an algal, the term "acclimated to low light" means having the increased chlorophyll and photosynthetic properties of the photosynthetic organism after being exposed to a low light intensity for a period of time that is sufficient for changes in chlorophyll and photosynthetic properties to stabilize at the low light condition. Low light can be for example, less than 200 $\mu E \cdot m^{-2} \cdot s^{-1}$ and preferably about 100 $\mu E \cdot m^{-2} \cdot s^{-1}$ or less or 50 $\mu E \cdot m^{-2} \cdot s^{-1}$ or less, and the period of time for acclimation can be for at least about four hours, at least about six hours, at least about eight hours, or at least about twelve hours, at least 24 hours, or at least 48 hours, and may be as long as 2, 3, 4, or 5 days.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

An algal mutant "deregulated in low light acclimation" (or a "Locked in High Light Acclimation" or LIHLA mutant) is a mutant that does not exhibit the changes in phenotype and gene expression that are characteristic of a low light acclimated wild type algal cell, including: a substantial increase in chlorophyll and a substantial increase in the expression of the majority of light harvesting complex protein (LHCP) genes. An algal mutant deregulated in low light acclimation, when acclimated to low light, has decreased expression with respect to low light acclimated wild type cells, of multiple genes (for example, at least ten, at least twenty, at least thirty, at least forty or at least fifty genes) that are upregulated during low light acclimation of wild type cells. Further, an algal mutant deregulated in low light acclimation has increased expression of genes with respect to low light acclimated wild type cells (for example, at least five, at least six, at least seven, at least eight, at least nine, or at least ten genes) that are downregulated during low light acclimation of wild type cells. Further, as disclosed herein, an algal mutant deregulated in low light acclimation may have photosynthetic properties that are significantly different than the photosynthetic properties of wild type cells when both mutant and wild type cells are acclimated to low light.

"Photosynthetic properties", "photosynthetic properties", "photophysiological properties", or photophysiological parameters" include, without limitation, maximal photosynthetic rate, $P_{max}$ (calculated on a per cell or per mg chlorophyll basis), the intensity at which photosynthesis saturates, Ek, as measured by oxygen evolution, and a ("alpha") the initial slope of the photosynthesis (oxygen evolution) versus irradiance intensity (P/I) curve. Additional photosynthetic properties include various parameters that can be measured using fluorescence detection, including, for example, photosynthetic efficiency, Fv/Fm; the photosynthetic quantum yield of photosystem II (PSII), $\phi$PSII; photochemical quenching, or the proportion of open PSII centers, qP; nonphotochemical quenching, NPQ; PSII electron transport rate, $ETR_{PSII}$; PSI electron transport rate, $ETR_{PSI}$; cross-sectional size of PSI, and cross-sectional size of PSII. The listing here is not exhaustive, and the terms do not exclude other parameters that measure various aspects of photosynthesis.

Reference to properties that are "substantially the same" are intended to mean the properties are within 10%, and preferably within 5%, of the reference value.

Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

Chloroplastic SRP54 (cpSRP54) Mutants and Cytosolic SRP54 (cytoSRP54) Mutants

In the chloroplasts of green plants and algae, the insertion of LHCPs into the thylakoid membranes occurs by interaction of an LHCP that has been imported into the chloroplast stroma with the polypeptides cpSRP43 and cpSRP54 which together make up the chloroplastic signal recognition particle (cpSRP). The cpSRP54 protein is very similar to both the eukaryotic cytosolic SRP54 and the prokaryotic Ffh polypeptide that mediate the interaction of polypeptide with the SRP receptor. The cpSRP43 polypeptide however does not have an ortholog in prokaryotic and eukarotic secretion/membrane protein insertion systems, but rather appears to be an essential part of a specific SRP complex that inserts LHCPs into the thylakoid membranes. Co-translationally inserted thylakoid polypeptides (e.g., reaction center polypeptides) do not require SRP43 in the SRP complex for membrane insertion. In some algal species such as *Chlamydomonas reinhardtii*, the chloroplastic SRP does not include an RNA molecule which is an integral part of the SRP complex in many eukaryotic cytosolic and prokaryotic secretion systems (Schunemann (2004) *Curr Genet* 44:295-304; Trager (2012) *Plant Cell* 24:4819-4836).

The structure of chloroplastic SRP54 corresponds to the domain structure of the cytosolic eukaryotic SRP54, having an SRP GTPase domain, and a SRP54 SB domain, and in some examples an SRP N (helical bundle) domain. These domains can be localized to protein sequences by using the CCD BLAST function at ncbi.gov or by using the search function of any of the Pfam database sites. For example, a cpSRP54 or cytoSRP54 polypeptide can have a domain matching Pfam PF00448 (SRP54 GTPase domain) with a bit score at least as high as the gathering cutoff of 22.7 and can have a domain matching Pfam PF02978 (SRP SPB domain) with a bit score at least as high as the gathering cutoff of 20.1. A cpSRP54 or cytoSRP54 polypeptide can in some examples additionally have a domain matching Pfam PF02881 (SRP54 N domain) with a bit score at least as high as the gathering cutoff of 22.4 and in some examples may have not have a domain with a bit score that meets the gathering cutoff of 22.4 for Pfam PF02881 (SRP54 N domain). The identification of an SRP54 as chloroplastic can be by alignment of the protein sequence with other known cpSRP54 sequences (Trager et al. (2012) *The Plant Cell* 24:4819-4836 (see, Supplemental FIG. 4 and Supplemental Table 1, available at plantcell.org/cgi/doi/10.1105/tpc.112.102996). Although cpSRP54 mutants are known in higher plants (Pilgrim et al. (1998) *Plant J* 13:177-186; Amin et al. (1999) *Plant Physiol* 121:61-70), no SRP54 mutants have been isolated in algae, such as for example, chlorophyte, charophyte, or heterokont (e.g., members of the eustigmatophyceae, bacillariophyceae, coscinodiscophyceae, or fragilariophyceae) microalgae.

Microalgae as provided herein that have a mutated cpSRP54 or cytoSRP54 gene can have a cpSRP54 gene or cytoSRP54 gene with a mutation that inactivates the gene, e.g., results in no functional protein being made, or can be a mutation that results in a reduced amount of a cpSRP54 or cytoSRP54 polypeptide being made with respect to a wild type cell. Attenuated expression of a cpSRP54 gene or of a cytoSRP54 gene can therefore be expression that is absent, undetectable, or reduced by any amount with respect to a wild type gene. For example, mRNA encoding a cpSRP54 or cytoSRP54 polypeptide can be quantitated in mutant cells to demonstrate attenuated expression, or a cpSRP54 or cytoSRP54 polypeptide can be detected with an antibody to demonstrate attenuated expression and/or an aberrant protein. Levels of mRNA or protein can be reduced, for example, from at least about 5% to greater than 99% with respect to a control strain in a mutant algal strain with attenuated expression of a cpSRP54 or cytoSRP54 gene.

In some examples, a gene encoding a cpSRP54 gene has a mutation that changes at least one amino acid or results in a premature stop codon, where the mutation is outside the first 169 amino acids of the GTPase domain. In some examples of cpSRP54 mutants provided herein, the gene encoding a cpSRP54 has a mutation that is outside the GTPase domain.

In addition to mutations that occur within the coding sequence of a cpSRP54 gene or cytoSRP54 gene, the inventors contemplate mutations in the promoter region, 5' UTR, and 3' UTR of a cpSRP54 gene or cytoSRP54 gene. As nonlimiting examples, insertions of a nucleic acid sequence into any of these regions, or deletions in any of these regions, may result in decreased expression of the cpSRP54 gene or cytoSRP54 gene.

In some examples, the microalga having a mutated or attenuated cpSRP54 gene or cytoSRP54 gene may be naturally haploid. In additional examples, the microalga having a mutant cpSRP54 gene or cytoSRP54 gene may be diploid or polyploid and may have one, both, or all copies of the cpSRP54 gene or cytoSRP54 gene mutated or attenuated. For example, a cpSRP54 mutant alga as provided herein can be a diploid alga and can have one or both copies of the cpSRP54 gene attenuated, for example, by an inactivating mutation or insertion. Alternatively or in addition, a cpSRP54 mutant alga as provided herein can be a haploid, diploid, or polyploid alga and can have include a construct for cpSRP54 gene attenuation, such as, for example, an RNAi or antisense construct that targets the cpSRP54 transcript. Similarly, a cytoSRP54 mutant alga as provided herein can be a diploid alga and can have one or both copies of the cytoSRP54 gene attenuated, for example, by an inactivating mutation or insertion. Alternatively or in addition, a cytoSRP54 mutant alga as provided herein can be a haploid, diploid, or polyploid alga and can have include a construct for cytoSRP54 gene attenuation, such as, for example, an RNAi or antisense construct that targets the cytosolic SRP54 transcript.

As disclosed in Example 8, the Parachlorella cpSRP54 gene (cDNA provided as SEQ ID NO:1) encodes a polypeptide having homology to SRP54 genes of other algae that are also predicted to be chloroplastic SRP54 genes. The Parachlorella cpSRP54 polypeptide (SEQ ID NO:2) has a polypeptide having homology to the cpSRP54 of *Chlamydomonas reinhardtii* A8J758; Gene ID: 5722916 Genbank accession EDP00260 GI:158274478 (SEQ ID NO:3); the cpSRP54 of *Micromonas pusilla* C1MLE1; Genbank accession EEH59526 GI:226462234 (SEQ ID NO:4); the cpSRP54 of *Micromonas* sp C1FE02 Genbank accession AC068481.1 GI:226522498 (SEQ ID NO:5); the cpSRP54 of *Paulinella chromatophora* B1X3Q8 Genbank accession ACB42577 GI:171191615 (SEQ ID NO:6); the cpSRP54 of *Ostreococcus lucimarinus* A4RQK2 Genbank accession AB094038 GI:144575969 (SEQ ID NO:7); the cpSRP54 of *Ostreococcus tauri* Genbank accession Q01H03 GI:122162028 (SEQ ID NO:8); the cpSRP54 of *Volvox carteri* D8UEN3 Genbank accession EFJ41797 GI:300257550 (SEQ ID NO:9); the cpSRP54 of *Phaeodactylum tricornutum* B7FXT4 Genbank accession EEC48599 GI:217408666 (SEQ ID NO:10); the cpSRP54 of *Nannochloropsis gaditana* (SEQ ID NO:11); the cpSRP54 of *Thalassiosira pseudonana* B8BUG8 Genbank accession EED94755 GI:220976428 (SEQ ID NO:12); the cpSRP54 of *Aureococcus anophagefferens* 323456635 Genbank accession EGB12501 GI:323456635 (SEQ ID NO:13); and the cpSRP54 of *Ectocarpus siliculosus* D8LN22 Genbank accession CBN76263, GI:299116639 (SEQ ID NO:14). In nonlimiting examples, a mutant microoalga as provided herein can have a mutated or attenuated cpSRP54 gene that (as a nonmutated gene) encodes a polypeptide comprising an amino acid sequence having at least 50% identity to any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, for example, having at least 55%, at least 60%, at least 65%, at least 70%, at least 75%, at least 80% or at least 85%, at least 90%, or at least 95% sequence identity to a cpSRP54 selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14. For example, a mutant microalga as provided herein can be a Chlorophyte alga, and can can have a mutated or attenuated cpSRP54 gene that (as a nonmutated gene) encodes a polypeptide comprising an amino acid sequence having at least 55%, at least 60%, at least 65%, at least 70%, at least 75%, at least 80% or at least 85%, at least 90%, or at least 95% sequence identity to a cpSRP54 selected from the group consisting of SEQ ID NO:2, SEQ ID NO:3, SEQ ID NO:4, SEQ ID NO:5, SEQ ID NO:6, SEQ ID NO:7, and SEQ ID NO:8. Alternatively or in addition, a mutant microalga as provided herein can have a mutated or attenuated cpSRP54 gene that (as a nonmutated gene) encodes a polypeptide having an amino acid sequence with at least 50% identity to any of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:24, SEQ ID NO:25, SEQ ID NO:26, and SEQ ID NO:27, for example, having at least 55%, at least 60%, at least 65%, at least 70%, at least 75%, at least 80% or at least 85%, at least 90%, or at least 95% sequence identity to a cpSRP54 selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

In particular nonlimiting examples, a mutant microalga as provided herein can have a mutated or attenuated cpSRP54 gene that (as a nonmutated gene) encodes a polypeptide comprising an amino acid sequence having at least 50% identity to any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, wherein the cpSRP54 polypeptide further comprises an amino acid sequence having at least 55%, at least 60%, at least 65%, at least 70%, at least 75%, at least 80% or at least 85%, at least 90%, or at least 95% sequence identity to an amino acid sequence encoding a GTPase domain selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

In some embodiments, a mutant microalga as provided herein is a chlorophyte alga and can have a mutated or attenuated cpSRP54 gene that (as a nonmutated gene) encodes a polypeptide comprising an amino acid sequence having at least 50% identity to any of SEQ ID NO:2, SEQ ID NO:3, SEQ ID NO:4, SEQ ID NO:5, SEQ ID NO:7, SEQ ID NO:8, and SEQ ID NO:9, and can additionally or alternatively be encode a cpSRP54 polypeptide that comprises an amino acid sequence having at least 55%, at least 60%, at least 65%, at least 70%, at least 75%, at least 80% or at least 85%, at least 90%, or at least 95% sequence identity to an amino acid sequence encoding a GTPase domain selected from the group consisting of SEQ ID NO:15, SEQ ID NO:16, SEQ ID NO:17, SEQ ID NO:18, SEQ ID NO:20, SEQ ID NO:21, and SEQ ID NO:22.

A mutant alga as provided herein that has a mutated or attenuated cpSRP54 gene exhibits a reduced amount of total chlorophyll with respect to a control alga (e.g., a wild type alga or alga having the same genotype as the mutant alga other that the mutation or attenuation of expression of the cpSRP54 gene). Depending on the species, the mutant alga can have reduced chlorophyll a (e.g., for heterokont algae) or can have reduced chlorophyll a and chlorophyll b (e.g., for chlorophytes and charyophytes). In species that naturally have both reduced chlorophyll a and chlorophyll b (e.g., chlorophytes and charyophytes) the mutant alga can exhibit an increased chlorophyll a:b ratio. For example, the ratio of chlorophyll a to chlorophyll b can be increased by at least 15%, at least 20%, at least 25%, at least 30%, at least 35%, at least 40%, at least 45%, at least 50%, at least 55%, at least 60%, at least 65%, at least 70%, at least 75%, or at least 80%.

The properties of a cpSRP54 mutant having a disrupted, attenuated, or otherwise directly or indirectly genetically manipulated cpSRP54 gene resulting in altered structure or expression of the cpSRP54 gene or of a cytosolic SRP54 mutant having a disrupted, attenuated, or otherwise directly or indirectly genetically manipulated cytosolic SRP54 gene resulting in altered structure or expression of the cytoSRP54 gene are compared with the same properties of a control alga that does not have a disrupted, attenuated, or otherwise directly or indirectly genetically manipulated SRP54 gene resulting in altered structure or expression of the SRP54 gene (regardless of whether the cell is "wild-type"). That is, a control cell is substantially identical to the cpSRP54 mutant or cytoSRP54 mutant except that it does not have a disrupted, attenuated, or otherwise directly or indirectly genetically manipulated cpSRP54 gene or cytoSRP54 gene resulting in altered structure or expression of the cpSRP54 gene or cytoSRP54 gene. For example, a control cell may be a wild type cell or may be a recombinant cell or a cell mutated in a gene other than the cpSRP54 gene or cytoSRP54 gene.

In addition to having reduced chlorophyll with respect to a control alga, a mutant alga as provided herein that has a mutated or attenuated cpSRP54 gene can exhibit at least one of the following photophysiological properties characteristic of LIHLA mutants with respect to a control alga: increased Fv/Fm, increased photochemical quenching (qP) with respect to a control alga, decreased nonphotochemical quenching (NPQ), increased electron transport rate through photosystem II ETR(II), and increased photosynthetic efficiency (Y(II)). In some exemplary embodiments, an algal mutant as provided herein that has a mutated or attenuated cpSRP54 gene demonstrates, with respect to a control alga, increased Fv/Fm, increased photochemical quenching (qP), decreased nonphotochemical quenching (NPQ), increased electron transport rate through photosystem II ETR(II), and increased photosynthetic efficiency (Y(II)).

For example, a cpSRP54 mutant can exhibit increased Fv/Fm with respect to a control microalga at all light intensities greater than about 250 μmol photons $m^{-2}$ $sec^{-1}$ and up to at least 2800 μmol photons $m^{-2}$ $sec^{-1}$, or at light intensities greater than about 75 μmol photons $m^{-2}$ $sec^{-1}$ and up to at least 2800 μmol photons $m^{-2}$ $sec^{-1}$, at all light intensities greater than about 40 μmol photons $m^{-2}$ $sec^{-1}$ and up to at least 2800 μmol photons $m^{-2}$ $sec^{-1}$, or at light intensities greater than 10 μmol photons $m^{-2}$ $sec^{-1}$ and up to at least 2800 μmol photons $m^{-2}$ $sec^{-1}$.

Further, a mutant alga as provided herein that has a mutant or attenuated cpSRP54 gene can exhibit higher qP values with respect to a control microalga at all light intensities greater than 250 μmol photons $m^{-2}$ $sec^{-1}$ and up to at least 2800 μmol photons $m^{-2}$ $sec^{-1}$, or at light intensities greater than 250 μmol photons $m^{-2}$ $sec^{-1}$ and up to at least 2800 μmol photons $m^{-2}$ $sec^{-1}$, at intensities greater than about 75 μmol photons $m^{-2}$ $sec^{-1}$ and up to at least 2800 μmol photons $m^{-2}$ $sec^{-1}$, at all light intensities greater than about 40 μmol photons $m^{-2}$ $sec^{-1}$ and up to at least 2800 μmol photons $m^{-2}$ $sec^{-1}$, or at light intensities greater than 10 μmol photons $m^{-2}$ $sec^{-1}$ and up to at least 2800 μmol photons $m^{-2}$ $sec^{-1}$.

In addition, a mutant alga as provided herein that has a mutant or attenuated cpSRP54 gene can exhibit lower NPQ values with respect to a control microalga at all light intensities greater than 250 μmol photons $m^{-2}$ $sec^{-1}$ and up to at least 2800 μmol photons $m^{-2}$ $sec^{-1}$, at all light intensities greater than 150 μmol photons $m^{-2}$ $sec^{-1}$ and up to at least 2800 μmol photons $m^{-2}$ $sec^{-1}$, or at light intensities greater than about 75 μmol photons $m^{-2}$ $sec^{-1}$ and up to at least 2800 μmol photons $m^{-2}$ $sec^{-1}$, at all light intensities greater than about 40 μmol photons $m^{-2}$ $sec^{-1}$ and up to at least 2800 μmol photons $m^{-2}$ $sec^{-1}$, or at light intensities greater than 10 μmol photons $m^{-2}$ $sec^{-1}$ and up to at least 2800 μmol photons $m^{-2}$ $sec^{-1}$.

Further additionally, a mutant alga as provided herein that has a mutant or attenuated cpSRP54 gene can exhibit higher photosystem II electron transport rates (ETR(II)) with respect to a control microalga at all light intensities greater than 250 μmol photons $m^{-2}$ $sec^{-1}$ and up to at least 2800 μmol photons $m^{-2}$ $sec^{-1}$, or at light intensities greater than 150 μmol photons $m^{-2}$ $sec^{-1}$ and up to at least 2800 μmol photons $m^{-2}$ $sec^{-1}$, at all light intensities greater than 75 μmol photons $m^{-2}$ $sec^{-1}$ and up to at least 2800 μmol photons $m^{-2}$ $sec^{-1}$, or at light intensities greater than 40 μmol photons $m^{-2}$ $sec^{-1}$ and up to at least 2800 μmol photons $m^{-2}$ $sec^{-1}$.

Yet further additionally, a mutant alga as provided herein that has a mutant or attenuated cpSRP54 gene can exhibit higher photosynthetic efficiency (Y(II)) with respect to a control microalga at all light intensities greater than 250 μmol photons $m^{-2}$ $sec^{-1}$ and up to at least 2800 μmol photons $m^{-2}$ $sec^{-1}$, or at all light intensities greater than 150 μmol photons $m^{-2}$ $sec^{-1}$ and up to at least 2800 μmol photons $m^{-2}$ $sec^{-1}$, at light intensities greater than about 75 μmol photons $m^{-2}$ $sec^{-1}$ and up to at least 2800 μmol photons $m^{-2}$ $sec^{-1}$, at all light intensities greater than about 40 μmol photons $m^{-2}$ $sec^{-1}$ and up to at least 2800 μmol photons $m^{-2}$ $sec^{-1}$, or at light intensities greater than 10 μmol photons $m^{-2}$ $sec^{-1}$ and up to at least 2800 μmol photons $m^{-2}$ $sec^{-1}$.

Additionally to any of the above photophysiological properties, a mutant alga as provided herein that has a mutated or attenuated cpSRP54 gene can also exhibit higher rates of oxygen evolution with respect to a control alga. In some examples, a cpSRP54 mutant can exhibit at least a 50%, at least a 80%, at least a 100%, at least a 200%, at least a 200%, or at least a 350% higher rate of oxygen evolution on a per chlorophyll basis than a control alga. Further additionally, a mutant alga as provided herein that has a mutated or attenuated cpSRP54 gene can also exhibit higher rates of carbon fixation with respect to a control alga. In some examples, a cpSRP54 mutant can exhibit a rate or carbon fixation that is at least 50%, at least 60%, at least 70%, at least 80%, or at least 100% higher than the rate of carbon fixation on a per chlorophyll basis of a control alga.

In some exemplary embodiments, an algal mutant as provided herein that has a mutated or attenuated cpSRP54 gene demonstrates increased Fv/Fm with respect to a control alga, increased photochemical quenching (qP) with respect to a control alga, decreased nonphotochemical quenching (NPQ) with respect to a control alga, increased electron transport rate through photosystem II ETR(II) with respect to a control alga, and increased photosynthetic efficiency (Y(II)) with respect to a control alga, and further exhibits higher rates of oxygen evolution and higher rates of carbon fixation with respect to a control alga, for example, at light intensities greater than 250, greater than 150, greater than 75, or greater than 40 μmol photons $m^{-2}$ $sec^{-1}$.

An algal cpSRP54 mutant as provided herein having a mutated or attenuated cpSRP54 gene can also exhibit greater productivity in a culture system, such as a photoautotrophic culture system. By "photoautotrophic culture system" it is meant that the culture medium does not provide a substantial amount of reduced carbon that can be metabolized by the cell. For example, in a photoautotrophic culture system any reduced carbon that is present in the medium that can be metabolized by the cell is present in an amount insufficient to support growth of the culture. In photoautotrophic cultures, any reduced carbon that may be present in small (sub-millimolar) amounts may be introduced in, for example, vitamins or trace metal salts that are inconsequential as a carbon or energy source to the algal culture.

An algal cpSRP54 mutant can demonstrate higher productivity, such as but not limited to higher biomass productivity, in a culture that experiences constant (24 hour per day) light or that experiences light on a diel cycle, where the light period may be, as nonlimiting examples, from 6 to 23 hours per 24 hour cycle and is typically from about 8 to about 16 hours per 24 hour cycle. Light provided during the light period of a diel cycle can be provided at a constant intensity or can be provided at an intensity that varies during the light period, for example, to mimic natural daylight such that the intensity increases from the beginning of the light period to peak in intensity at solar noon, after which the intensity declines to the end of the light period (see for example FIG. 11). In some examples, an algal cpSRP54 mutant as provided herein can have greater productivity, e.g., greater biomass productivity, under one or more of a constant light regime or a diel light regime that provides light of a constant or variable intensity. In some examples, an algal cpSRP54 mutant as provided herein can have greater productivity, e.g., greater biomass productivity, under a constant light regime as well as under a diel light regime that provides light of either a constant or variable intensity. In some examples, an algal cpSRP54 mutant as provided herein can have greater productivity, e.g., greater biomass productivity, under a diel light regime that provides peak light intensity of at least 1900 μmol photons $m^{-2}$ $sec^{-1}$. For example, an algal cpSRP54 mutant as provided herein can accumulate at least 5%, at least 10% at least 15%, or at least 20% more biomass on a daily basis under a diel light regime that provides light of a variable intensity that peaks at between about 1900 μmol photons $m^{-2}$ $sec^{-1}$ and about 2000 μmol photons $m^{-2}$ $sec^{-1}$. In some examples, an algal cpSRP54 mutant as provided herein can have greater productivity, e.g., greater biomass productivity, under a diel light regime that mimics the intensity pattern of natural daylight, where the light profile follows a sinusoidal curve and provides peak light intensity of at least about 1900 μmol photons $m^{-2}$ $sec^{-1}$ and 2000 μmol photons $m^{-2}$ $sec^{-1}$ at the middle of the light period.

Gene Attenuation

An algal cpSRP54 mutant or cytosolic SRP54 mutant can be a mutant generated by any feasible method, including but not limited to UV irradiation, gamma irradiation, or chemical mutagenesis, and screening for low chlorophyll mutants having the photosynthetic properties disclosed herein. Methods for generating mutants of microbial strains are well-known. Mutants can be identified as cpSRP54 mutants or cytoSRP54 mutants by methods known in the art, including, for example, genome sequencing, PCR, immunodetection of the cpSRP54 or cytoSRP54 protein, and expression analysis (e.g., reverse transcription/PCR).

An algal cpSRP54 mutant or cytoSRP54 mutant as provided herein can also be a genetically engineered algal mutant in the cpSRP54 or cytoSRP54 gene, for example, that has been targeted by homologous recombination for knock-out or gene replacement (for example with a mutated form of the gene that may encode a polypeptide having reduced activity with respect to the wild type polypeptide). In additional examples, an algal strain of interest may be engineered by site directed homologous recombination to insert a particular gene of interest with or without an expression control sequence such as a promoter, into a particular genomic locus, or to insert a promoter into a genetic locus of the host microorganism to affect the expression of a particular gene or set of genes at the locus.

For example, gene knockout or replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least 50, at least 100, at least 200, at least 300, at least 400, at least 500, at least 600, at least 700, at least 800, at least 900, at least 1,000, at least 1,200, at least 1,500, at least 1,750, or at least 2,000 nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

In one aspect the invention provides genetically modified organisms, e.g. microorganisms having one or more genetic modifications for attenuating expression of a cpSRP54 or cytoSRP54 gene. As used herein "attenuating expression of a cpSRP54/cytoSRP54 gene" means reducing or eliminating expression of the gene in any manner that reduces production of the fully functional protein.

For example, a recombinant microorganism engineered to have attenuated expression of a cpSRP54 or cytoSRP54 gene can have a disrupted cpSRP54 or cytoSRP54 gene, in which the recombinant microorganism can have a cpSRP54 or cytoSRP54 gene that includes as least one insertion, mutation, or deletion that reduces or abolishes expression of the gene such that a fully functional cpSRP54 gene or cytoSRP54 gene is not produced or is produced in lower amounts than is produced by a control microorganism that does not include a disrupted cpSRP54 gene or cytoSRP54 gene. The disrupted cpSRP54 or cytoSRP54 gene can be disrupted by, for example, an insertion or gene replacement mediated by homologous recombination and/or by the activity of a meganuclease, zinc finger nuclease (Perez-Pinera et al. (2012) *Curr. Opin. Chem. Biol.* 16: 268-277), TALEN (WO 2014/207043; WO 2014/076571), or an RNA-guided endonuclease such as a cas protein (e.g., a Cas9 protein) of a CRISPR system.

CRISPR systems, reviewed recently by Hsu et al. (*Cell* 157:1262-1278, 2014) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA.

The invention contemplates the use of two RNA molecules (a "crRNA" and a "tracrRNA") that can be cotransformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracr-RNA" and a "targeter-RNA" or "crRNA", see below) and referred to herein as a "double-molecule DNA-targeting RNA" or a "two-molecule DNA-targeting RNA." Alternatively, as illustrated in the examples, the DNA-targeting RNA can also include the trans-activating sequence for interaction with the cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety.

Any cas protein can be used in the methods herein, e.g., Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In some embodiments, the cas protein is a class II cas protein. The cas protein can be a Cas9 protein, such as a Cas9 protein of *Staphylococcus pyogenes, S. thermophilus, S. pneumonia, S. aureus*, or *Neisseria meningitidis*, as nonlimiting examples. Other Cas proteins of interest includes, without limitation, the Cpf1 RNA-guided endonuclease (Zetsche et al. (2015) *Cell* 163: 1-13) as well as the C2c1, C2c2, C2c3 RNA-guided nucleases (Shmakov et al. (2015) *Molecular Cell* 60:1-13). Also considered are the Cas9 proteins provided as SEQ ID NOs:1-256 and 795-1346 in U.S. Patent Application Publication No. US 2014/0068797, and chimeric Cas9 proteins that may combine domains from more than one Cas9 protein, as well variants and mutants of identified cas9 proteins. (For example, a Cas9 protein encoded by a nucleic acid molecule introduced into a host cell can comprise at least one mutation with respect to a wild-type Cas9 protein; for example, the Cas9 protein can be inactivated in one of the cleavage domains of the protein resulting in a "nickase" variant. Nonlimiting examples of mutations include D10A, H840A, N854A, and N863A.) The nucleic acid sequence encoding the Cas protein can be codon optimized for the host cell of interest.

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, or TALEN) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g. "knock out" by insertional mutagenesis, or "knock in" a nucleic acid that encodes a protein (e.g., a selectable marker and/or any protein of interest), an siRNA, an miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the cpSRP54 gene. The donor DNA can include a sequence, such as for example a selectable marker or any convenient sequence, that may be interfere with the native promoter. The additional sequence inserted upstream of the initiating ATG of the cpSRP54 open reading frame (e.g., in the 5'UTR or upstream of the transcriptional start site of the cpSRP54 gene) can decrease or even eliminate expression of the endogenous cpSRP54 gene. Alternatively or in addition, the native cpSRP54 gene can have its endogenous promoter wholly or partially replaced by an weaker or differently regulated promoter, or a non-promoter sequence.

In some examples, a nucleic acid molecule introduced into a host cell for generating a high efficiency genome editing cell line encodes a cas9 enzyme that is mutated to with respect to the corresponding wild-type enzyme such that the mutated cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequenc(es), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation.

In additional examples, a mutant Cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) Cell 152:1173-1183).

In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g. transduced or transformed or transfected) with, for example, a vector construct that can be, for example, a vector for homologous recombination that includes nucleic acid sequences homologous to a portion of a cpSRP54 gene locus of the host cell or to regions adjacent thereto or a cytoSRP54 gene locus of the host cell or to regions adjacent thereto, or can be an expression vector for the expression of any or a combination of: a cas protein (e.g., a Class II cas protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host cpSRP54 or cytoSRP54 gene sequences (including sequences that are upstream and downstream of the cpSRP54 or cytoSRP54-encoding sequences), as well as, optionally, a selectable marker or reporter gene, can be employed to transform an appropriate host to cause attenuation of a cpSRP54 gene or cytoSRP54 gene.

The recombinant microorganism in some examples can have reduced but not abolished expression of the cpSRP54 or cytoSRP54 gene, and the recombinant microorganism can have a reduction in chlorophyll of from about 10% to about 90%, for example, a reduction in total chlorophyll from about 20% to about 80%. A genetically modified microorganism as provided herein can in some examples include a nucleic acid construct for attenuating the expression of a cpSRP54 or cytoSRP54 gene. For example, a host microorganism can include a construct for expressing an RNAi molecule, ribozyme, or antisense molecule that reduces expression of a cpSRP54 or cytoSRP54 gene. In some examples, a recombinant microorganism as provided herein can include at least one introduced (exogenous or non-native) construct for reducing expression of a cpSRP54 or cytoSRP54 gene.

Engineered strains can be selected for expression of a cpSRP54 or cytoSRP54 gene that is decreased with respect to a control cell that does not include a genetic modification for attenuating cpSRP54 or cytoSRP54 gene expression, but not eliminated, using methods known in the art, such as, for example, RNA-Seq or reverse transcription-PCR (RT-PCR).

A genetically engineered strain as provided herein can be engineered to include a construct for attenuating gene expression by reducing the amount, stability, or translatability of mRNA of a gene encoding a cpSRP54 or cytoSRP54. For example, a microorganism such as an algal or heterokont strain can be transformed with an antisense RNA, RNAi, or ribozyme construct targeting an mRNA of a cpSRP54 or cytoSRP54 gene using methods known in the art. For example, an antisense RNA construct that includes all or a portion of the transcribed region of a gene can be introduced into a microorganism to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a cpSRP54 or cytoSRP54 gene can be introduced into a microorganism such as an alga or heterokont for reducing expression of the cpSRP54 or cytoSRP54 gene (see, for example, Cerruti et al. (2011) *Eukaryotic Cell* (2011) 10: 1164-1172; Shroda et al. (2006) *Curr. Genet.* 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591.

Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C, or U) (Thompson et al., (1995) *Nucl Acids Res* 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra). Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art.

The use of RNAi constructs is described in literature cited above as well as in US2005/0166289 and WO 2013/016267, for example. A double stranded RNA with homology to the target gene is delivered to the cell or produced in the cell by expression of an RNAi construct, for example, an RNAi short hairpin (sh) construct. The construct can include a sequence that is identical to the target gene, or at least 70%, 80%, 90%, 95%, or between 95% and 100% identical to a sequence of the target gene. The construct can have at least 20, at least 30, at least 40, at least 50, at least 100, at least 200, at least 300, at least 400, at least 500, at least 600, at least 700, at least 800, at least 900, or at least 1 kb of sequence homologous to the target gene. Expression vectors can be engineered using promoters selected for continuous or inducible expression of an RNAi construct, such as a construct that produces an shRNA.

A nucleic acid construct for gene attenuation, e.g., a ribozyme, RNAi, or antisense construct can include at least fifteen, at least twenty, at least thirty, at least forty, at least fifty, or at least sixty nucleotides having at least 80% identity, such as at least 85%, at least 90%, at least 95%, or at least 99% or complementarity to at least a portion of the sequence of an endogenous cpSRP54 gene of the microorganism to be engineered. A nucleic acid construct for gene attenuation, e.g., a ribozyme, RNAi, or antisense construct can include at least fifteen, at least twenty, at least thirty, at least forty, at least fifty, or at least sixty nucleotides having at least 80%, such as at least 95% or about 100%, identity or complementarity to the sequence of a naturally-occurring gene, such as a gene having encoding a polypeptide having at least 50%, at least 55%, at least 60%, at least 65%, at least 70%, at least 75%, at least 80% or at least 85%, at least 90%, or at least 95% sequence identity to an endogenous cpSRP54 gene. For example, a nucleic acid construct for gene attenuation, e.g., a ribozyme, RNAi, or antisense construct can include at least fifteen, at least twenty, at least thirty, at least forty, at least fifty, or at least sixty nucleotides having at least 80% identity or complementarity to the sequence of a naturally-occurring cpSRP54 gene, such as any provided herein. The nucleotide sequence can be, for example, from about 30 nucleotides to about 3 kilobases or greater, for example, from 30-50 nucleotides in length, from 50 to 100 nucleotides in length, from 100 to 500 nucleotides in length, from 500 nucleotides to 1 kb in length, from 1 kb to 2 kb in length, or from 2 to 5 kb. For example, an antisense sequence can be from about 100 nucleotides to about 1 kb in length. For example, a nucleic acid construct for gene attenuation, e.g., a ribozyme, RNAi, or antisense construct can include at least fifteen, at least twenty, at least thirty, at least forty, at least fifty, at least sixty, or at least 100 nucleotides having at least 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least 95% identity or complementarity to an endogenous cpSRP54 or cytoSRP54 gene or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or microorganism transformed with a nucleic acid molecule for attenuating cpSRP54 or cytoSRP54 gene expression, such as but not limited to an antisense, RNAi, or ribozyme construct, can have the properties of a cpSRP54 or cytoSRP54 mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

Nucleic Acid Molecules and Constructs

Also provided herein are nucleic acid molecules and nucleic acid constructs. For example, provided herein are nucleic acid molecules that encode a polypeptide comprising an amino acid sequence having at least 80%, at least 85%, at least 90%, at least 95%, at least 96%, at least 97%, at least 98%, at least 99%, to SEQ ID NO:2. In some examples, the nucleic acid molecule comprises a cDNA sequence. In some examples, the nucleic acid molecule comprises a heterologous promoter operably linked to the nucleic acid sequence encoding a polypeptide having a sequence polypeptide comprising an amino acid sequence having at least 80%, at least 85%, at least 90%, at least 95%, at least 96%, at least 97%, at least 98%, at least 99%, to SEQ ID NO:2. In some examples, the nucleic acid molecule comprises a vector.

Additionally considered are nucleic acid molecules that encode a polypeptide comprising an amino acid sequence having at least 80%, at least 85%, at least 90%, at least 95%, at least 96%, at least 97%, at least 98%, at least 99%, to SEQ ID NO:30. In some examples, the nucleic acid molecule comprises a cDNA sequence. In some examples, the nucleic acid molecule comprises a heterologous promoter operably linked to the nucleic acid sequence encoding a polypeptide having a sequence polypeptide comprising an amino acid sequence having at least 80%, at least 85%, at least 90%, at least 95%, at least 96%, at least 97%, at least 98%, at least 99%, to SEQ ID NO:30. In some examples, the nucleic acid molecule comprises a vector.

Further provided are nucleic acid constructs for attenuating expression of a cpSRP54 gene. In various examples, provided herein is a nucleic acid molecule having at least 85%, at least 95% to at least a portion of a gene encoding any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14, wherein the nucleic acid molecule encodes a guide RNA of a CRISPR system. The nucleic acid molecule can include, for example at least 17, at least 18, at least 19, at least 20, at least 21, at least 22, at least 23, at least 24, or at least 25 nucleotides of sequence of a naturally occurring cpSRP54 gene, such as SEQ ID NO:1.

Also provided are nucleic acid constructs for attenuating expression of a cytoSRP54 gene. For example, a nucleic acid molecule can include, for example at least 17, at least 18, at least 19, at least 20, at least 21, at least 22, at least 23, at least 24, or at least 25 nucleotides of sequence of a naturally occurring cytoSRP54 gene, such as SEQ ID NO:29.

In addition, provided herein are antisense, ribozyme, or RNAi constructs that include at least a portion of a gene encoding a cpSRP54 or cytoSRP54 of a microalgal species, in which a promoter, such as a heterologous promoter, is operably linked to the cpSRP54 or cytoSRP54 gene sequence and the cpSRP54 or cytoSRP54 gene sequence is in antisense orientation.

Further, provided herein are constructs for homologous recombination that include at least one sequence from a cpSRP54 or cytoSRP54 gene locus of the genome of an alga juxtaposed with a heterologous nucleic acid sequence that can be, in nonlimiting examples, a selectable marker or detectable marker gene. In some examples a construct for homologous recombination includes two nucleic acid sequences from a cpSRP54 or cytoSRP54 gene locus of the genome of an alga where the two sequences flank a heterologous sequence for insertion into the cpSRP54 or cytoSRP54 gene locus.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell,* 2010; and Gong et al., *J. Ind. Microbiol. Biotechnol.,* 2011). Nonlimiting examples of such useful transformation methods include agitation of cells in the presence of glass beads or silicon carbide whiskers as reported by, for example, Dunahay, *Biotechniques,* 15(3):452-460, 1993; Kindle, *Proc. Natl. Acad. Sci. U.S.A.,* 1990; Michael and Miller, *Plant J.,* 13, 427-435, 1998. Electroporation techniques have been successfully used for genetic transformation of several microalgal species including *Nannochloropsis* sp. (see, e.g., Chen et al., *J. Phycol.,* 44:768-76, 2008), *Chlorella* sp. (see, e.g., Chen et al., *Curr. Genet.,* 39:365-370, 2001; Chow and Tung, *Plant Cell Rep*. Vol. 18, No. 9, 778-780, 1999), *Chlamydomonas* (Shimogawara et al., *Genetics,* 148: 1821-1828, 1998), *Dunaliella* (Sun et al., *Mol. Biotechnol.,* 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.,* 252:572-579, 1996), *Cyclotella* and *Navicula* (Dunahay et al., *J. Phycol.,* 31:1004-1012, 1995), *Cylindrotheca* (Fischer et al., *J. Phycol.,* 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist,* 155:381-93, 2004). Additionally, *Agrobacterium*-mediated gene transfer techniques can also be useful for genetic transformation of microalgae, as has been reported by, for example, Kumar, *Plant Sci.,* 166(3):731-738, 2004, and Cheney et al., *J. Phycol*., Vol. 37, Suppl. 11, 2001.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslayskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist*, supra.; Sizova et al., *Gene,* 277: 221-229, 2001), nourseothricin (Zaslayskaia et al., 2000, supra), G418 (Dunahay et al., 1995, supra; Poulsen and Kroger, *FEBS Lett.,* 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), β-galactosidase (Gan et al., *J. Appl. Phycol.,* 15:345-349, 2003; Jiang et al., *Plant Cell Rep.,* 21:1211-1216, 2003; Qin et al., *High Technol. Lett.,* 13:87-89, 2003), and green fluorescent protein (GFP) (Cheney et al., 2001, supra; Ender et al., *Plant Cell,* 2002, Franklin et al., *Plant J.,* 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate. Additional algal promoters that can find use in the constructs and transformation systems provided herein include those disclosed in U.S. Pat. No. 8,883,993; U.S. Patent Appl. Pub. No. US 2013/0023035; U.S. Patent Application Pub. No. US 2013/0323780; and U.S. Patent Application Pub. No. US 2014/0363892.

Host cells can be either untransformed cells or cells that are already transfected with at least one nucleic acid molecule. For example, an algal host cell that is engineered to have attenuated expression of a cpSRP54 gene can further include one or more genes that may confer any desirable trait, such as, but not limited to, increased production of biomolecules of interest, such as one or more proteins, pigments, alcohols, or lipids.

Mutant Strains

An algal strain having a mutated cpSRP54 gene or cytoSRP54 gene which can be, in various examples, a strain genetically engineered to have attenuated expression of a cpSRP54 or cytoSRP54 gene, can be any eukaryotic microalgal strain such as, for example, a species of any of the genera *Achnanthes, Amphiprora, Amphora, Ankistrodes-*

*mus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox.*

For example, an alga having a mutation in a cpSRP54 gene or cytoSRP54 gene as disclosed herein can be a species belonging to any of the phyla ochrophyta (including members of the bacillariophyceae, coscinodiscophyceae, fragilariophyceae, eustigmatophyceae, xanthophyceae, pelagophyceae, chrysophyceae, raphidophyceae, and synurophyceae), haptophyta (including members of the coccolithophyceae and pavlophyceae), and chlorophyta (including members of the trebouxiophyceae, chlorophyceae, nephrophyceae, pyramimonadophyceae, ulvophyceae, mamiellophyceae, and chlorodendrophyceae), as well as the charyophyta, euglenoids, and dinoflagellates.

In some embodiments of the present application, preferred microorganisms to genetically engineer include, but are not limited to, chlorophyte species such as *Chlorella, Parachlorella, Pseudochlorella, Tetrachlorella, Auxenochlorella, Prototheca, Oocystis, Franceia, Micratinium, Picochlorum, Nannochloris, Schizochlamydella, Eremosphaera, Stichococcus, Botryococcus, Viridiella, Parietochloris Borodinella, Bracteacoccus, Neochloris, Monoraphidium, Desmodesmus, Scenedesmus, Ankistrodesmus, Carteria, Chlamydomonas, Chlorococcum, Chlorogonium, Volvox, Platymonas, Dunaliella, Haematococcus, Asteromonas, Pyrobotrys, Oedogonium, Nephroselmis, Pleurococcus, Pyramimonas, Pseudoneochloris, Ostreococcus, Tetraselmis*, and *Staurastrum.*

In other examples, mutants can be engineered or isolated using a heterokont algal species such as a diatom species such as, for example, a species of any of the genera *Amphora, Chaetoceros, Cyclotella, Fragilaria, Fragilaropsis, Hantzschia, Navicula, Nitzschia, Phceodactylum*, or *Thalassiosira*. In further examples a mutant as disclosed herein is a species of the Eustigmatophyceae class, such as, for example, a species of *Ellipsoidion, Eustigmatos, Vischeria, Monodus, Nannochloropsis*, or *Pseudostaurastrum*. Other genera of the Ochrophyta that may be considered include, without limitation, *Boldimonas, Botrydium, Baucheria, Tribonema, Monodus, Aureococcus, Bigeloweilla, Pelagomomas, Chrysosphaera, Ochromonas, Heterosigma, Nephrochloris, Boekelovia, Cricosphaera, Hymenomonas, Isochrysis, Pleurochrysis*, and *Pavlova.*

Methods of Producing Algal Products

Also provided herein are methods of producing algal products by culturing algae having increased photosynthetic efficiency, such as the cpSRP54 mutants or cytoSRP54 mutants disclosed herein. The methods include culturing an algal cpSRP54 mutant or cytoSRP54 mutant in a suitable medium to provide an algal culture and recovering biomass or at least one product from the culture. In some embodiments the product is a lipid. The algal culture is preferably a photoautotrophic culture, and the culture medium preferably does not include a substantial amount of reduced carbon, that is, the culture does not include reduced carbon in a form or at a level that can be used by the algae for growth.

The algae may be cultured in any suitable vessel, including flasks or bioreactors, where the algae may be exposed to artificial or natural light. The culture comprising mutant algae may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. As demonstrated in the examples herein, the mutants provided herein exhibiting deregulated adaptation to low light intensity can achieve higher cell density of the culture over time, for example, over a period of a week or more, with respect to a culture wild type algal cells of the same strain that are not deregulated in low light acclimation. For example, a cpSRP54 mutant may be cultured for at least five, at least six, at least seven at least eight, at least nine, at least ten, at least eleven at least twelve, at least thirteen, at least fourteen, or at least fifteen days, or at least one, two three, four, five, six, seven, eight, nine, or ten weeks, or longer.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of biomass or a product such as a lipid, protein, pigment, antioxidant, etc. Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (www.sbs.utexas.edu/utex/media.aspx); Culture Collection of Algae and Protozoa (www.ccap.ac.uk); and Katedra Botaniky (botany.natur.cuni.cz/algo/caup-media.html).

The culture methods can optionally include inducing expression of one or more genes for the production of a product, such a but not limited to a protein that participates in the production of a lipid, one or more proteins, antioxidants, or pigments, and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms deregulated in acclimation to low light intensity can be cultured in a "photobioreactor" equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The algal cpSRP54 mutants can include one or more non-native genes encoding a polypeptide for the production of a product, such as, but limited to, a lipid, a colorant or pigment, an antioxidant, a vitamin, a nucleotide, a nucleic acid, an amino acid, a hormone, a cytokine, a peptide, a protein, or a polymer. For example, the encoded polypeptide can be an enzyme, metabolic regulator, cofactor, carrier protein, or transporter. The methods include culturing a cpSRP54 mutant or cytoSRP54 mutant that includes at least one non-native gene encoding a polypeptide that participates in the production of a product, to produce biomass or at least one algal product. Products such as lipids and proteins can be recovered from culture by recovery means known to those of ordinary skill in the art, such as by whole culture extraction, for example, using organic solvents. In some cases, recovery of fatty acid products can be enhanced by homogenization of the cells. For example, lipids such as fatty acids, fatty acid derivatives, and/or triglycerides can be isolated from algae by extraction of the algae with a solvent at elevated temperature and/or pressure, as described in the co-pending, commonly-assigned U.S. Patent Application Publication No. US 2013/0225846, which is incorporated herein by reference in its entirety.

Biomass can be harvested, for example, by centrifugation or filtering. The biomass may be dried and/or frozen. Further products may be isolated from biomass, such as, for example, lipids or one or more proteins. Also included in the invention is an algal biomass comprising biomass of an algal cpSRP54 mutant or algal cytoSRP54 mutant, such as any disclosed herein, for example, an algal cpSRP54 or cytoSRP54 mutant that includes a mutation in a gene encoding a cpSRP54 having at least 50% identity to SEQ ID NO:2 or cytoSRP54 gene having at least 50% identity to SEQ ID NO:29.

Alternatively or in addition to any of the embodiments described above, the invention provides the following embodiments:

Embodiment 1 is a mutant alga having an altered or attenuated gene encoding a cpSRP54 polypeptide, where the mutant can be an isolated variant generated by classical mutagenesis or may be a genetically engineered alga having a disrupted or mutated gene encoding a cpSRP54 polypeptide and/or that includes a construct that attenuates expression of the endogenous cpSRP54 polypeptide, wherein the mutant alga has reduced total chlorophyll with respect to a control alga that does not have an altered or attenuated gene encoding a cpSRP54 polypeptide.

Embodiment 2 is a mutant alga according to embodiment 1, wherein the mutant alga has at least a 20%, at least a 30%, at least a 40%, at least a 50%, at least a 55%, at least a 60%, at least a 65%, or at least a 70% reduction in total chlorophyll with respect to a control cell, optionally further wherein the mutant has a chlorophyll a to chlorophyll b ratio that is increased by at least with respect to a control cell, further optionally wherein the ratio of chlorophyll a to chlorophyll b is at least about 2.8:1, at least about 3:1, at least about 3.2:1, about 3.3:1, at least about 3.5:1, at least about 3.7:1, at least about 3.9:1, at least about 4:1, or at least about 4.3:1.

Embodiment 3 is a mutant alga according to embodiment 1, where the mutant alga demonstrates one or more of the following:

(a) higher qP with respect to a control alga at all irradiances between about 250 and about 2800 μmol photons $m^{-2}$ $sec^{-1}$, between about 150 and about 2800 μmol photons $m^{-2}$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(b) lower NPQ with respect to a control alga at all irradiances between about 250 and about 2800 μmol photons $m^{-2}$ $sec^{-1}$, between about 150 and about 2800 μmol photons $m^{-2}$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(c) higher Y(II) with respect to a control alga at all irradiances between about 250 and about 2800 μmol photons $m^{-2}$ $sec^{-1}$, between about 150 and about 2800 μmol photons $m^{-2}$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(d) higher Fv/Fm with respect to a control alga between about 250 and about 2800 μmol photons $m^{-2}$ $sec^{-1}$, between about 150 and about 2800 μmol photons $m^{-2}$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(e) higher ESR(II) with respect to a control alga between about 250 and about 2800 μmol photons $m^{-2}$ $sec^{-1}$, between about 150 and about 2800 μmol photons $m^{-2}$ $sec^{-1}$, between about 75 and about 2800 μmol photons $m^{-2}$ $sec^{-1}$, between about 40 and about 2800 μmol photons $m^{-2}$ $sec^{-1}$, or between about 10 and about 2800 μmol photons $m^{-2}$ $sec^{-1}$;

(f) oxygen evolution on a per chlorophyll basis increased by at least 50%, at least 100% at least 200%, at least 300%, at least 350%, or at least 400% with respect to a control alga; and (g) carbon fixation on a per chlorophyll basis increased by at least 50%, at least 60% at least 70%, at least 80%, at least 90%, or at least 100% with respect to a control alga.

Embodiment 4 is a mutant alga according to any of embodiments 1-3, where the mutant alga demonstrates greater productivity with respect to the control alga in one or more of a constant light culture, or a diel cycle culture having a constant light intensity, or a diel cycle culture having a variable light intensity.

Embodiment 5 a mutant alga according to any of embodiments 1-3, where the mutant alga demonstrates greater productivity with respect to the control alga in a diel cycle culture having a variable light intensity mimicking natural daylight, optionally wherein the light intensity peaks at between about 1900 and about 2000 μmol photons $m^{-2}$ $sec^{-1}$.

Embodiment 6 is a mutant alga according to embodiments 4 or embodiment 5, where the mutant alga demonstrates at least 5%, at least 6%, at least 8%, or at least 10%, at least 15%, at least 25%, or at least 30% greater biomass productivity than a control alga cultured under identical conditions.

Embodiment 7 is a mutant alga according to any of embodiments 1-6, wherein the mutated cpSRP54 gene has a GTPase domain having at least 60% identity to any of SEQ ID NOs:15-27.

Embodiment 8 is a mutant alga according to any of embodiments 1-7, wherein the mutated cpSRP54 gene has at least 50% identity to any of SEQ ID NOs:2-14.

Embodiment 9 is a mutant alga according to any previous embodiment, wherein the alga is a eukaryotic microalga, optionally belonging to any of the phylogenetic groups chlorophyta, charophyta, ochrophyta, haptophyta, cryptophyta, or dinoflagellate, and/or belonging to any of the classes bacillariophyceae, fragilariophyceae, coscinodiscophyceae, eustigmatophyceae, bolidophyceae, xanthophyceae, pelagophyceae, chrysophyceae, chlorarachniophyceae, raphidophyceae, synurophyceae, coccolithophyceae, pavlovophyceae, trebouxiophyceae, chlorophyceae, pyramimonadophyceae, nephrophyceae, ulvophyceae, mamiellophyceae, chlorodendrophyceae, euglenophyceae, and/or belonging to of any of the genera *Amphora, Ankistrodesmus, Aplanochytrium, Asteromonas, Aureococcus, Boekelovia, Bolidomonas, Borodinella, Botrydium, Botryococcus, Bracteacoccus, Carteria, Chaetoceros, Chlamydomonas, Chlorella, Chlorococcum, Chlorogonium, Chroomonas, Chrysophyceae, Chrysosphaera, Cricosphaera, Crypthecodinium, Cryptomonas, Cyclotella, Cyanidioschyzon, Desmodesmus, Dunaliella, Elina, Ellipsoidon, Emiliania, Eremosphaera, Ernodesmius, Euglena, Eustigmatos, Fragilaria, Fragilariopsis, Franceia, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Picochlorum, Platymonas, Pleurochrysis, Pleurococcus, Porphyridium, Prototheca, Pseudochlorella, Pseudoneochloris, Pseudostaurastrum, Pyramimonas, Pyrobotrys, Rholdella, Scenedesmus, Schizochlamydella, Skeletonema, Spyrogyra, Staurastrum, Stichococcus, Tetrachlorella, Tetraselmis, Thalassiosira, Tribonema, Vaucheria, Viridiella, Vischeria*, and *Volvox*.

Embodiment 10 is biomass comprising an alga according to any of embodiments 1-9.

Embodiment 11 is a method of producing an algal product comprising cultivating an algal mutant according to any of embodiments 1-9 and isolating at least one algal product from the algal cells, the algal culture medium, or both, preferably wherein the cultivating is under photoautrophic conditions, optionally wherein the algal product is optionally selected from the group consisting of biomass, lipid, protein, nucleic acid, a nucleotide, a vitamin, an antioxidant, a pigment, a colorant, a terpenoid, or a carotenoid.

Embodiment 12 is a nucleic acid molecule comprising a nucleic acid sequence encoding the polypeptide of SEQ ID NO:2, optionally wherein: the nucleic acid sequence comprises a cDNA, the nucleic acid sequence is operably linked to a heterologous promoter, the nucleic acid molecule comprises a vector, the nucleic acid sequence includes at least one mutation with respect to a wild-type gene.

Embodiment 12 is a nucleic acid construct comprising a portion of a gene encoding a cpSRP54, wherein the construct is a construct for homologous recombination.

Embodiment 13, is a nucleic acid construct encoding a guide RNA, an antisense RNA, an RNAi, or a ribozyme construct, wherein the nucleic acid construct comprises a sequence having homology to at least a portion of a cpSRP54 gene.

Embodiment 14: is a nucleic acid molecule according to embodiment 12 or 13, wherein the cpSRP54 comprises a nucleic acid sequence having at least 60% identity to a GTPase domain selected from SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27.

Embodiment 15 is a nucleic acid molecule according to any of embodiments 12-14, wherein the cpSRP54 has at least 50% identity to an amino acid sequence selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

Embodiment 16 is a mutant alga having an altered or attenuated gene encoding a cytosolic SRP54 polypeptide, where the mutant can be an isolated variant generated by classical mutagenesis or may be a genetically engineered alga having a disrupted or mutated gene encoding a cytoSRP54 polypeptide and/or that includes a construct that attenuates expression of the endogenous cytoSRP54 polypeptide, wherein the mutant alga has higher lipid productivity, for example, at least 5%, at least 10%, at least 15%, at least 20%, or at least 25% higher lipid productivity with respect to a control alga that does not have an altered or attenuated gene encoding a cytoSRP54 polypeptide.

Embodiment 17 is a mutant alga according to embodiment 16 wherein the mutant alga is a heterokont alga, for example a Bacillariophyte or Eustigmatophyte alga, optionally a Bacillariophyte, further optionally of a genus selected from the group consisting of *Amphora, Chaetoceros, Cyclotella, Fragilaria, Fragilaropsis, Hantzschia, Monodus, Navicula, Nitzschia, Phaeodactylum*, and *Thalassiosira* or a Eustigmatophyte further optionally of a genus selected from the group consisting of *Ellipsoidion, Eustigmatos, Vischeria, Nannochloropsis, Monodus*, or *Pseudostaurastrum.*

Embodiment 18 is a method of producing lipid comprising culturing a mutant alga according to embodiment 17 or embodiment 18 under conditions in which the mutant alga makes lipid, optionally wherein the culture conditions are nitrogen replete or nutrient replete, further optionally wherein the culture conditions are photoautotrophic.

Other alternative embodiments and methods will be apparent to those of skill in the art upon review of this disclosure. The discussion of the general methods given herein is intended for illustrative purposes only. The following examples are offered to illustrate, but not limit, the invention.

EXAMPLES

Example 1. Cas9 Mediated Knockout of the cpSRP54 Gene in *Nannochloropsis*

The *Nannochloropsis* genome encodes two putative SRP54 homologs: the chloroplastic gene *N. gaditana* cpSRP54 (T6676) (coding sequence provided as SEQ ID NO:28, encoding the polypeptide sequence of SEQ ID NO:11) and the cytosolic gene *N. gaditana* cytoSRP54 (T5548) (coding sequence provided as SEQ ID NO:29, encoding the polypeptide sequence SEQ ID NO:30). The chloroplastic SRP54 gene was knocked out using a high efficiency genome editing *Nannochloropsis* cell line that expressed a Cas9 gene as disclosed in co-pending U.S. patent application Ser. No. 14/986,492 entitled "Compositions and Methods for High Efficiency Genome Editing" filed Dec. 31, 2015, incorporated by reference herein in its entirety. As described in U.S. Ser. No. 14/986,492, a highly efficient *Nannochloropsis* Cas9 Editor line, *N. gaditana* strain GE-6791, expressing a gene encoding the *Streptococcus pyogenes* Cas9 nuclease, was used as a host for transformation with a chimeric guide RNA and donor DNA for insertional knockout.

To produce the high efficiency *Nannochloropsis* Cas9 Editor line, a *Nannochloropsis* strain was engineered and isolated that exhibited expression of the introduced Cas9 gene in close to 100% of the cell population of a growing culture. The vector pSGE-6206 (FIG. 1; SEQ ID NO:31), used to transform wild type *N. gaditana* strain WT-3730 included the following three elements: 1) a Cas9 expression cassette which contained a Cas9 gene from *Streptococcus pyogenes* codon optimized for *Nannochloropsis gaditana* (SEQ ID NO:32) that also included sequences encoding an N-terminal FLAG tag (SEQ ID NO:33), nuclear localization signal (SEQ ID NO:34), and peptide linker (SEQ ID NO:35), driven by the *N. gaditana* RPL24 promoter (SEQ ID NO:36) and terminated by *N. gaditana* bidirectional terminator 2 (or "FRD" terminator) (SEQ ID NO:37); 2) a selectable marker expression cassette, which contained the blasticidin deaminase ("blast" or "BSD") gene from *Aspergillus terreus* codon optimized for *N. gaditana* (SEQ ID NO:38), driven by the *N. gaditana* TCTP promoter (SEQ ID NO:39) and followed by the EIF3 terminator (SEQ ID NO:40); and 3) a GFP reporter expression cassette, which contained the TurboGFP gene (Evrogen, Moscow, Russia) codon optimized for *Nannochloropsis gaditana* (SEQ ID NO:41), driven by the *N. gaditana* 4A-III promoter (SEQ ID NO:42) and followed by the *N. gaditana* bidirectional terminator 5 (or "GNPDA" terminator) (SEQ ID NO:43). The Cas9 expression construct was assembled according to the Gibson Assembly® HiFi 1 Step Kit (Synthetic Genomics, La Jolla, Calif.) into a minimal pUC vector backbone.

The ZraI-linearized Cas9 expression construct was transformed into *Nannochloropsis* cells by electroporation. 1×109 cells were transformed in a 0.2 cm cuvette using a field strength of 7,000 V/cm delivered with the Gene Pulser II (Biorad, Carlsbad, Calif., USA). The transformation mixture was plated onto PM074 agar medium containing 100 mg/L of blasticidin. Resulting colonies were patched onto selection media for analysis and archiving. A small amount of biomass was taken from the patches and completely resuspended in 300 μl of 1× Instant Ocean Salts solution (Aquatic Eco Systems; Apopka, Fla.). Care was taken to not add too much biomass so that a light green resuspension was obtained. This suspension was directly analyzed by flow cytometry using a BD Accuri C6 flow cytometer, using a 488 nm laser and 530/10 nm filter to measure GFP fluorescence per cell. 10,000-30,000 events were recorded for each sample using the slow fluidics setting. A strain having a single fluorescence peak that was shifted to a fluorescence level higher than that demonstrated by wild-type cells (FIG. 2A, distinguished from FIG. 2B showing clone p2-02 giving rise to two peaks, one of which coincides with the wild type peak) and also demonstrating Cas9 protein expression by Western blotting using an anti-FLAG antibody (Sigma #A9469) (FIG. 2C), designated strain GE-6791, was selected as a Cas9 Editor strain and used in mutant generation by cas9/CRISPR genome editing as described herein.

The *Nannochloropsis gaditana* cpSRP54 gene (cpSRP-6676) was targeted for disruption by first making a DNA construct for producing a guide RNA in which the construct included the sequence of a chimeric guide engineered downstream of a T7 promoter. The chimeric guide sequence included a target sequence (20 bp including PAM) (SEQ ID NO:44) homologous to a sequence within the cpSRP-6676 gene sequence that was upstream of an *S. pyogenes* Cas9 PAM sequence (NGG), and also included the transactivating CRISPR (tracr) sequence. The chimeric guide sequence was synthesized as described in Cho et al., 2013 (Nature biotechnology 31, 230-232) by first making a DNA template made up of complementary DNA oligonucleotides that were annealed to create a double-stranded DNA template which was used in in vitro transcription reactions using the MEGAshortscript™ T7 Kit (Life Technologies #AM1354M) according to the manufacturer's instructions to synthesize the guide RNA. The resulting RNA was purified using Zymo-Spin™ V-E columns (Zymo Research #C1024-25) according to manufacturer's protocol.

The donor fragment for insertion into the targeted cpSRP-6676 locus (SEQ ID NO:45) included a selectable marker cassette that included the hygromycin resistance gene (HygR, SEQ ID NO:46) downstream of the *N. gaditana* EIF3 promoter (SEQ ID NO:47) and followed by *N. gaditana* bidirectional terminator 2 (SEQ ID NO:37), with the entire promoter-hygromycin resistance gene-terminator sequence flanked by 27 base pair identification sequences on the 5' (SEQ ID NO:48 5'ID) and 3' (SEQ ID NO:49 3'ID) ends to yield the DNA fragment referred to as the "Hyg Resistance Cassette" (SEQ ID NO:45 HygR Cassette).

For targeted knockout of the cpSRP54-6676 locus, Cas9 Editor line GE-6791 was transformed by electroporation using 5 μg of purified chimeric guide RNA targeting the cpSRP54-6676 gene (target sequence SEQ ID NO:44) and 1 μg of the selectable donor DNA (Hyg Resistance Cassette; SEQ ID NO:45) essentially as described in US 2014/0220638. Following electroporation, cells were plated on PM124 agar media containing hygromycin to select for transformants that incorporated the hygromycin resistance cassette. Transformants were patched onto a fresh plate and screened by colony PCR for insertion of the donor fragment into the cpSRP54-6676 gene.

PM074 is a nitrogen replete ("nitrate-only") medium that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM $NaNO_3$, 0.361 mM $NaH_2PO_4.H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60). PM124 medium is PM074 supplemented with 5 mM ammonium and 10 mM HEPES pH 8.0. It is made by adding 10 mls of 1 M HEPES pH 8 and 5 mls of $NH_4Cl$ to the PM074 recipe (final volume of 1 L). In some examples, additional media with controlled ammonium levels was made by adjusting the ammonium concentration of PM074 and adding additional Hepes buffer.

For colony PCR screening, a small amount of cells from a colony to be screened was suspended into 100 μl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (Handbook available at qiagen.com). The primers used to detect the insertion of the donor fragment into the targeted locus of the cpSRP54-6676 gene were SEQ ID NO:50 and SEQ ID NO:51. Based on the PCR-based colony screening, knockout strain GE-15274 was tested for reduced chlorophyll, photosynthetic properties, and productivity.

Additional genes of the SRP54 pathway for insertion of proteins into the thylakoid membranes were also disrupted using synthesized guide RNAs that were introduced, along with the "universal donor" HygR cassette DNA (SEQ ID NO:45) into Cas9 Editor line GE-6791 in the same way. For disruption of the gene encoding the Ftsy polypeptide (SEQ ID NO:52, coding sequence SEQ ID NO:53), the target sequence used in making the guide RNA was SEQ ID NO:54. For disruption of the gene encoding the ALB3 polypeptide (SEQ ID NO:55, coding sequence SEQ ID NO:56), the target sequence used in making the guide RNA was SEQ ID NO:57. In addition, as a control, the gene encoding the cytosolic SRP54 polypeptide (cytoSRP54, SEQ ID NO:58, encoded by SEQ ID NO:59) was targeted for knockout using a guide sequence that included target sequence SEQ ID NO:60). In each case the HygR cassette donor DNA (SEQ ID NO:45) was co-transformed into Cas9 Editor line GE-6791 with the guide sequence. Based on PCR-based colony screening, each of the resulting knockout strains GE-15272 (Ftsy Knockout), GE-14315 (ALB3 Knockout), and GE-14792 (Cytosolic SRP54 Knockout) was tested for chlorophyll content, photosynthetic properties, and productivity.

Example 2. Photosynthetic Parameters of the *Nannochloropsis* cpSRP54 Pathway Knockout Strains Chlorophyll contents of the *N. gaditana* knockout mutants GE-14792, GE-15272, GE-15274, and GE-15315 were determined by extracting chlorophyll from cell pellets using a DMSO:Acetone procedure. In this procedure, 500 μl of culture was aliquoted into a 2 ml microcentrifuge tube and pelleted by centrifugation for 3 minutes at 12,000 rpm at room temperature. The supernatant was carefully removed and the cell pellet was resuspended in 1 ml of 1:1 DMSO:Acetone. The sample was then vortexed for 2-5 minutes at room temperature. Cell debris was pelleted by centrifugation for 3 minutes at 12,000 rpm. The supernatant absorbance was then read on a spectrophotometer blanked with a 1:1 DMSO:Acetone solution at 663 nm and 720 nm. The chlorophyll content was quantified by subtracting the 720 nm absorbance value from the 663 nm absorbance value. The resulting net absorbance value was then multiplied by the dilution factor and extinction coefficient of 20.15 to determine the μg/ml concentration or 18.01 to determine the μmol/ml concentration of chlorophyll. The amount of chlorophyll was calculated per cell and per of biomass (TOC). (Biomass assessment was performed as provided in Example 3.) The values shown in FIG. 3A (chlorophyll per total organic carbon) and FIG. 3B (chlorophyll per cell) are the averages of two replicate cultures.

The *N. gaditana* cpSRP54 knockout mutant strain GE-15274 showed a very modest reduction in chlorophyll (FIG. 3A), having approximately 13% less chlorophyll than the wildtype strain. The Ftsy knockout strain GE-15272 showed a similar chlorophyll/TOC reduction (an approximately 16% reduction), while the Alb3 knockout strain GE-15315 had a more significant level of chlorophyll reduction, approximately 44%. Surprisingly though, of all the knockout mutants the cytosolic SRP54 knockout mutant, included as a control, had the most severe reduction in chlorophyll, a reduction of approximately 60%.

In addition, carbon fixation and oxygen evolution of *N. gaditana* cpSRP54 knockout strain GE-15274 as well as Ftsy knockout strain GE-15272, Alb3 knockout strain GE-15315, and the cytosolic SRP54 knockout mutant GE-14792 were measured. Oxygen evolution by the *Nannochloropsis* cpSRP54 knockout mutant strain was measured using a Clark-type oxygen electrode. An aliquot of cells containing 5 μg chlorophyll per ml, or approximately $10^7$ cells, was transferred into the oxygen electrode chamber which was illuminated at varying light intensities to generate the oxygen evolution versus irradiance curve of FIG. 4A. Sodium bicarbonate (5 mM) was also added to the chamber to ensure the cells were not carbon-limited. FIG. 4B, providing the values with the lamp at 1500 μmol photons $m^{-2}$ $sec^{-1}$, shows that the *N. gaditana* cpSRP54 mutant showed a somewhat increased rate of oxygen evolution, a measure of photosynthesis, with respect to wild type, while the cytosolic SRP54 knockout had a markedly reduced rate of oxygen evolution with respect to wild type cells.

In the carbon fixation assay, 70 μl of $^{14}C$-labeled sodium carbonate (Perkin Elmer $^{14}C$ $NaHCO_3$; 50.8 mCi/mmol; 1 mCi/mL) was mixed with 3 ml of the culture at a concentration of 5 μg Chl/ml that had been dark acclimated for at least 10 min. Two samples of each culture were prepared. The first sample was placed in front of LED light panel for 10 min, after which 250 μl of 2N hydrochloric acid (Fisher A508-P212) was added and mixed with the culture. The second sample was immediately mixed with 2N hydrochloric acid as a non-illuminated control. All samples acidified and vented overnight before 5 ml of UltimaGold A/B scintillation counter solution was added (Perkin Elmer). Samples were read on a LS6500 multi-purpose scintillation counter (Beckman). Scintillation counts were used to calculate the carbon fixation rates for each sample. The *N. gaditana* cpSRP54 knockout mutant (GE-15274), along with the Ftsy knockout mutant (GE-15272) showed somewhat increased rates of carbon fixation with respect to wild type on a per cell basis (FIG. 5A), while the cytosolic SRP54 knockout mutant cellular rate of carbon fixation was strongly reduced, by about 43%. The rate of carbon fixation by the Alb3 mutant (GE-15315) was similar to the wild type rate. The values shown in FIG. 5A are the averages of two replicate cultures.

Example 3. Productivity Assay of *Nannochloropsis* cpSRP54 Knockout Strain

To test productivity of the cpSRP54 knockout strain, a semicontinuous assay was used. In these assays the cpSRP54 knockout strain GE- and wild type strain WT-3730 were grown up in PM074 medium. The scale-up cultures were used to inoculate 225 $cm^2$ rectangular tissue culture flasks, each of which contained a final total volume of 550 ml of culture after inoculation. Three cultures were tested per strain. The cultures were inoculated so that each 550 ml culture had an initial $OD_{730}$ of 0.9. A typical inoculum volume was approximately 200 ml of scale-up culture that was added to approximately 350 ml of assay culture medium (PM074). The flasks included stir bars and had stoppers having inserted tubing connected with syringe filters for delivering $CO_2$ enriched air (1% $CO_2$, flow rate, 300 ml per min) that was bubbled through the cultures. The flasks were set in a water bath programmed to maintain a constant temperature of 25° C. on stir plates set to 575 rpm during the assay period. Culture flasks were masked with an opaque white plastic to provide a 31.5 $cm^2$ rectangular opening for irradiance to reach the culture. The flasks were aligned with the width (narrowest dimension) against an LED light bank that was programmed with a light/dark cycle and light profile that increased until "solar noon" and then declined to the end of the light period. The light profile was designed to mimic a spring day in Southern California: 14 h light:10 h dark, with the light peaking at approximately 2000 μE.

Cultures were diluted daily at mid-day, when the light intensity was at its peak, by removing 30% of the volume (165 mls) and replacing it with the same volume of the assay medium (PM074) plus an additional 10 ml of deionized water to make up for evaporation (included in the make-up medium). A 30% dilution rate was empirically determined as the most productive dilution rate for *Nannochloropsis*. Daily lipid and biomass productivities were only calculated for cultures that had reached steady state (where the increase in growth was equal to the dilution factor for the assay).

The semi-continuous assays were run for approximately seven days. Daily lipid (FAME) and biomass (TOC) productivities were calculated from cultures that had reached steady state standing crop TOC and FAME density. Volumetric FAME and TOC productivities in (mg/L/day) were calculated by multiplying the volumetric FAME and TOC amounts by the 30% dilution rate. Aerial productivities (g/m2/day) were calculated by dividing the total productivity of the culture by the size of the aperture through which irradiance was permitted:

$$\frac{(\text{volumetric productivity})\ \text{mg}}{\text{L} * \text{day}} * \frac{0.55\ \text{L}}{0.00315\ \text{m}^2} * \frac{\text{g}}{1000\ \text{mg}} = \frac{\text{g}}{\text{m}^2 * \text{day}}$$

The results of the semicontinuous productivity assay are provided in FIG. 5B, FIGS. 6A, and 6B. FIG. 5A shows that the cpSRP54 GE-15274 mutant provides no improvement in biomass productivity, having approximately the same biomass (TOC) productivity as does wild type strain WT-3730, while all of the other knockouts show slight deficiencies. FIG. 6A shows that GE-15274 has slightly less daily FAME productivity that the wild type strain. Surprisingly however, the cytosolic SRP54 knockout (GE-14792) shows a substantial increase in FAME productivity over the course of the assay, an approximately 25% improvement over wild type FAME productivity. None of the other knockout mutants, all of which have lesions in chloroplastic SRP thylakoid protein insertion components, show any increase in FAME productivity, but instead have slight to moderate decreases in FAME productivity with respect to wild type cells. The increased FAME productivity of the cytosolic SRP54 knockout strain is reflected in the significantly higher FAME/TOC ratio of the GE-14792 strain over the course of the assay (FIG. 6B), while the FAME/TOC ratio of the chloroplastic SRP54 knockout (GE-15274) is no greater than that of wild type, demonstrating that the strain provides no advantage in lipid production.

Example 4. UV Mutagenesis of a *Parachlorella* Strain

To isolate LIHLA mutants from a chlorophyte, or green algal species, cells of *Parachlorella* strain WT-01185, were mutagenized with UV and selected based on low chlorophyll fluorescence after low light acclimation. The *Parachlorella* strain used for mutagenesis, WT-01185, was isolated from a marine environment. *Parachlorella* WT-01185 cells were grown to mid-log phase and then diluted to $1\times10^6$ cells/mL with growth medium PM119. The cell suspensions were transferred by pipet to a 100 mm Petri dish and placed within a STRATALINKER® 2400 UV crosslinker (Agilent Technologies, Santa Clara, Calif.) with the plate lid removed. UV irradiation was carried out with 10,000, 25,000, and 50,000 $\mu J/cm^2$. After irradiation, cell suspensions were pipetted into a shake flask wrapped in foil to prevent light exposure for twenty-four hours during recovery.

PM119 media includes: 35 ppt Instant Ocean Salts (Aquatic Eco Systems; Apopka, Fla.), 5× Guillard's F/2 marine water enrichment solution (50× stock from Sigma-Aldrich, St. Louis, Mo., cat. No. G0154; final concentrations of components in media: 4.413 mM Sodium nitrate; 0.16 mM Sodium phosphate monobasic; 0.103 μM Biotin; 0.240 μM Cobalt chloride.$6H_2O$; 0.200 μM Cupric sulfate.$5H_2O$; 0.0585 mM Disodium EDTA.$2H_2O$; 4.54 μM Manganese chloride.$4H_2O$; 0.124 μM Sodium molybdate.$2H_2O$; 1.48 μM Thiamine.HCl; 0.0185 μM Vitamin $B_{12}$; 0.382 μM Zinc sulfate.$7H_2O$).

Example 5. Screens of *Parachlorella* sp. Strain WT-01185 LIHLA Mutants

Following mutagenesis and recovery as described in Example 4, cells were screened for the locked-in high light acclimated" ("LIHLA") phenotype described in U.S. Patent Application Publication No. US2014/0220638, incorporated herein by reference. The mutagenized cells were allowed to grow from between one and five days in low (100 μmol photons $m^{-2}$ $sec^{-1}$) light, after which they were sorted by flow cytometry using a BD FACSAria II flow cytometer (BD Biosciences, San Jose, Calif.) to select low chlorophyll fluorescence cells. In general, the portion of cells with the lowest approximately 0.5 to 2% of chlorophyll fluorescence compared to the total population of cells was selected. Further primary screening of putative LIHLA colonies isolated through flow cytometry was conducted through the selection of pale green or yellow colonies visually after sorted cells were plated. In order to screen putative LIHLA colonies from other reduced pigment mutants and false positives, selected colonies were subjected to a medium-throughput secondary cultivation screen to acclimate the isolates to low light conditions prior to photo-physiological measurements. Chlorophyll fluorescence was monitored during low light acclimation to select colonies that retained the reduced chlorophyll fluorescence characteristic of the high light acclimated state. Clones that were selected demonstrated only small increases in chlorophyll (relative to wild type cells) when transferred from high to low light. This trait, of retaining substantially the same low chlorophyll content of a high light acclimated cell even when acclimated to low light conditions, is an identifying characteristic of the LIHLA mutants (see U.S. Patent Application Publication No. US2014/0220638, incorporated herein by reference in its entirety).

Cell lines that retained reduced chlorophyll fluorescence at higher culture density (which promotes a low light acclimation response in wild type) were then further screened through more advanced photo-physiological measurements following acclimation to low light.

Example 6. Functional Characterization of LIHLA Mutants NE-07542, NE-07548, NE-07557, NE-07564, and NE-07837

Among the LIHLA strains that were found to have reduced chlorophyll under low light conditions were five isolates that were analyzed in detail: mutants NE-07542, NE-07548, NE-07557, NE-07564, and NE-07837. Chlorophyll content of mutants was determined by extracting cells with methanol, and analyzing the supernatant by spectrophotometry. Briefly, 200 μl aliquots of culture were pipeted into 2.0 ml twist top tubes and pelleted using a table top microcentrifuge at 12,000 rpm for 5 minutes. The supernatants were aspirated off of the pellets, and each pellet was resuspended in 1.5 ml 99.8% methanol. 0.5 ml of glass beads (212-300 m diameter) were added to each vial and the vials were incubated on ice for 1 min prior to bead beating 3 times for 1 min, placing each vial on ice after each 1 min bead-beating. The tubes were centrifuges on the table top microcentrifuge at 15,000 rpm for 5 minutes. The resulting pellets were white. One ml of each supernatant was pipeted into a disposable cuvette and absorption wavelengths were read immediately at 720 nm, 696 nm, 665 nm, 652 nm, and 632 nm wavelengths after blanking the spectrophotometer with 99.8% methanol. To calculate the concentration of total chlorophyll, the following equation was used: Total Chlorophyll [g $m^{-3}$]=28.6473(A632)+12.9405(A652)+0.6845 (A665)+5.2230(A696). For Chlorophyll a concentration, the equation used was Chlor a [g $m^{-3}$]=−2.0780(A632)−6.5079 (A652)+16.2127(A665)−2.1372(A696). For Chlorophyll b concentration, the equation used was Chlor b [g m−3]=−2.9450(A632)+32.1228(A652)−13.8255(A665)−3.0097 (A696).

As seen in Table 1, the NE-07542, NE-07548, NE-07557, NE-07564, and NE-07837 strains were found to have reduction in chlorophyll that ranged from 62-74% as compared to wild type following low light acclimation. The ratio of chlorophyll a to chlorophyll b (an indication of the selective reduction of antenna chlorophyll) was greatly increased with respect to the wild type chlorophyll a to b ratio of 2.4:1. Mutant ratios of chlorophyll a to chlorophyll b ranged from about 3.1:1 to about 4.3:1.

TABLE 1

Chlorophyll content of Parachlorella LIHLA strains compared to wild type.

| STRAIN | a:b ratio | % increase a:b ratio | pg Chl/cell | % reduction Chl |
|---|---|---|---|---|
| WT-01185 (wild type) | 2.4 | — | 0.67 | — |
| NE-07542 | 3.1 | 29% | 0.26 | 60% |
| NE-07548 | 3.5 | 46% | 0.25 | 62% |
| NE-07557 | 4.3 | 79% | 0.23 | 66% |
| NE-07564 | 3.7 | 54% | 0.25 | 62% |
| NE-07837 | 3.0 | 25% | 0.30 | 55% |

Fluorescence based PSII photo-physiological parameters were used to identify strains with similar or increased maximal PSII quantum yield ($F_v/F_m$) and higher photochemical quenching coefficient (qP) than the wild type strain, determined over 13 irradiance levels. Fv/Fm was measured using a Dual PAM fluorometer (Walz, Effeltrich, Germany). A 3 ml aliquot of cells with a cell density $1\times10^7$ cells per ml (approximately 5 mg chlorophyll per ml) was dark adapted for five minutes, after which a low intensity measuring beam was used to obtain $F_0$. The cells were then exposed to saturating light to close all reaction centers, and then a second low intensity measuring beam was used for obtaining $F_m$ (Maxwell and Johnson, (2000) *J. Exper. Bot.* 51: 659-668). FIG. 7A shows the *Parachlorella* isolates demonstrated higher $F_v/F_m$ values at all irradiances tested, i.e., from approximately 10 μmol photons $m^{-2}$ $sec^{-1}$ to approximately 2840 μmol photons $m^{-2}$ $sec^{-1}$.

Figure 8:
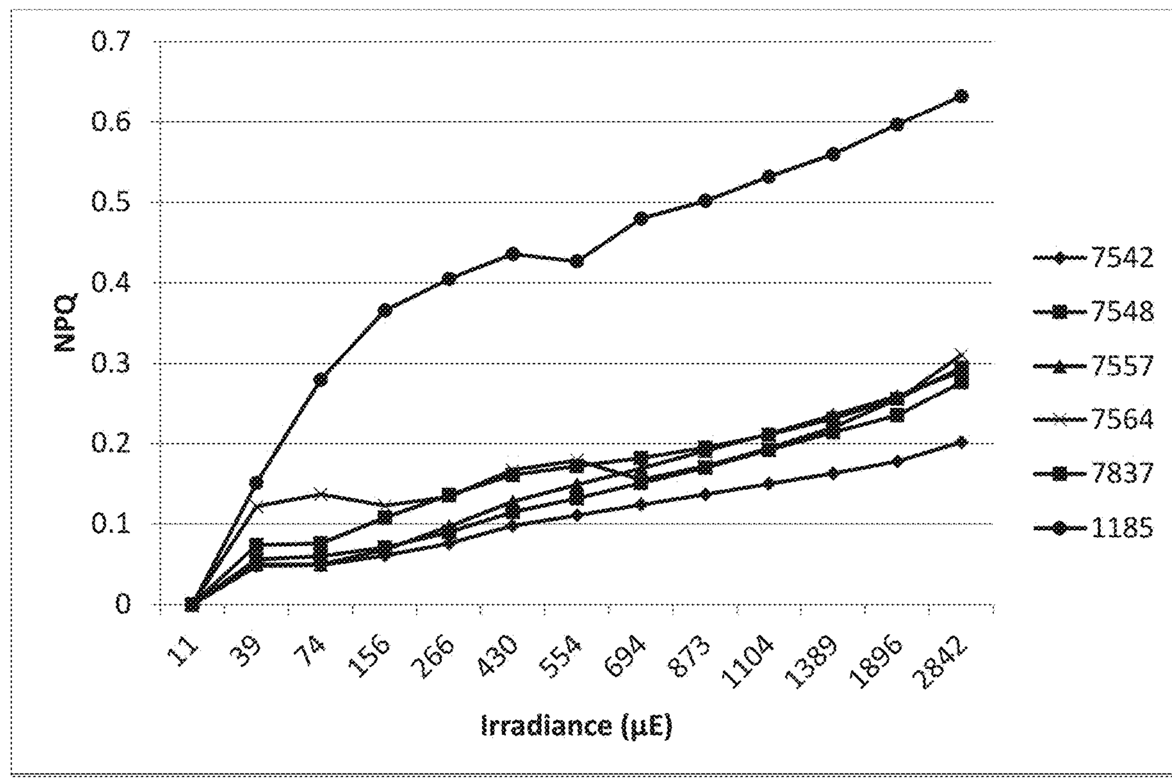
FIG. 8 is a graph of nonphotochemical quenching (NPQ) in response to increasing light intensity in cpSRP54 mutants NE-07542, NE-07548, NE-07557, NE-07564, and NE-07837.

Photochemical quenching, or qP, a measure of the proportion of open PSII centers, and nonphotochemical quenching, or NPQ, were also measured using a Dual PAM fluorometer (Walz, Effeltrich, Germany) over a range of light intensities. FIG. 7B shows the mutants had higher qP values for all irradiances greater than about 10 μmol photons $m^{-2}$ $sec^{-1}$, for example, at all irradiances from about 40 μmol photons $m^{-2}$ $sec^{-1}$ to about 2840 μmol photons $m^{-2}$ $sec^{-1}$. FIG. 8 shows the mutants also had lower NPQ at all irradiances greater than about 10 μmol photons $m^{-2}$ $sec^{-1}$, for example, at all irradiances from about 40 μmol photons $m^{-2}$ $sec^{-1}$ to about 2840 μmol photons $m^{-2}$ $sec^{-1}$.

In addition to reduced chlorophyll content, these strains demonstrated higher qP (FIG. 7B), lower NPQ (FIG. 8), the mutants demonstrated higher photosystem II electron transport rates (FIG. 9A) at all light intensities greater than about 75 μmol photons $m^{-2}$ $sec^{-1}$ that were tested (up to approximately 2800 μmol photons $m^{-2}$ $sec^{-1}$), and increased photosynthetic efficiency (FIG. 9B) at all light intensities greater than about 40 μmol photons $m^{-2}$ $sec^{-1}$ that were tested (up to approximately 2800 μmol photons $m^{-2}$ $sec^{-1}$), demonstrating that these strains had the characteristics of "LIHLA" mutants (see US 2014/0220638, incorporated by reference herein).

Example 7. Genotyping of *Parachlorella* LIHLA Mutants

Figure 10:
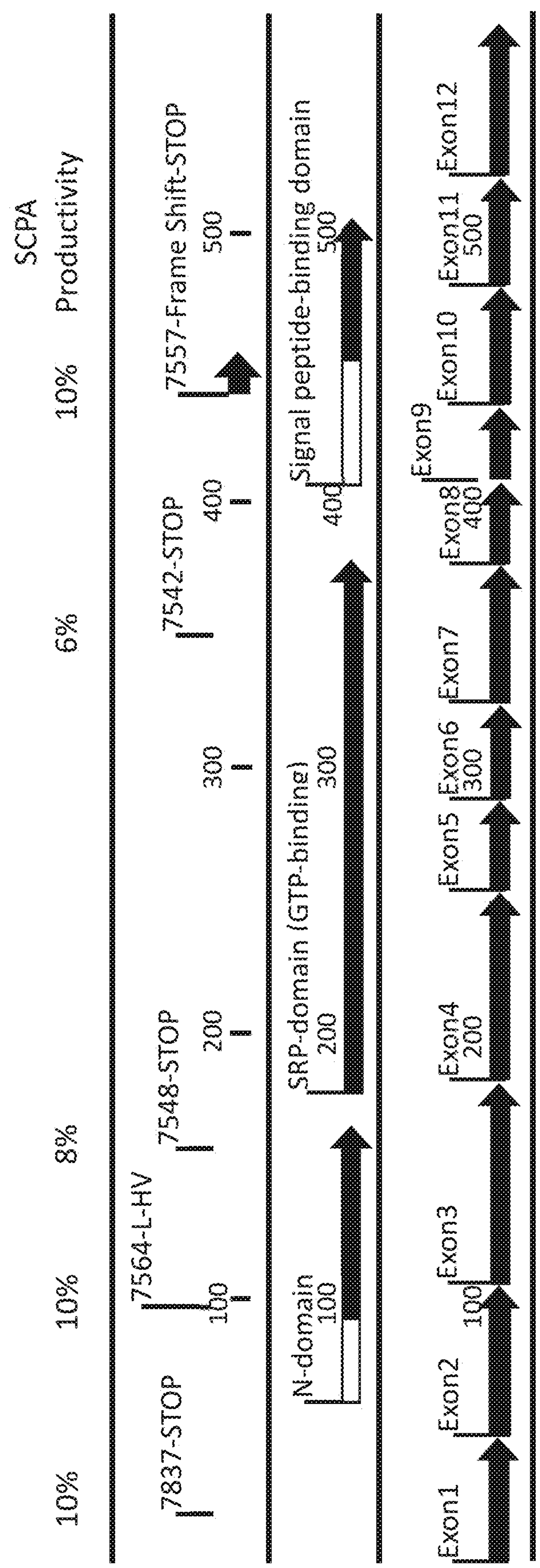
FIG. 10 is a schematic diagram of the *Parachlorella* cpSRP54 gene showing the location of the mutations in mutants NE-07542, NE-07548, NE-07557, NE-07564, and NE-07837.

Genome sequencing of *Parachlorella* LIHLA mutants NE-07542, NE-07548, NE-07557, NE-07564, and NE-07837 determined that each had a mutation within a SRP54 gene (cDNA sequence provided as SEQ ID NO:1, amino acid sequence of encoded polypeptide provided as SEQ ID NO:2), characterized by two domains found in this class of protein: the SRP GTPase domain (Pfam 00448) and the SRP Signal Peptide Binding domain (Pfam 02978). In addition, the *Parachlorella* polypeptide of SEQ ID NO:2 had a region with homology to the SRP54-N or "SRP54 helical bundle" SMART domain 00693. This domain corresponds to Pfam 02881; however, the sequence did not have a strong enough fit with Pfam 02881 to qualify for inclusion in Pfam 02881 (the bit score was lower than the cutoff value). FIG. 10 provides a diagram of the cpSRP54 gene showing the conserved domains and the positions and of mutations confirmed for the cpSRP54-associated LIHLA mutants.

Confirmation of the positions of the genetic lesions in the mutants was through a combination of chromosome walking techniques, PCR, and DNA sequencing, including genome sequencing using an in-house MiSeq sequencer (Illumina, San Diego, Calif.). For mutant genome re-sequencing, whole genomic DNA of the *Parachlorella* mutants were used for Nextera DNA library preparation according to the recommended protocol (Illumina Inc., San Diego, Calif.). The libraries generated were sequenced by paired-end sequencing on an Illumina MiSeq instrument.

TABLE 2

Molecular basis of Mutations in the cpSRP54 gene of Parachlorella LIHLA Strains

| STRAIN | MUTATION | EXON |
| --- | --- | --- |
| NE-07542 | Stop gained | 7 |
| NE-07548 | Stop gained | 3 |
| NE-07557 | Frame shift | 10 |
| NE-07564 | Codon change and Insertion | 2 |
| NE-07837 | Stop gained | 1 |

Example 8. cpSRP54 Genes and Polypeptides

As depicted in FIG. 10, several mutations were identified in the *Parachlorella* cpSRP54 gene that resulted in lower chlorophyll and higher photochemical photosynthetic efficiency as compared to the parental wild-type strains. Mutations resulting in a LIHLA phenotype were K348*, Y156*, -438, L97HV, L19*, where * denotes a stop codon and - (a dash) denotes an insertion or deletion caused frameshift effecting the remainder of the protein.

To determine whether the mutated SRP54 gene was a chloroplastic SRP54 gene, alignments of known sequences of chloroplastic SRP54 polypeptides (cpSRP54's) were used to build a Hidden Markov Model (HMM) for chloroplastic SRP54 proteins. The identification of chloroplastic SRP54 sequences was based on manual curation and alignment of SRP54 sequences by Trager et al. (2012) *The Plant Cell* 24:4819-4836 (see, Supplemental FIG. 4 and Supplemental Table 1, available at plantcell.org/cgi/doi/10.1105/tpc.112.102996). The HMM for the cpSRP54 was then used to search the full collection of sequences from the proprietary *Parachlorella* WT01185 nuclear genome annotation, proprietary *Nannochloropsis gaditana* WE03730 nuclear genome (v2), and proprietary *Nannochloropsis gaditana* WE03730 cDNA annotations. In addition, cpSRP54 alignments taken directly from the SRP database available at rnp.uthscsa.edu/rnp/SRPDB/srpprotein.html were used to build an SRP54 HMM to identify non-chloroplastic SRP54 genes in the same genomes.

Figure 11:
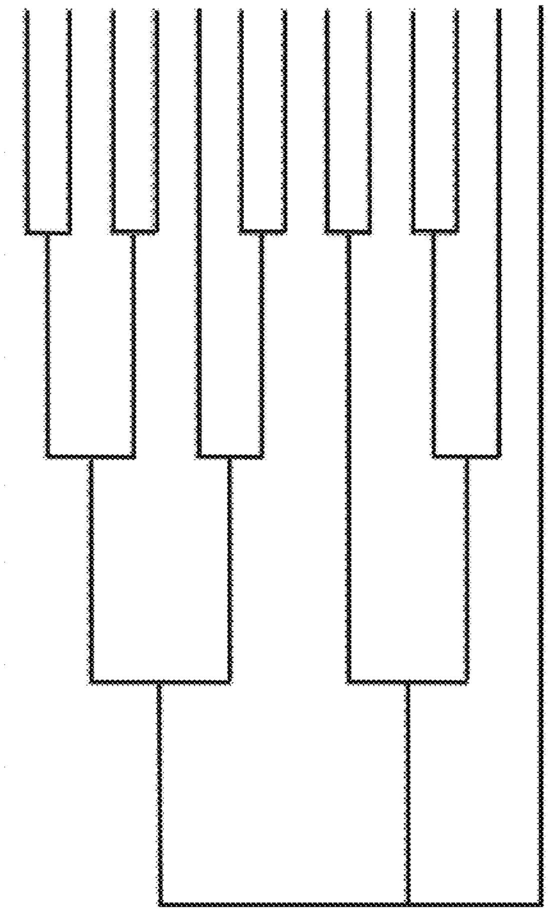
FIG. 11 is a tree showing the relationship of various algal cpSRP54 polypeptides.

Significant homology was found between the *Parachlorella* WT-01185 cpSRP54 (SEQ ID NO:2), and SRP54 polypeptides of other microalgal species that are characterized as chloroplastic Trager et al. (2012), supra). For example, the *Parachlorella* cpSRP54 polypeptide (SEQ ID NO:2) has 56% amino acid identity to the SRP54 polypeptide of *Chlamydomonas reinhardtii* (A8J758; SEQ ID NO:3) having Genbank accession EDP00260 and gene identifier (GI) 158274478; 53% amino acid identity to the SRP54 polypeptide of *Micromonas pusilla* (C1MLE1; SEQ ID NO:4) having Genbank accession EEH59526 and GI:226462234; 53% amino acid identity to the SRP54 polypeptide of *Micromonas* sp. (C1FE02; SEQ ID NO:5) having Genbank accession ACO68481 and GI:226522498; 53% amino acid identity to the SRP54 polypeptide of *Paulinella chromatophora* (B1X3Q8; SEQ ID NO:6) having Genbank accession ACB42577 and GI:171191615; 53% amino acid identity to the SRP54 polypeptide of *Ostreococcus lucimarinus* (A4RQK2; SEQ ID NO:7) having Genbank accession ABO94038 GI:144575969; 49% amino acid identity to the SRP54 polypeptide of *Ostreococcus tauri* (Q01H03; SEQ ID NO:8) having GI:122162028; 50% amino acid identity to the SRP54 polypeptide of *Volvox carteri* (D8UEN3; SEQ ID NO:9) having Genbank accession EFJ41797 and GI:300257550; 50% amino acid identity to the SRP54 polypeptide of *Phaeodactylum tricornutum* (B7FXT4; SEQ ID NO:10) having Genbank accession EEC48599 and GI:217408666; 50% amino acid identity to the SRP54 polypeptide of *Nannochloropsis gaditana* (SEQ ID NO:11); 49% amino acid identity to the SRP54 polypeptide of *Thalassiosira pseudonana* (B8BUG8; SEQ ID NO:12) having Genbank accession EED94755 and GI:220976428; 49% amino acid identity to the SRP54 polypeptide of *Aureococcus anophagefferens* (323456635; SEQ ID NO:13) having Genbank accession EGB12501 and GI:323456635; 49% amino acid identity to the SRP54 polypeptide of *Ectocarpus siliculosus* (D8LN22; SEQ ID NO:14) having Genbank accession CBN76263, GI:299116639. The relationship of these proteins to the *Parachlorella* WT-01185 cpSRP54 (SEQ ID NO:2) is shown in the diagram of FIG. 11.

TABLE 3

Algal cpSRP54 Proteins

| Species | Protein ID | Percent Identity to Parachlorella WT-01185 cpSRP54 |
| --- | --- | --- |
| *Ostreococcus tauri* | Q01H03 | 49% |
| *Ostreococcus lucimarinus* | A4RQK2 | 53% |
| *Micromonas pusilla* | C1MLE1 | 53% |
| *Micromonas* sp | C1FE02 | 53% |
| *Chlamydomonas reinhardtii* | A8J758 | 56% |
| *Volvox carteri* | D8UEN3 | 50% |
| *Ectocarpus siliculosus* | D8LN22 | 44% |
| *Nannochloropsis gaditana* | Unpublished | 50% |
| *Thalassiosira pseudonana* | B8BUG8 | 49% |

TABLE 3-continued

| Algal cpSRP54 Proteins | | |
|---|---|---|
| Species | Protein ID | Percent Identity to Parachlorella WT-01185 cpSRP54 |
| *Phaeodactylum tricornutum* | B7FXT4 | 51% |
| *Aureococcus anophagefferens* | 323456635 | 46% |
| *Paulinella chromatophora* | B1X3Q8 | 53% |

All of the identified putative orthologs with the exception of SEQ ID NO:8 (*Ostreococcus tauri*) are observed to have the same overall domain structure i.e., progressing from the amino terminus toward the carboxy terminus, the SRP54 N or "helical bundle" domain (pfam 02881) (amino acids 67-163 of SEQ ID NO:2), followed by the SRP GTPase domain (SEQ ID NO:14, which is amino acids 180-351 of SEQ ID NO:2) followed by the SRP Signal Peptide Binding domain (pfam 02978) (amino acids 404-504 of SEQ ID NO:2). The *Parachlorella* cpSRP54 (SEQ ID NO:2) includes an SRP54 B domain according to SMART domain models (smart.embl-heidelberg.de), but does not meet the criteria for inclusion in Pfam PF02881. Therefor recruitment to Pfam PF02881 is not a criterion for characterization as a chloroplastic SRP54.

The most conserved domain among the putative cpSRP54 orthologs is the GTPase domain (pfam PF00448, "SRP54-type protein, GTPase domain", gathering cut-off of 22.7). SEQ ID NO:15 (the GTPase domain of the *Parachlorella* cpSRP54) has 74% identity the GTPase domain of the *Chlamydomonas* SRP54 (SEQ ID NO:16), 71% identity the GTPase domain of the *Micromonas pusilla* SRP54 (SEQ ID NO:17), 71% identity the GTPase domain of the *Micromonas* sp. SRP54 (SEQ ID NO:18), 68% identity the GTPase domain of the *Paulinella chromatophora* SRP54 (SEQ ID NO:19), 69% identity the GTPase domain of the *Ostreococcus lucimarinus* SRP54 (SEQ ID NO:20), 56% identity the GTPase domain of the *Ostreococcus tauri* SRP54 (SEQ ID NO:21), 78% identity the GTPase domain of the *Volvox carteri* SRP54 (SEQ ID NO:22), 68% identity the GTPase domain of the *Phaeodactylum tricornutum* SRP54 (SEQ ID NO:23), 64% identity the GTPase domain of the *Nannochloropsis gaditana* SRP54 (SEQ ID NO:24), 66% identity the GTPase domain of the *Thalassiosira pseudonana* SRP54 (SEQ ID NO:25), 59% identity the GTPase domain of the *Aureococcus anophagefferens* SRP54 (SEQ ID NO:26), and 62% identity the GTPase domain of the *Ectocarpus siliculosus* SRP54 (SEQ ID NO:27).

The observed mutations in the LIHLA mutants were found to occur N-terminal of the N-domain (7837 mutation) and within the N-domain (7564 and 7548 mutations), at the C-terminal end of the SRP (GTP binding) domain (7542 mutation) and within the signal peptide binding domain (7557 mutation). Interestingly, the only mutation localized to the GTPase domain was the NE-07542 mutation that generated a stop codon at the very end of exon 7 (the codon encoding amino acid 169 of exon 7 was altered to generate a stop codon within the 172 codon exon).

Example 9. Oxygen Evolution and Carbon Fixation Rates of cpSRP54 Mutants

Oxygen evolution by the *Parachlorella* LIHLA strains was measured using a Clark-type oxygen electrode. An aliquot of cells containing 5 μg chlorophyll per ml, or 107 cells, was transferred into the oxygen electrode chamber which was illuminated with a lamp at 1500 μmol photons m−2 sec−1. Sodium bicarbonate (5 mM) was also added to the chamber to ensure the cells were not carbon-limited.

LIHLA cpSRP54 mutants were also assayed to determine their rate of carbon fixation compared to wild type. In this assay, 70 μl of $^{14}$C-labeled sodium carbonate (Perkin Elmer $^{14}C\ NaHCO_3$; 50.8 mCi/mmol; 1 mCi/mL) was mixed with 3 ml of the culture at 5 μg Chl/ml that had been dark acclimated for at least 10 min. Two samples of each culture were prepared. The first sample was placed in front of LED light panel for 10 min, after which 250 μl of 2N hydrochloric acid (Fisher A508-P212) was added and mixed with the culture. The second sample was immediately mixed with 2N hydrochloric acid as a non-illuminated control. All samples acidified and vented overnight before 5 ml of UltimaGold A/B scintillation counter solution was added (Perkin Elmer). Samples were read on a LS6500 multi-purpose scintillation counter (Beckman). Scintillation counts were used to calculate the carbon fixation rates for each sample. All tested mutants had decreased carbon fixation rates per cell compared to WT-01185.

Table 4 shows that the cpSRP mutants had increased chlorophyll a to chlorophyll b ratios and a reduced amount of chlorophyll per cell with respect to wild type progenitor strain WT-01185, as expected for reduced antenna mutants in chlorophytes (green algae). The chlorophyll a:b ratios ranged from 3.0 to 4.3, as compared with the wild type chlorophyll a:b ratio of 2.4. The reduction in chlorophyll per cell in the cpSRP54 mutants was substantial, ranging from 55% to 66% in the cpSRP54 mutants. The carbon fixation rates on a per chlorophyll basis were much higher in the mutants than the wild type rates, with the increase over the wild type carbon fixation rate varying between 54% and 108%. Oxygen evolution per chlorophyll also increased dramatically in the mutants, ranging a 120% increase over wild type to a 398% increase over wild type, i.e., at rates of approximately two-fold to approximately five-fold that of wild type on a per chlorophyll basis.

TABLE 4

| chlorophyll content, carbon fixation and oxygen evolution rates. | | | | | | |
|---|---|---|---|---|---|---|
| STRAIN | a:b ratio (% incr) | pg Chl/cell (% decr) | mg C fi/cell (% change) | mg C fix/Chl (% change) | pmol $O_2$ evol/cell (% change) | $O_2$ evol/Chl (% change) |
| WT-01185 | 2.4 (—) | 0.67 (—) | 1.13E−09 (—) | 2.11 (—) | 0.078 (—) | 168 (—) |
| NE-07542 | 3.1 (29%) | 0.26 (60%) | 8.85E−10 (−22%) | 3.81 (81%) | 0.070 (−12%) | 370 (120%) |
| NE-07548 | 3.5 (46%) | 0.25 (62%) | 5.87E−10 (−48%) | 3.53 (67%) | 0.099 (26%) | 453 (169%) |

TABLE 4-continued chlorophyll content, carbon fixation and oxygen evolution rates.

| STRAIN | a:b ratio (% incr) | pg Chl/cell (% decr) | mg C fi/cell (% change) | mg C fix/Chl (% change) | pmol $O_2$ evol/cell (% change) | $O_2$ evol/Chl (% change) |
|---|---|---|---|---|---|---|
| NE-07557 | 4.3 (79%) | 0.23 (66%) | 7.02E−10 (−38%) | 4.38 (108%) | 0.140 (77%) | 694 (313%) |
| NE-07564 | 3.7 (54%) | 0.25 (62%) | 7.25E−10 (−36%) | 3.85 (82%) | 0.112 (43%) | 838 (398%) |
| NE-07837 | 3.0 (25%) | 0.30 (55%) | 7.90E−10 (−30%) | 3.25 (54%) | ND | ND |

Example 10. cpSRP54 Mutants in Semi-Continuous Productivity Assays

To determine whether the cpSRP54 mutants were more productive in culture, photoautotrophic cultures of the mutants were grown over several da0ys in semi-continuous mode with culture samples removed daily for biomass determination. In one such assay, the mutants were grown under a diel (light/dark) cycle with constant high intensity light during the light phase. In this assay PM119 culture medium in a 75 cm2 flask was inoculated with seed culture of a given mutant strain so that the initial 165 ml culture had an initial OD730 of 0.15. Three cultures were initiated per strain. The flasks had stoppers having tubing connected with syringe filters for delivering CO2 enriched air (1% CO2; flow rate, 165 ml per min) that was bubbled through the cultures. The flasks were aligned with the width (narrowest dimension, 2.8 cm) against an LED light bank that was programmed with a "square wave" light/dark cycle where the light was off for 8 hours and then turned on immediately to peak intensity of between 1900 and 2000 μmol photons m−2 sec−1 for 16 hours ("High Light" or HL2000 assay). The depth of the cultures (the distance from the wall of the flask nearest the light source to the wall at back of the flask) was approximately 8.0 cm. The cultures were diluted daily at the beginning of the light period by removing 15% (25 ml) of the culture volume and replacing it with fresh PM119 media diluted to adjust for the increase in salinity due to evaporation occurring in the cultures (212 ml di H2O to 1 L PM119 medium). Samples for TOC analysis were taken from the culture removed for the dilution. These semi-continuous small scale assays were typically run for 5 days.

In another small-scale semi-continuous assay design, the cultures were set up exactly as described for the high light diel cycle assay, but were kept at a constant (24 h./day) 1900-2000 μmol photons m−2 sec−1 for 24 hours per day ("Constant Light" CL2000 assay). The cultures were diluted daily at the beginning of the light period by removing 60% (99 ml) of the culture volume and replacing it with fresh PM119 media diluted as above to adjust for the increase in salinity due to evaporation occurring in the cultures.

Productivity for both assays was assessed by measuring total organic carbon (TOC) from the samples that were removed daily. Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of r2>0.999.

Exemplary results of the small-scale productivity assays are provided in FIGS. 12A and 12B. FIGS. 12A and 12B demonstrate that cpSRP54 mutant NE-07557 had higher productivity each day of the HL2000 assay and each day of the CL2000 assay. Productivities calculated on a per day basis are provided in Table 4 below. Table 5 also shows that each of the cpSRP54 mutants (NE-07542, NE-07548, NE-07557, NE-07564, and NE-07837) outperformed the wild type in both the HL2000 and the CL2000 productivity assays.

Example 11. cpSRP54 Mutants in Diel Light Cycle Semi-Continuous Productivity Assays LIHLA cpSRP54 mutant strains were also tested in the semi-continuous productivity assay (SCPA) designed to mimic the light exposure of algae in an outdoor pond. In this assay 500 ml of PM119 culture medium in a 225 $cm^2$ flask was inoculated with seed culture of a given mutant strain so that the initial 500 ml culture had an initial $OD_{730}$ of 0.15. Three cultures were initiated per strain. The flasks included stir bars and had stoppers having tubing connected with syringe filters for delivering $CO_2$ enriched air (1% $CO_2$, flow rate, 100 ml per min) that was bubbled through the cultures. The flasks were set in water bath set to a constant temperature of 25° C. on stir plates set to 450 rpm. The flasks were aligned with the width (the narrowest dimension, measuring approximately 4.9 cm from outer edge to outer edge) against an LED light bank that was programmed with a light/dark cycle and light profile that increased until "solar noon" and then declined to the end of the light period. The sinusoidal light profile is depicted in FIG. 13A as a graph of irradiance versus time of day. The "depth" of the flask (from the flask wall nearest the light source to the flask wall farthest from the light source) was approximately 13.7 cm. The light profile was designed to mimic a spring day in Southern California: 16 h light:8 h dark, with the light peaking at approximately 2000 μmol photons $m^{-2}$ $sec^{-1}$. The culture were diluted daily at the end of the light period by removing 40% (220 ml) of the culture volume and replacing it with fresh PM074 media diluted (88 ml di $H_2O$ to 1 L PM119 medium) to adjust for the increase in salinity due to evaporation occurring in the cultures. Samples for FAME and TOC analysis were taken from the culture removed for the dilution. Continuous assays were typically run for 10-14 days. A graphic depiction of one example of the daily productivity from a semi-continuous "Southern California spring day" assay is provided in FIG. 13A. Daily productivity measured as the average TOC of 3 identical cultures is plotted for successive days. It can be seen that the NE-07837 mutant performed consistently better than wild type on each of the nine days of the assay that was performed (FIG. 13B).

Productivity was assessed by measuring total organic carbon (TOC) as described above for the CL2000 and HL2000 assays. Table 5 provides the results of the productivity testing of the mutants All of the cpSRP54 mutants were observed to have increased productivity with respect to the progenitor wild type strain in semi-continuous culture. Three of the strains, NE-07548, NE-07557, and NE-07564 were observed to accumulate 10% more biomass than the wild type on a daily basis in the semicontinuous assay in which the light intensity was varied to mimic a spring day in Southern California. Under the same conditions, mutant strain NE-07542 demonstrated a 6% increase in biomass productivity and strain NE-07548 demonstrated an 8% increase in biomass productivity with respect to wild type.

TABLE 5

Productivity Increases of cpSRP54 Mutants with respect to Wild Type in $g/m^2$/day, standard deviation are based on the average over the 5 days sampled

| | CL2000 | | | HL2000 | | | SCPA | | |
|---|---|---|---|---|---|---|---|---|---|
| Strain | Mutant | Wild type | Percent increase over WT | Mutant | Wild type | Percent increase over WT | Mutant | Wild type | Percent increase over WT |
| NE-07542 | 32.7 ± 2.1 | 28.8 ± 3.1 | 13% | 15.8 ± 0.9 | 13.3 ± 0.9 | 18% | 12.0 ± .9 | 11.3 ± 0.5 | 6% |
| NE-07548 | 35.0 ± 2.9 | 27.0 ± 2.8 | 30% | 13.5 ± 0.7 | 11.6 ± 1.0 | 17% | 11.3 ± 0.1 | 10.5 ± 0.3 | 8% |
| NE-07557 | 33.4 ± 2.4 | 27.0 ± 2.8 | 24% | 14.2 ± 0.8 | 11.6 ± 1.0 | 23% | 11.5 ± 0.3 | 10.5 ± 0.3 | 10% |
| NE-07564 | 29.3 ± 2.8 | 23.8 ± 1.0 | 23% | 13.7 ± 0.9 | 11.6 ± 1.0 | 19% | 11.6 ± 0.4 | 10.5 ± 0.3 | 10% |
| NE-07837 | 33.6 ± 2.4 | 27.0 ± 2.8 | 24% | 16.2 ± 0.6 | 14.8 ± 0.4 | 9% | 13.4 ± 0.2 | 12.2 ± 0.2 | 10% |

Table 5 also shows that all of the cpSRP54 mutants had increases in biomass productivity over wild type cells in all of the semicontinuous assays. (The TOC values in mg/L from the samples removed on a daily basis were multiplied by the daily volume removed to provide TOC productivity in mg/day. The mg/day value was then divided by the light window size in $m^2$ to provide the productivity in $mg/m^2$/day and then divided by 1000 to provide the productivity in $g/m^2$/day. The observed productivity increases were greater in the CL2000 (constant high light) assay, ranging from about 13% to about 30%. The mutants showed slightly less improvement when grown in the 16 h high light (2000 μmol photons $m^{-2}$ $sec^{-1}$)/8 hour dark diel cycle (HL2000). In these assays, the increase in productivities of the mutants ranged from about 9% to about 20% over the wild type biomass productivity. In the SCPA, in which the cultures experienced a diel light cycle that mimicked natural daylight intensities, all of the mutants continued to have increased productivity over the wild type progenitor strain, in this case ranging from about 6% to about 10%.

Example 12. Cas9-Mediated Knockout of *Parachlorella* cpSRP54

A vector, pSGE-6709, was engineered for the expression of the *Streptococcus pyogenes* Cas9 gene in *Parachlorella*. The vector included the following three elements: 1) a Cas9 expression cassette which contained an engineered Cas9 gene codon optimized for *Parachlorella* and containing introns from *Parachlorella*, that also included an N-terminal FLAG tag, nuclear localization signal, and peptide linker (SEQ ID NO:61) operably linked to the *Parachlorella* RPS17 promoter (SEQ ID NO:62) and terminated by the *Parachlorella* RPS17 terminator (SEQ ID NO:63); 2) a selectable marker expression cassette, which contained the blasticidin resistance gene from *Aspergillus terreus* codon optimized for *Parachlorella* and containing *Parachlorella* introns (SEQ ID NO:64), operably linked to the *Parachlorella* RPS4 promoter (SEQ ID NO:65) and terminated by the *Parachlorella* RPS4 terminator (SEQ ID NO:66); and 3) a GFP reporter expression cassette, which contained the TurboGFP gene (Evrogen, Moscow, Russia) (SEQ ID NO:41), driven by the *Parachlorella* ACP1 promoter (SEQ ID NO:67) and terminated by the *Parachlorella* ACP1 terminator (SEQ ID:68).

The vector was transformed into *Parachlorella* by biolistics. Transformation of *Parachlorella* wild type strain WT-1185 was accomplished using the BioRad Helios® Gene Gun System essentially as described in US Patent Publication No. 2014/0154806, incorporated herein by reference. DNA for transformation was precipitated onto gold particles, the gold particles were adhered to the inside of lengths of tubing, and a burst of helium gas was fired through the tubing positioned within the Gene Gun to propel the DNA-coated gold particles into *Parachlorella* strain WT-1185 cells which were adhered on solid non-selective media (2% agar plates containing PM074 algal growth medium). The Helios® Gene Gun was used to fire two bullets per cell circle at 600 psi from a distance of 3-6 cm from the plate. The following day, cells were transferred onto selective medium for growth of transformed colonies.

Colonies were screened for full GFP penetrance as described in Example 1 by flow cytometry and identification of transformed strains that had a single fluorescence peak shifted to a higher value than the wild type fluorescence peak. Fully penetrant Cas9 strains demonstrating a clearly shifted fluorescence peak with respect to nontransformed cells were tested for Cas9 expression by anti-Cas9 western blotting for evidence of Cas9 expression as shown in FIGS. 2A and 2B for a *Nannochloropsis* Cas9-expressing line. Based on these screens, isolate 6709-2 was carried forward and given strain identifier GE-15699.

Example 13. Knockout of SRP54 Using Fully Penetrant *Parachlorella* Cas9 Editor Line A chimeric gRNA (SEQ ID NO:68) was designed and synthesized in vitro to target the chloroplastic SRP54 gene in *Parachlorella* (coding sequence provided as SEQ ID NO:69). GE-15699 was transformed by electroporation with 1-2 μg of purified chimeric guide RNA, and 1 μg of selectable marker DNA which contained a bleomycin resistance "BleR" gene codon-optimized for *Parachlorella* and containing introns from *Parachlorella* (SEQ ID:70). The BleR gene was operably linked to the *Parachlorella* RPS4 promoter (SEQ ID:65) and terminated by the *Parachlorella* RPS4 terminator (SEQ ID:66).

Electroporation was performed by inoculating a 100 mL seed culture inoculated to $1\times10^6$ cells/mL six days before transformation was used to inoculate a 1 L culture to $1\times10^6$ cells/mL two days before transformation. On the day of transformation, cells were pelleted by centrifugation at 5000×g for 20 minutes, washed three times with 0.1 um filtered 385 mM sorbitol, and resuspended to $5\times10^9$ cells/mL in 385 mM sorbitol. Electroporation of 100 μL concentrated cells was performed in 0.2 cm cuvettes in a BioRad Gene Pulser Xcell™ under varied conditions. The DNA used for optimization of electroporation was linearized pSG6640 including the ble and. TurboGFP expression cassettes. The TurboGFP cassette included the *Parachlorella* ACP1 promoter (SEQ ID NO:67) operably linked to the TurboGFP gene (SEQ ID NO:21 SEQ ID NO:41) and the *Parachlorella* ACP1 terminator (SEQ ID NO:68). Immediately after electroporating pre-chilled cells and cuvettes, 1 mL cold sorbitol was added and used to transfer cells into 10 mL PM074. After overnight recovery, cells were concentrated and spread onto 13 cm-diameter PM074 media containing zeocin at 250 mg/L and grown under the conditions listed in the biolistics section.

Electroporation conditions were 1.0-1.2 kV (5000-6000 V/cm), 200-300 ohms, and 25-50 μF. Use of larger quantities of DNA increased the resulting number of zeocin-resistant colonies, though the effect plateaued at amounts larger than 4 μg. Following electroporation, cells were plated on agar medium (PM130) containing 250 μg/ml zeocin to select for transformants that incorporated the bleR cassette. Transformants were screened by colony PCR using primers designed to amplify across the native targeted locus (oligo-AE596; SEQ ID NO:71 and oligo-AE597; SEQ ID NO:72). The primers were designed to produce a 700 bp band in the absence of integration (e.g., "knock-in" of the BleR cassette) into the locus, or a 4.3 kb band if there was integration of a single BleR cassette into the targeted locus. In addition, colony PCR was also performed using primers designed to amplify a fragment extending from the cpSRP54 gene (oligo-AE597; SEQ ID NO:72) into the selectable marker (oligo-AE405; SEQ ID NO:73 and oligo-AE406; SEQ ID NO:74). Depending on orientation of the integrated ble cassette, a 1.2 kb band would result from either amplification by primers 405/597 or primers 406/597 spanning from within the bleR cassette out into the cpSRP54 gene. The results showed a high frequency (between 40 and 45% in this sample) of knock-in of the BleR cassette into the targeted locus in the absence of homology arms. The cpSRP54 knockouts resulted in a pale green phenotype.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically and individually indicated to be incorporated by reference.

We claim:

1. A recombinant or classically-derived *Parachlorella* LIHLA mutant having a mutated or attenuated gene encoding a chloroplastic signal recognition protein 54 (cpSRP54), wherein the mutant:

(a) exhibits at least a 20% reduction in chlorophyll under low light conditions;

(b) demonstrates a higher rate of carbon fixation on a per chlorophyll basis; and (c) demonstrates greater biomass productivity, with respect to a control alga of the same species.

2. An algal mutant according to claim 1, wherein the mutant exhibits higher photosynthetic efficiency (Y(II)) at all physiologically relevant irradiances above 250 μE·$m^{-2}\cdot s^{-1}$ with respect to a control alga of the same species.

3. An algal mutant according to claim 1, wherein the mutant exhibits lower nonphotochemical quenching (NPQ) at all physiologically relevant irradiances above 250 μE·$m^{-2}\cdot s^{-1}$ with respect to a control alga of the same species.

4. An algal mutant according to claim 1, wherein the rate of oxygen evolution is higher than that of a control alga of the same species on a per chlorophyll basis.

5. An algal mutant according to claim 1, wherein the mutant has been generated by UV irradiation, gamma irradiation, or chemical mutagenesis.

6. An algal mutant according to claim 1, wherein the mutant is a genetically engineered mutant.

7. An algal mutant according to claim 6, wherein the mutant has been genetically engineered by insertional mutagenesis, gene replacement, RNAi, antisense RNA, meganuclease genome engineering, one or more ribozymes, and/or a CRISPR/cas system.

8. An algal mutant according to claim 1, wherein the cpSRP54 comprises an amino acid sequence having at least 90% identity to SEQ ID NO:15.

9. An algal biomass comprising an algal mutant according to claim 1.

10. A method of producing an algal product, comprising culturing an algal mutant according to claim 1 and isolating at least one product from the culture.

11. A method according to claim 10, wherein the product is algal biomass.

12. A method according to claim 10, wherein the product is a lipid, a protein, a peptide, one or more amino acids, a carbohydrate, one or more nucleotides, a vitamin, a cofactor, a hormone, an antioxidant, or a pigment or colorant.

13. A method according to claim 10, wherein the alga is cultured phototrophically.

14. An algal mutant according to claim 4, wherein the rate of oxygen evolution is at least 50% higher than that of a control alga of the same species on a per chlorophyll basis.

* * * * *